(12) United States Patent
Roy et al.

(10) Patent No.: US 11,511,027 B2
(45) Date of Patent: Nov. 29, 2022

(54) HEMOFILTER FOR IN VIVO BLOOD FILTRATION

(71) Applicants: The Regents of the University of California, Oakland, CA (US); Vanderbilt University, Nashville, TN (US)

(72) Inventors: Shuvo Roy, San Ramon, CA (US); William Fissell, Oakland, CA (US); Nathan Wright, San Francisco, CA (US); Mark Goodin, Oakland, CA (US); Steven G. Goebel, Victor, NY (US); Amanda Buck, Oakland, CA (US); Joey Groszek, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 509 days.

(21) Appl. No.: 16/624,226

(22) PCT Filed: Jun. 20, 2018

(86) PCT No.: PCT/US2018/038548
§ 371 (c)(1),
(2) Date: Dec. 18, 2019

(87) PCT Pub. No.: WO2018/237036
PCT Pub. Date: Dec. 27, 2018

(65) Prior Publication Data
US 2020/0114058 A1 Apr. 16, 2020

Related U.S. Application Data

(60) Provisional application No. 62/523,131, filed on Jun. 21, 2017.

(51) Int. Cl.
*A61M 1/34* (2006.01)
*A61M 1/16* (2006.01)
(Continued)

(52) U.S. Cl.
CPC ............ *A61M 1/34* (2013.01); *A61M 1/1621* (2014.02); *A61M 1/1631* (2014.02);
(Continued)

(58) Field of Classification Search
CPC .............. A61M 1/1621; A61M 1/1631; A61M 1/1678; A61M 1/34; A61M 5/165;
(Continued)

(56) References Cited

U.S. PATENT DOCUMENTS 4,038,191 A 7/1977 Davis et al.
6,561,996 B1 5/2003 Gorsuch
(Continued)

FOREIGN PATENT DOCUMENTS

GB 2086762 A 5/1982
JP H11-137670 A 5/1999
(Continued)

OTHER PUBLICATIONS

Marom, Gil , et al., "Lagrangian methods for blood damage estimation in cardiovascular devices—How numerical implementation affects the results", Expert Review of Medical Devices 13(2), 2016, 113-122.

*Primary Examiner* — John Kim
(74) *Attorney, Agent, or Firm* — Edward J. Baba; Shweta Chandra; Bozicevic, Field & Francis LLP

(57) ABSTRACT

Hemofilters for in vivo filtration of blood are disclosed. The hemofilters disclosed herein provide an optimal flow of blood through the filtration channels while maintaining a pressure gradient across the filtration channel walls to enhance filtration and minimize turbulence and stagnation of blood in the hemofilter.

20 Claims, 48 Drawing Sheets

(51) Int. Cl.
*B01D 63/08* (2006.01)
*A61M 5/165* (2006.01)
*F28F 9/02* (2006.01)

(52) U.S. Cl.
CPC .......... *A61M 1/1678* (2013.01); *A61M 5/165* (2013.01); *B01D 63/082* (2013.01); *B01D 63/085* (2013.01); *A61M 2205/04* (2013.01); *A61M 2205/3334* (2013.01); *A61M 2205/75* (2013.01); *A61M 2206/10* (2013.01); *A61M 2206/11* (2013.01); *B01D 2313/105* (2013.01); *B01D 2313/125* (2013.01); *F28F 2009/029* (2013.01)

(58) Field of Classification Search
CPC ...... A61M 2205/04; A61M 2205/3334; A61M 2205/75; A61M 2206/10; A61M 2206/11; B01D 63/082; B01D 63/085; B01D 2313/105; B01D 2313/125; F28F 2009/029

See application file for complete search history.

(56) References Cited

U.S. PATENT DOCUMENTS

| | | | |
|---|---|---|---|
| 6,758,971 | B1 | 7/2004 | Haight |
| 2002/0062953 | A1 | 5/2002 | Demuth et al. |
| 2009/0131858 | A1 | 5/2009 | Fissell et al. |
| 2011/0303598 | A1 | 12/2011 | Lo et al. |
| 2012/0138151 | A1 | 6/2012 | Tonkovich et al. |
| 2012/0289881 | A1 | 11/2012 | Lyu et al. |

FOREIGN PATENT DOCUMENTS

| | | |
|---|---|---|
| JP | 2009131573 A | 6/2009 |
| JP | 2010069278 A | 4/2010 |

Wall Shear Stress dynecm2

HEMOFILTER FOR IN VIVO BLOOD FILTRATION

CROSS-REFERENCE

This application claims the benefit of U.S. Provisional Patent Application No. 62/523,131, filed Jun. 21, 2017, which application is incorporated herein by reference in its entirety.

STATEMENT REGARDING FEDERALLY SPONSORED RESEARCH

This invention was made with government support under grant no. U01 EB021214 awarded by the National Institutes of Health. The government has certain rights in the invention.

INTRODUCTION

End Stage Renal Disease (ESRD) remains a major public health problem in the United States, afflicting over 615,000 people with nearly 116,000 new patients initiating treatment each year. Due to the shortfall in organ availability, the majority of ESRD patients in the United States undergo in-center, 3-4 hour, thrice weekly dialysis, such as hemodialysis or peritoneal dialysis.

Hemodialysis involves passing a patient's blood against a synthetic or semisynthetic membrane and inducing diffusive transport of toxins from the blood into a bath of dialysate on the other side of the membrane. In peritoneal dialysis, the patient's parietal peritoneal epithelium performs the function of the dialysis membrane.

SUMMARY

A hemofilter for use in for filtering blood in vivo, the hemofilter is provided. In certain embodiments, the hemofilter includes an extended inlet manifold; a plurality of filtration channels; and an extended outlet manifold, the extended inlet manifold comprising a first region comprising a circular inlet configured for connection to a blood vessel of an individual; and a transition section in which lumen of the extended inlet manifold transitions from having a circular cross-section to having a substantially rectangular cross-section; and a second region comprising a U-shaped turn and followed by a linear tapered section, the linear tapered section comprising a plurality of openings in fluid communication with the plurality of filtration channels, wherein the plurality of filtration channels are arranged in a spaced-apart stacked configuration and are in fluid communication with a plurality of openings in a first region of the outlet manifold, wherein the first region of the outlet manifold is parallel to the linear tapered section of the extended inlet manifold and is reverse-tapered and wherein the outlet manifold comprises a second region comprising a transition section in which lumen of the outlet manifold transitions from having a rectangular cross-section to having a circular cross-section; and a circular outlet defined by the circular cross-section of the outlet manifold, and wherein the hemofilter is configured for entry of blood through the inlet and for transporting the blood through the transition section of the extended inlet manifold to the tapered linear section, into the plurality of filtration channels to the first region of the outlet manifold, into the transition section of the outlet manifold, and exit via the circular outlet.

In certain embodiments, the plurality of filtration channels are substantially rectangular (e.g., with a length longer than width and substantially rounded corners) and are stacked in a parallel configuration.

In certain embodiments, the transition section in extended inlet manifold includes a turn which changes direction of blood flow with reference to the direction in the inlet by 60°-120°.

In certain embodiments, the U-shaped turn in the second region of the extended inlet manifold changes the direction of blood flow with reference to the direction in the transition section by 150° and 210°.

In certain embodiments, the tapered section of the extended inlet manifold decreases in height. In certain embodiments, the tapered section of the extended inlet manifold decreases in width.

In certain embodiments, the plurality of filtration channels comprises 2-50 channels, e.g., 6-30 channels.

In certain embodiments, the plurality of filtration channels comprises a first curved region connected to the tapered section of the extended inlet manifold, a linear section, and a second curved region connected to the reverse-tapered section of the outlet manifold, wherein the curvature of the first curved region is opposite to the curvature of the second curved region.

In certain embodiments, the plurality of channels each define a rectangular channel lumen enclosed by a top surface, a bottom surface, and side walls connecting the top and bottom surfaces.

In certain embodiments, the top surface comprises a membrane for filtration of blood in the channel lumen. In certain embodiments, the bottom surface comprises a membrane for filtration of blood in the channel lumen.

In certain embodiments, the tapered section of the extended inlet manifold and the reverse-tapered section of the outlet manifold and a top channel of the plurality of channels and a bottom channel of the plurality of channels are arranged in shape of a parallelogram. In some embodiments, the acute angles of the parallelogram shape defined by the configuration of the hemofilter may range from 75-25 degree, such as, 70-30 degree, 65-30 degree, 65-35 degree, or 50-40 degree and the obtuse angles of the parallelogram shape defined by the configuration of the hemofilter may range from 105-155 degree, such as, 110-150 degree, 115-150 degree, 115-145 degree, or 130-140 degree, respectively.

In certain embodiments, the plurality of channels are shaped and dimensioned to provide a volumetric flow rate of 20-100 ml/min, e.g., 25-100 ml/min for blood flowing through each of the channels and wherein the hemofilter provides a volumetric flow rate of 750-2000 ml/min for blood flowing through the hemofilter.

In certain embodiments, each of the plurality of channels has a length of 10 mm-200 mm, e.g., 40 mm-100 mm. In certain embodiments, each of the plurality of channels has a width of 5 mm-100 mm, e.g., 10 mm-40 mm. In certain embodiments, each of the plurality of channels has a height of 0.5 mm-2.5 mm.

Also provided herein is a hemofilter for use in filtering blood in vivo, the hemofilter comprising: an extended inlet conduit; a single serpentine filtration channel; and an outlet conduit; the extended inlet conduit comprising: a first region comprising: an inlet having a circular cross section geometry configured for connection to a blood vessel of an individual; and a transition region in which lumen enclosed by the first region transitions from the circular cross section shape into a rectangular cross section shape; a second region comprising a rectangular cross section and a curved region connected to the serpentine filtration channel; the serpentine filtration channel comprising: a plurality of filtration sections arranged in a spaced-apart stacked configuration wherein the plurality of filtration sections are connected via turnaround sections; and the outlet comprising: first region having a rectangular cross-section; and a second region that transitions from rectangular to a circular cross section and terminates in a circular outlet configured for connection to a blood vessel of the individual.

Also provided herein is a hemofilter that includes an extended inlet conduit; a single serpentine filtration channel; and an outlet conduit; the extended inlet conduit comprising: an inlet; a first transition region; a first turnaround section; a second transition region; a second turnaround section; wherein in the first transition region the inlet transitions from a circular cross section, configured for connection to a blood vessel of an individual, into a substantially rectangular cross section, wherein the rectangular cross section at the end of the first transition region matches the rectangular cross section of the first turnaround section, wherein in the second transition region the first turnaround section expands in width such that the rectangular cross section at the end of the second transition region matches the rectangular cross section of the second turnaround section, wherein the rectangular cross section of the second turnaround section matches that of the serpentine filtration channel; the serpentine filtration channel comprising a plurality of filtration sections arranged in a spaced-apart stacked configuration wherein the plurality of filtration sections are connected via turnaround sections; and the outlet comprising first region having a rectangular cross-section; and a second region that transitions from rectangular to a circular cross section and terminates in a circular outlet configured for connection to a blood vessel of an individual.

In certain embodiments, the plurality of filtration sections comprise 2-50 filtration sections, e.g., 6-30 filtration sections, each disposed between two turnaround sections.

In certain embodiments, the plurality of filtration sections each define a rectangular lumen enclosed by a top surface, a bottom surface, and side walls connecting the top and bottom surfaces.

In certain embodiments, the top surface comprises a membrane for filtration of blood in the channel lumen. In certain embodiments, the bottom surface comprises a membrane for filtration of blood in the channel lumen.

In certain embodiments, the plurality of filtration sections are shaped and dimensioned to provide a volumetric flow rate of 20-100 ml/min for blood flowing through the each of the filtration sections and wherein the hemofilter provides a volumetric flow rate of 750-2000 ml/min for blood flowing through the hemofilter.

In certain embodiments, each of the plurality of filtration sections has a length of 10 mm-200 mm, e.g., 40 mm-100 mm. In certain embodiments, each of the plurality of filtration sections has a width of 5 mm-100 mm, e.g., 10 mm-40 mm. In certain embodiments, each of the plurality of filtration sections has a height of 0.5 mm-2.5 mm.

In certain embodiments, the curvature of the turnaround sections is non-uniform.

In certain embodiments, the curvature of the turnaround sections is circular.

In certain embodiments, the curvature of the turnaround sections is elliptical.

In certain embodiments, the height of a filtration section increases from a proximal end, at which blood enter the filtration section, towards the distal end, at which blood exits the filtration section and flows to a turnaround section.

The hemofilter may be used for filtering blood in vivo in a subject in need thereof. In certain embodiments, the subject may have a reduced renal function. The hemofilter provided herein may be incorporated in an implantable artificial kidney for filtering the subject's blood in vivo. The artificial kidney may replace or supplement dialysis treatment for the subject.

In certain embodiments, the subject may have reduced heart function, such as, congestive heart failure (CHF). The hemofilter provided herein may be incorporated in a filtration device implanted into the subject for filtration of blood in order to unload blood volume accumulated due to the reduced heart function, such as, CHF.

In certain embodiments, the subject may have reduced liver function, such as, liver failure. The hemofilter provided herein may be incorporated in a filtration device implanted into the subject for filtration of blood in order to filter blood in the subject having reduced liver function, such as, liver failure.

BRIEF DESCRIPTION OF THE DRAWINGS

FIG. 65 shows a smooth flow into the outlet conduit.

DETAILED DESCRIPTION

Figure 1:
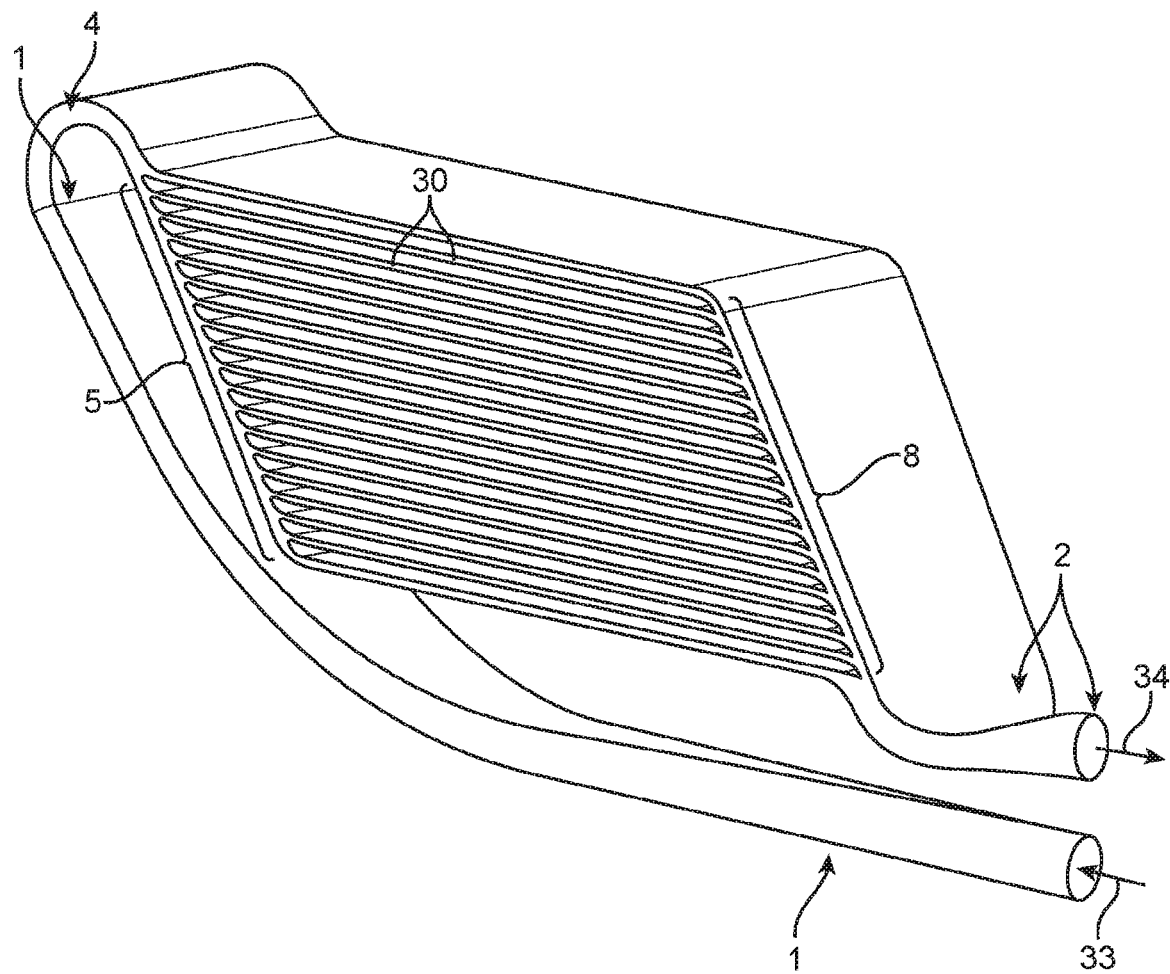
FIG. 1 illustrates an embodiment of a hemofilter as disclosed herein.

Provided herein are hemofilters for use in an implantable filtration device, e.g., artificial kidney for continuous filtration (ultrafiltration and/or dialysis) of blood in an individual. The hemofilters disclosed herein provide an optimal flow of blood through the filtration channels while maintaining a pressure gradient across the filtration channel walls to enhance filtration and minimize areas of high shear and stagnation of blood in the hemofilter.

Before exemplary embodiments of the present invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a membrane" includes a plurality of such membranes and reference to "the parallel conduit" includes reference to one or more conduits, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. To the extent such publications may set out definitions of a term that conflicts with the explicit or implicit definition of the present disclosure, the definition of the present disclosure controls.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Definitions

The term "about" or "substantially similar" as used herein when referring to a measurable value such as a physical quantity, a temporal duration, and the like, is meant to encompass variations of ±20%, such as ±10%, such as ±5%, ±1%, including ±0.1% from the specified value, as such variations are typical of measurements characterizing the disclosed devices or appropriate to perform the disclosed methods.

As used herein "substantially", may be applied to modify any quantitative representation that could permissibly vary without resulting in a change in the basic function to which it is related. For example, two silicon nanoporous membranes may be somewhat non-parallel to each other if the stackable structure of the membranes, and the hydrodynamic and/or filtration properties of the silicon nanoporous membranes are not materially altered.

A "plurality" contains at least 2 members. In certain cases, a plurality may have at least 10, at least 20, at least 30, at least 100, at least 10,000, or more members.

"Biocompatible," as used herein, refers to a property of a material that allows for prolonged contact with a tissue in a subject without causing toxicity or significant damage.

"Planar" as used herein, may be applied to describe a three dimensional shape of any object, where the length scale of two dimensions that are substantially perpendicular to each other (e.g., length and width) is longer than the length scale of a third dimension (e.g., thickness) that is substantially perpendicular to both of the other two dimensions. The length scale of one of the two longer dimensions may be similar to or different from the other longer dimension. The first two dimensions may define a plane.

"Through channel" or "through hole" is used herein to describe a channel or hole that connects one side of the structure in which the channel or hole is formed, to another side of the structure. The first side and the second side are generally opposite sides of the structure.

"Nanopore" as used herein, refers to a pore that penetrates a substrate from one side to another, where the pore has at least one lateral dimension (e.g., width and/or length, but not the height/thickness of the pore across the substrate) that is in the nanometer range, e.g., in the range of 1.0 nm to 1,000 nm.

"Pumpless" as used in reference to a device connected to a blood vessel or a blood circuit is meant to refer to the absence of a pump mechanism other than the heart that drives blood flow through the circulatory system of an individual.

As used herein, the term "individual" refers to any animal, such as a mammal like a dog, cat, livestock (e.g., pig), non-human primate, and including a human. The individual may be a patient with a compromised kidney function and/or in need of dialysis, compromised heart function, and/or compromised liver function.

As used herein, the term "filtration" as used herein refers to a process of separating smaller particulates and larger particulates present in a fluid, by passing the fluid through or over a filtering material that will not pass particulates having a size larger than pores in the filter. Filtration is also affected by flow rate of the fluid as well as concentration and pressure gradient across the filter. The filter may be a semipermeable membrane.

As used herein, the term "dialysis" refers to a form of filtration, or a process of selective diffusion through a membrane; it is typically used to separate low-molecular weight solutes that diffuse through the membrane from the colloidal and high-molecular weight solutes which do not. In some embodiments, a feed of fluid is passed over a semipermeable membrane, and a feed of dialysate is passed over the other side of that membrane; the membrane is wetted by one or both fluids, and then there is diffusive transport of solutes between the fluids. The composition of one fluid, the dialysate, may be used to deplete the composition of the other fluid, the feed fluid, of some molecule or molecules.

As used herein, the term "ultrafiltration" refers to subjecting a fluid to filtration under pressure, where the filtered material is very small; typically, the fluid includes colloidal, dissolved solutes or very fine solid materials, and the filter is a microporous, nanoporous, or a semi-permeable medium. A typical medium is a membrane. The fluid to be filtered is referred to as the "feed fluid." During ultrafiltration, the feed fluid is separated into a "permeate" or "filtrate" or "ultrafiltrate," which has been filtered through the filter, and a "retentate," which is that part of the feed fluid which did not get filtered through the medium, or which is retained within the membrane. Ultrafiltration does not require a dialysate be passed over the other side of the membrane.

As used herein, the term "dialysate" is used to refer to the fluid into which low-molecular weight solutes diffuse through a membrane from another fluid (typically, the feed fluid) initially containing these solutes.

As used herein, the term "polysilicon" refers to a polycrystalline form of silicon that is deposited as a thin film. It is used in microelectronics for transistors and wiring. In MEMS, polysilicon is usually used as structural material for devices.

Hemofilters

Provided herein are hemofilters for use in an implantable filtration device, e.g., an artificial kidney for continuation filtration of blood in an individual. The hemofilters disclosed herein provide an optimal flow of blood through the hemofilter while maintaining a pressure gradient across the filtration channel walls to enhance filtration and minimize areas of high shear and stagnation of blood in the hemofilter. The hemofilters disclosed herein do not require a pump to flow blood through the channels and can perform filtration (dialysis or ultrafiltration) of blood under systolic blood pressure.

The hemofilters disclosed herein include an inlet conduit that connects to the circulatory system of an individual to transport arterial blood through channels that include filters (e.g., membranes through which certain molecules, such as, uremic toxins, excess ions, small solutes, water, etc. can pass) and an outlet conduit through which the filtered blood exits the hemofilter. The other chamber of the implantable filtration device, such as, an artificial kidney may be a bioreactor chamber which may include cells that express or provide one or more desired factors to a filtered blood that is to be returned to the individual. Suitable bioreactor systems are described in, e.g., US 20090131858, which is incorporated herein by reference.

In certain embodiments, the hemofilter may include an extended inlet conduit that transitions from a circular cross section into rectangular cross section, where the circular cross section region connects to a blood vessel of an individual and the rectangular cross section connects to one or more channels configured for filtration of blood. In certain embodiments, the hemofilter may also include an outlet conduit that transitions from a rectangular cross section into a circular cross section, where the rectangular cross section connects to the one or more channels configured for filtration of blood and the circular cross section connects to a blood vessel of the individual or to a bioreactor chamber of the in vivo filtration device, e.g., an artificial kidney, which returns the filtered blood to a blood vessel of the individual. In certain embodiments, the extended inlet conduit is longer than the outlet conduit and includes one or more turns to enable adjacent placement of the circular cross section region of the extended inlet conduit and outlet conduits. In one aspect, a hemofilter as provided herein may have an extended inlet conduit that connects to a single serpentine filtration channel. In a second aspect, a hemofilter as provided herein may have an extended inlet conduit that includes a plurality of openings connected to a plurality of filtration channels. An extended inlet conduit that includes a plurality of openings is referred to herein as an extended inlet manifold. Hemofilters with an extended inlet manifold connected to a plurality of filtration channels and hemofilters with an extended inlet conduit that connects to a single serpentine filtration channel are described in detail below.

In certain embodiments, the tapered section of the extended inlet manifold and the reverse-tapered section of the outlet manifold and a top channel of the plurality of channels and a bottom channel of the plurality of channels are arranged in shape of a parallelogram.

Hemofilters with Extended Inlet Manifold

Embodiments of the implantable filtration device, such as, a bioartificial kidney, include a hemofilter with an extended inlet manifold that distributes blood into a plurality of filtration channels. The plurality of filtration channels is in fluid communication with an outlet manifold which connects to a bioreactor chamber of the in vivo filtration device, e.g., an artificial kidney, which returns the filtered blood to circulatory system of the individual implanted with the in vivo filtration device (e.g., artificial kidney) or directly connects to a blood vessel of the individual. In certain embodiments, the filtration channels are arranged in a substantially parallel-plate like arrangement.

In certain embodiments, the extended inlet manifold includes a first region and a second region enclosing a space or lumen defining a conduit through which blood can flow. The first region may include a substantially circular opening forming an inlet configured for connection to a blood vessel of an individual into whom the in vivo filtration device (e.g., an artificial kidney) is implanted. The first region of the extended inlet manifold may also include a transition region in which the circular opening transitions into a flattened shape having a substantially rectangular cross section in order to guide the blood flow into the substantially rectangular cross section region. As such, the lumen enclosed by the extended inlet manifold transitions from having a circular cross-section into a flattened substantially rectangular cross-section. The second region of the extended inlet manifold starts at the point where the transition into the substantially rectangular cross section is complete and at which point, along the extended inlet manifold, the cross section area of the conduit defined by the extended inlet manifold is constant. The second region of the extended inlet manifold includes a curved region having the substantially rectangular cross section and further includes a linear region having a plurality of openings fluidically connected to the plurality of filtration channels. In certain cases, the linear region of the second region may have a tapering configuration in which at least the height of the rectangular cross section decreases. In certain embodiments, in addition to a decrease in height of the rectangular cross section of the linear region of the second region of the extended inlet manifold, the width may also decrease. The plurality of channels is in fluidic communication with an outlet manifold having a first region and a second region. The first region may have a substantially rectangular cross section that is connected to the plurality of channels. The second region of the outlet manifold may include an outlet having a substantially circular cross section and a transition area in which the rectangular cross section of the outlet manifold transitions into a substantially circular cross section. The outlet may be configured for connecting to a bioreactor chamber of the in vivo filtration device such as an artificial kidney which returns the filtered blood to a blood vessel of the individual implanted with the in vivo filtration device. The inlet of the hemofilter may be adjacent to facilitate connecting the inlet and outlet of the hemofilter to adjacent blood vessels of the individual. For example, the inlet and outlet of the hemofilter may be positioned for connection to renal artery and renal vein, respectively, of an individual.

In certain embodiments, the inlet of the first region of the extended inlet manifold may be have a standard geometry compatible for connecting to a blood vessel of an individual. In certain aspects, the inlet may be substantially circular. As used herein, the phrase substantially circular refers to a circular shape or an oval shape formed upon slight compression of the circular opening. The diameter of the inlet may range from 3 mm-8 mm and may be selected based upon the blood vessel to which the in vivo filtration device will be connected. In certain embodiments, the diameter of the inlet may range from 3 mm-7 mm, 3 mm-6 mm, 3 mm-5 mm, 4 mm-7 mm, or 4 mm-6 mm. The inlet may be grafted (e.g., sewed) directly to a blood vessel or may be connected to a biocompatible tubing that in turn is grafted to a blood vessel.

The first region of the extended inlet manifold may include a transition region where the circular cross section at the inlet transitions into a substantially rectangular cross section that has a decreased height compared to the diameter of the inlet and an increased width compared to the diameter of the inlet. The term "substantially rectangular" as used herein refers to a rectangular shape that has a width that is larger than the height and corners that are either rounded or form a 90° angle. The dimensions of the substantially rectangular cross section region of the extended inlet manifold at the first region may be about 2 mm-8 mm height and 5 mm-10 mm in width (transitioning from a diameter of 3 mm-8 mm, respectively) and may transition to a substantially rectangular cross section having a dimension at the start of the second region ranging from 7 mm-50 mm in width and 0.5 mm-8 mm height. In certain embodiments, the diameter of the inlet may range from 4 mm-7 mm and the rectangular cross section at the start of the second region may range from 0.5 mm-3 mm height and 20 mm-50 mm width, e.g., 0.5 mm-2.5 mm height and 20 mm-40 mm width, 0.5 mm-2 mm height and 20 mm-35 mm width, 0.75 mm-2 mm height and 25 mm-35 mm width, or 1 mm-2 mm height and 25 mm-30 mm width. In certain embodiments, the first region may also include a turn to change the direction of flow of blood as compared to the direction of the flow of blood at the inlet. For example, the first region may include an L-shaped turn or a curvature between 60°-120° that changes the direction of blood flow by an angle of about 60°-120° compared to the direction of blood flow at the inlet.

The second region of the extended inlet manifold may include a U-shaped region that further changes the direction of blood flow where the change of direction is at an angle of 150°-210° compared to the direction of blood flow at the end of the first turn (e.g., L-shaped turn).

The second region of the extended inlet manifold after the U-shaped turn includes a tapered region that decreases in cross section area from a proximal region to a distal region. As used herein proximal region is the region closer to the inlet of the device and a distal region is farther from the proximal region. In certain aspects, the tapered region decreases in height from the proximal region towards the distal region with or without a decrease in width of the region thereby decreasing the cross-sectional area of the conduit defined by the manifold. In certain embodiments, the height of the second region may decrease such that as the blood is distributed into the plurality of channels and the volume of blood in the extended inlet manifold decreases, the decreased height (and the decreased cross section area) of the extended inlet manifold ensures maintenance of blood flowing into subsequent downstream channels such that the rate of blood flow in each of the plurality of channels is substantially comparable. As used herein, the term "downstream" refers to a location towards which the blood is flowing after it flows through the U-shaped turn in the second region of the extended inlet manifold. The tapered end of the extended inlet manifold may lead into the last of the plurality of filtration channels while the remainder of the plurality of channels extends from periodically placed openings in the extended inlet manifold. In certain embodiments, the first channel of the plurality of channels may be referred to as a top channel and the last channel may be referred to as bottom channel.

In certain embodiments, the plurality of filtration channels are spaced apart by a predetermined distance along the second region of the extended inlet manifold, where the predetermined distance is constant or variable (the distance may increase or decrease from one channel to another). The distance of separation between the channels can be determined based upon a number of factors, such as, the number of channels, the length of the second region, the surface area of the membrane portion of the channels and so forth. In some embodiments, the channels are spaced apart by 0.50 mm-2 mm along the second region of the extended inlet manifold. In certain aspects, the flow rate of blood through the channels may be controlled further by including an optional indent in the extended inlet manifold which reduces the cross sectional area of the conduit defined by the extended inlet manifold at the entrance of a filtration channel. For example, indents may be arranged periodically along the second region of the extended inlet manifold (after the U-shaped turn) such that the cross section (height) of the region is decreased proximate the opening for the filtration channels positioned at the level of the indent. In certain embodiments, the indent may reduce the cross sectional area of the extended inlet manifold at the entrance to each of the plurality of filtration channels by 1% to 25% compared to the cross sectional area immediately upstream to the opening to the channel.

In certain embodiments, the height of the tapered section of the second region of the extended inlet manifold (after the U-shaped turn) may decrease in a range of a quarter to an eighth of the initial height (height before start of the tapering). In certain embodiments, the height of the end of the tapered section (e.g., at the last channel) may be a quarter to an eighth of the initial height (height before start of the tapering). In certain embodiments, the height of the second region of the extended inlet manifold may be determined by the desired flow rate of blood traversing through the manifold. For example, the height of the substantially rectangular cross section may be set at square root of local volume flow rate, i.e., the height may be decreased to compensate for the decrease in the local volume of blood at each location downstream to an opening feeding into a filtration channel. In certain embodiments, the height of the conduit decreases with the square root of volumetric flow rate:

($h$=local volume flow rate$^{0.5}$), (Equation 1), where h is the conduit height in the tapered section 5. In certain embodiments, the height of the conduit 5 decreases linearly with the local volumetric flow rate:

Local volume flow rate=$h \times w \times$local average velocity (Equation 2), where h is the conduit height, and w is the conduit width.

In certain embodiments, instead of or in addition to the second region of the extended inlet manifold decreasing in height, it may decrease in width such that the width decreases by a factor of 0.9-0.75 of the starting width. In certain embodiments, the width of the end of the tapered region (e.g., at the last channel) may be at the width at the beginning of the tapering second region or may decrease by a factor of 0.9-0.75 times the width at the start of the tapered section.

The plurality of filtration channels may define a conduit having a rectangular cross section. The width of the filtration channels may be comparable to the width of the tapered section of the extended inlet manifold. The height of the rectangular filtration channels may be in the range of 0.5 mm-5 mm (e.g., of 0.5 mm-4 mm, 1 mm-4 mm, 1 mm-3 mm, 1 mm-2 mm, 1.5 mm-2 mm, 1 mm-2 mm, or 0.5 mm-2 mm) and the width of the rectangular filtration channels may be in the range of 8 mm-50 mm (e.g., 9 mm-50 mm, 10 mm-50 mm, 10 mm-40 mm, or 20 mm-40 mm). The length of the filtration channels can vary based on a number of factors, such as, the surface area of the membrane section in the filtration channels, the height and width of the channels as well as the number of channels. In certain embodiments, the length of the channel may be in the range of 40 mm-100 mm (e.g., 40 mm-90 mm, 40 mm-80 mm, 40 mm-70 mm, or 50 mm-70 mm). The portion of the filtration channels where a membrane forms the walls of the channels may be vary depending upon the dimensions and number of the channels. In certain embodiments, at least a quarter, at least a half, at least a two third, or more of the channel is formed from a membrane. In certain embodiments, the plurality of channels may include a surface area of between 0.016 and 0.16 square meters that includes a membrane. In certain embodiments, the plurality of channels may each have a membrane section providing a surface area of 0.0008 $m^2$-0.008 $m^2$ per channel for filtration of blood flowing through the channels. In certain embodiments, the plurality of channels in the hemofilter may provide a filtration area (formed by the membrane) in the range of 0.016 $m^2$-0.16 $m^2$, e.g., 0.032 $m^2$-0.16 $m^2$, 0.064 $m^2$-0.16 $m^2$, 0.064 $m^2$-0.10 $m^2$, or 0.064 $m^2$-0.09 $m^2$. The number channels may be 4 or more, such as up to 50, e.g., 5-40, 5-30, 5-25. In certain examples, the number of channels can be in the range of 10-40 channels, such as, 10-35 channels, 10-30 channels, 15-40 channels, or 15-30 channels. As noted herein, the number of channels can be increased and at least one of length or width of the channels decreased or vice versa to provide a target filtration surface area.

The membrane portion of the filtration channels may be affixed to a scaffold for connecting to the inlet and outlet manifolds of the hemofilter. In certain aspects, the scaffold may define two side walls of the channel and an enclosed inlet and outlet of the channels and may provide open top and/or an open bottom which may be covered by the membrane to provide the filtration surface. The membrane used for filtration may be a biocompatible membrane used in the field of dialysis and/or ultrafiltration, such as, silicone membrane, silicon nanopore membrane (SNM), silicon nitride, silica, atomically thin membrane such as graphene, silicon, silicene, molybdenum disulfide ($MoS_2$), etc., or a combination thereof, or a polymer. The membrane may be a planar membrane is affixed to the scaffold. In certain aspects, the planar membrane may be folded into a tube having a rectangular cross section. In certain aspects, the planar membrane is not a hollow fiber like membrane which provides a minimal surface area for filtration and requires use of 10000 hollow fibers that are over 150 mm in length which is not suitable for an implantable filtration device, such as, an artificial kidney.

As noted herein, the plurality of channels may be in a stacked configuration where the channels are substantially parallel to each other and may be oriented at an angle with reference to the second region of the extended inlet manifold. For example, the angle between the tapered section and the top surface of the filtration channels may be about 90 degrees-150 degrees and the angle between the bottom surface of the filtration channels and the tapered section may be about 90 degrees-30 degrees. The connection between the tapered section of the second region of the extended inlet manifold and the plurality of filtration channels define walls that are linear or curved. In certain aspects, the plurality of filtration channels may be connected to the tapered section via a curved flow path where the blood traversing through the tapered section changes direction by less than 90 degrees to enter the plurality of channels. The curved flow path may be provided by including a curved conduit that gradually changes the direction of blood flow. Thus in certain aspects, a curving flow path connects the inlet manifold to the plurality of filtration channels. The curving flow path may have a substantially rectangular cross section geometry and may have a width that is comparable to width of the tapered section of the manifold and/or width of the filtration channels or a width shorter than the width of the tapered section of the manifold and/or width of the filtration channels. In certain embodiments, the curving flow path may be provided by a curved region of the filtration channels. In such an embodiment, the filtration channels may include a first curved section that includes a curved top surface and a curved bottom surface and two side walls extending between the top and bottom curved surfaces, where the curved top surface forms an obtuse angle with the tapered section of the extended inlet manifold; a linear section that includes a planar top surface and planar bottom surface and two side walls extending between the top and bottom planar surfaces; and a second curved section that includes a curved top surface and a curved bottom surface and two side walls extending between the top and bottom curved surfaces, where the curved top surface forms an acute angle with a reverse-tapered section of the outlet manifold. In such embodiments, at least a portion of the linear section may include a membrane for filtration of blood.

In certain embodiments, the top and bottom curved surfaces of the first curved section of the plurality of filtration channels may be spaced apart to define a conduit having a substantially constant cross section area or may be spaced to provide a smaller cross section area at the entrance of the channels which cross section area increases towards the linear section of the filtration channel. The pinched or constricted entrance may facilitate even distribution of the blood into the plurality of channels.

In certain embodiments, the top and bottom curved surfaces of the second curved section of the plurality of filtration channels may be spaced apart to define a conduit having a substantially constant cross section area or may be spaced to provide a smaller cross section area at the exit of the channels which cross section area decreases from the linear section of the filtration channel towards the reverse-tapered outlet manifold. The pinched or constricted exit may facilitate drainage of the filtered blood into the outlet manifold at a slower speed and provide a longer time for filtration across the membrane in the linear section of the channels.

As noted above, the outlet manifold may include a first region that is reverse-tapered such that the cross section area of the first region increases from the proximal end (where a first filtration channel or the top channel of the plurality of channels is connected to the outlet manifold) towards the distal end. The dimensions of the reverse-tapered section of the outlet manifold may be same or similar to that of the tapered section of the extended inlet manifold. The first region of the outlet manifold may have a substantially rectangular geometry similar to the tapered section of the extended inlet manifold. The second region of the outlet manifold may include a transition region in which the rectangular cross section of the outlet manifold changes into a circular cross section at the outlet of the hemofilter. The outlet may be circular and have a diameter comparable to that of the inlet. The reversed tapered section of the outlet manifold may be substantially parallel to the tapered section of the inlet manifold.

Hemofilter such as those depicted in FIGS. 1-23 were designed and advanced Computational Fluid Dynamic (CFD) tools were used to model blood flow through such hemofilters. The CFD models incorporated pulsatile flow boundary conditions based on in vivo ultrasound measurements of blood flow.

FIGS. 1-23 illustrate embodiments of a hemofilter comprising an extended inlet manifold, an outlet manifold, and a plurality of channels between the extended inlet manifold and outlet manifold.

FIG. 1 depicts a hemofilter that includes an extended inlet manifold having a first region 1 with a substantially circular opening forming an inlet 33 configured for connection to a blood vessel of an individual into whom the filtration device is implanted. The first region 1 includes a transition region in which the inlet conduit transitions from a circular cross-sectional geometry to a flattened shape with a substantially rectangular cross-sectional geometry. The second region of the extended inlet manifold has the substantially rectangular cross section geometry and includes a U-shaped turn 4 that leads into a tapered section 5 of the extended inlet manifold which includes a plurality of openings fluidically connected to the plurality of filtration channels 30. The plurality of filtration channels are in a stacked and substantially parallel configuration. The plurality of filtration channels are fluidically connected to a first region 6 of an outlet manifold that has substantially rectangular cross section geometry and a plurality of openings from connection to the plurality of filtration channels. The first region 8 of the outlet manifold includes a reverse taper where the rectangular cross section geometry of the first region 8 of the outlet manifold increases in area towards a second region 2 of the outlet manifold. The second region 2 of the outlet manifold includes a transition area in which the rectangular cross section of the outlet manifold transitions into a substantially circular cross section forming an outlet 34 that connects to a blood vessel of the individual.

Aspects of the extended inlet and outlet include a smooth transition of the inlet conduit from a circular cross-sectional geometry to a rectangular cross-sectional geometry that enable maintenance of wall shear stress above values needed to minimize the potential for thrombus formation. In some embodiments, the wall shear stress needed to minimize the potential for thrombus formation is greater than 10 dyne/$cm^2$.

Figure 2:
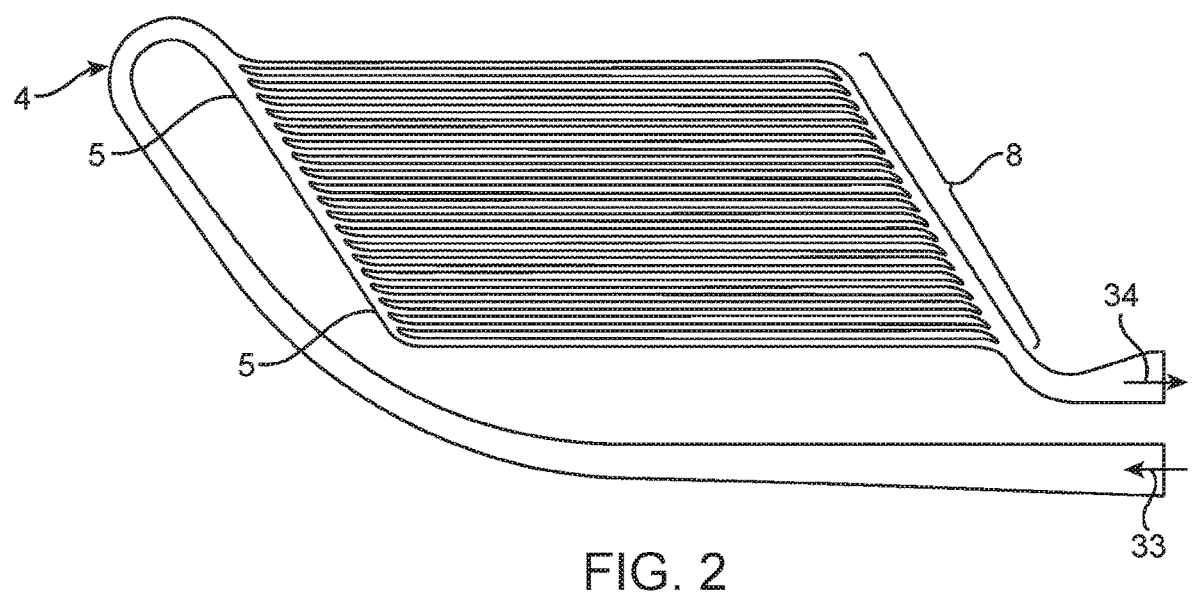
FIG. 2 provides a side view of the extended inlet of the hemofilter depicted in FIG. 1.

FIG. 2 provides another view of the extended inlet manifold hemofilter depicted in FIG. 1. FIG. 2 shows the U-shaped turn 4 in second region of the extended inlet manifold that changes the blood flow direction by about 150 to 210 degrees with reference to the direction of blood flow in the transition area of the first region. FIG. 2 also shows the tapered section 5 of the second region of the extended inlet manifold. In certain embodiments, the height of the conduit 5 decreases with the square root of volumetric flow rate:

($h$=local volume flow rate$^{0.5}$), (Equation 1), where h is the conduit height in the tapered section 5. In certain embodiments, the height of the conduit 5 decreases linearly with the local volumetric flow rate:

Local volume flow rate=$h \times w \times$local average velocity (Equation 2), where h is the conduit height, and w is the conduit width.

Figure 3:
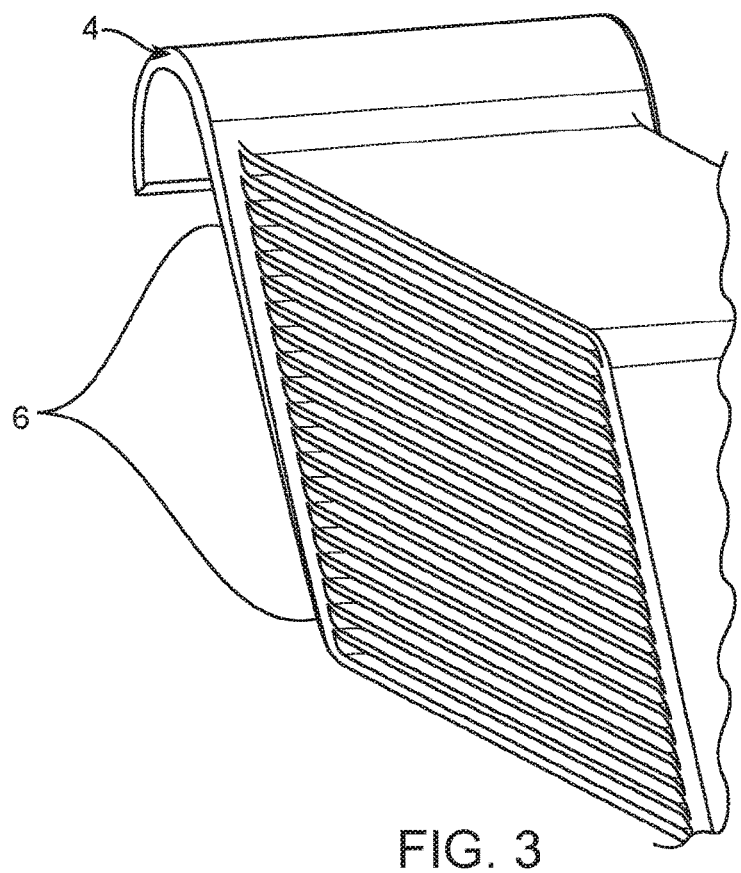
FIG. 3 provides a side view of an embodiment of a hemofilter showing an inlet manifold with a tapering width.

FIG. 3 provides a side view of a hemofilter showing tapered conduit 6 where the height as well as width of the conduit decreases. In such embodiments, the inlet manifold conduit width decreases from initial value range between 7.5 mm and 50 mm to a final value range between 7 mm and 40 mm.

Figure 4:
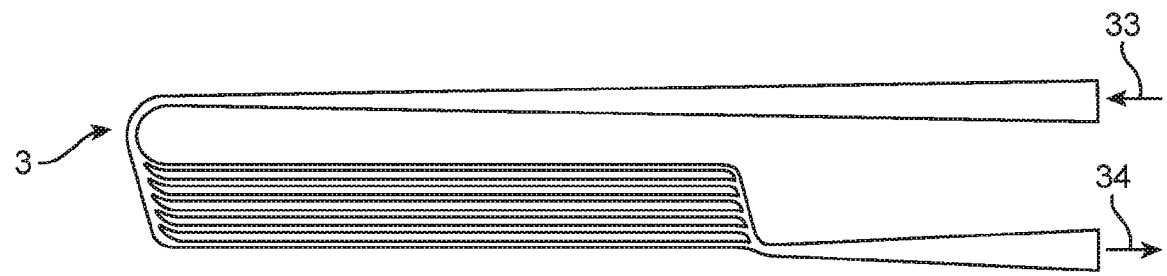
FIG. 4 depicts another embodiment of a hemofilter as disclosed herein.

FIG. 4 depicts a hemofilter where extended inlet manifold is shaped to include a U-turn 3 to change blood flow direction by about 60 to 120 degrees with reference to the initial direction of the blood flow. The extended inlet manifold includes only a single turn instead of the two turns as shown in FIGS. 1 and 2 as this embodiment of the hemofilter includes fewer filtration channels (six verses twenty) and hence two turns are not needed to provide adjacent placement of the inlet and outlet openings. As used herein, adjacent in the context of positioning of the inlet and outlet of a hemofilter refers to placement at distance separated by less than 10 cm, less than 5 cm, or less than 1 cm.

Figure 5A:
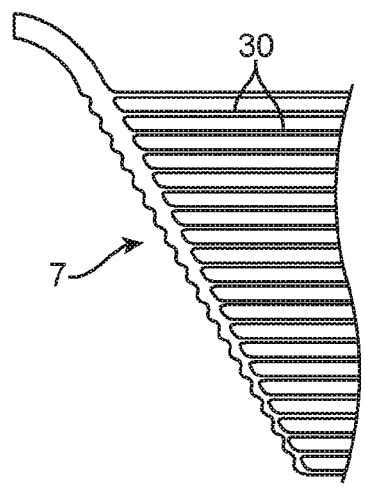
FIGS. 5A and 5B depict another embodiment of an inlet manifold of a hemofilter.
Figure 5B:
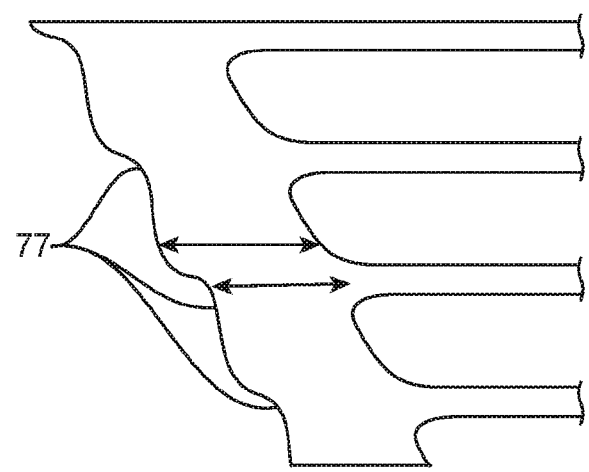

FIGS. 5A-5B provide an alternate design of a hemofilter manifold. FIG. 5A shows a tapering conduit 7 having regularly placed indents 77 that decrease the cross-sectional area of the conduit at the entrance to each of the filtration channels. FIG. 5B shows a zoomed in schematic of the decrease in the cross-sectional, as depicted by the double headed arrows.

Figure 6:
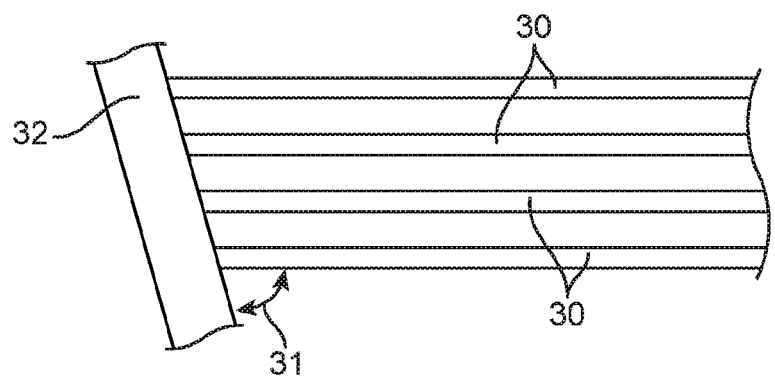
FIG. 6 shows a schematic of a hemofilter with an inlet manifold connected with multiple substantially parallel conduits.

FIG. 6 shows a schematic of hemofilter inlet manifold connected to a plurality of channels arranged in a spaced apart, parallel stacked configuration. The second region 32 of the extended inlet manifold is slanted relative to the longitudinal length of the filtration channels 30 at an angle 31 that is less than 90 degree and greater than 45 degree.

Figure 7A:
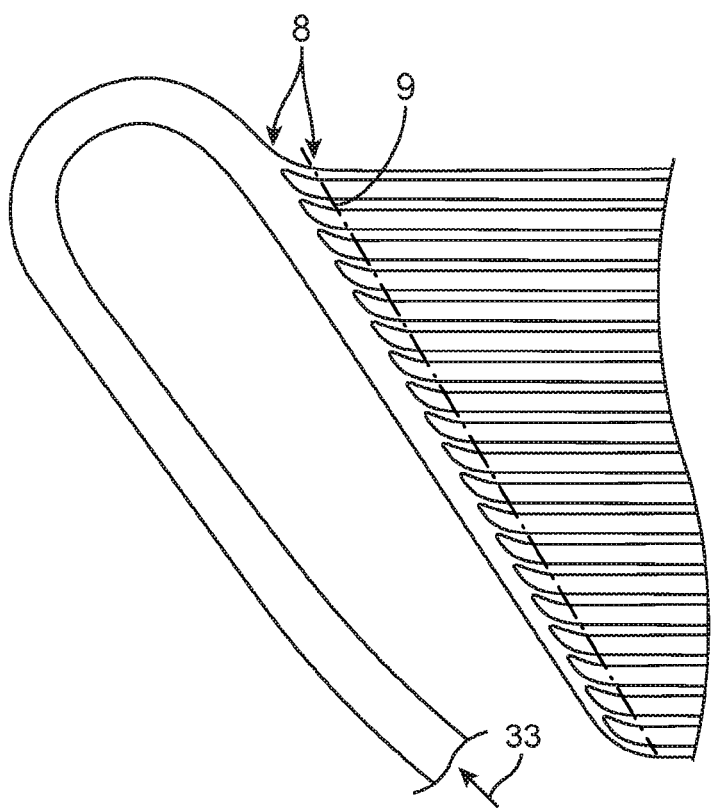
FIGS. 7A and 7B depict an embodiment of a hemofilter inlet manifold.
Figure 7B:
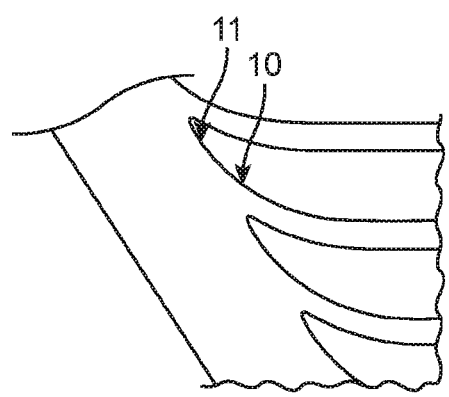

FIGS. 7A-7B depict a partial view of an extended inlet manifold depicting a tapered section connected to a plurality of filtration channels that are arranged in a parallel stacked configuration. A first curved region 8 of the plurality of filtration channels is indicated. A linear broken line 9 is included to illustrate the end of the curved section and beginning of the planar section of the filtration channels. FIG. 7B illustrates a zoomed-in image of the curved conduit section at the inlet of the plurality of filtration channels. FIG. 7B, shows transitional curved flow conduits 10 providing a guide flow between the inlet manifold and parallel channels, where the top surface of the curved region 10 is at a tangent to the inner surface 11 of the inlet manifold.

Figure 8:
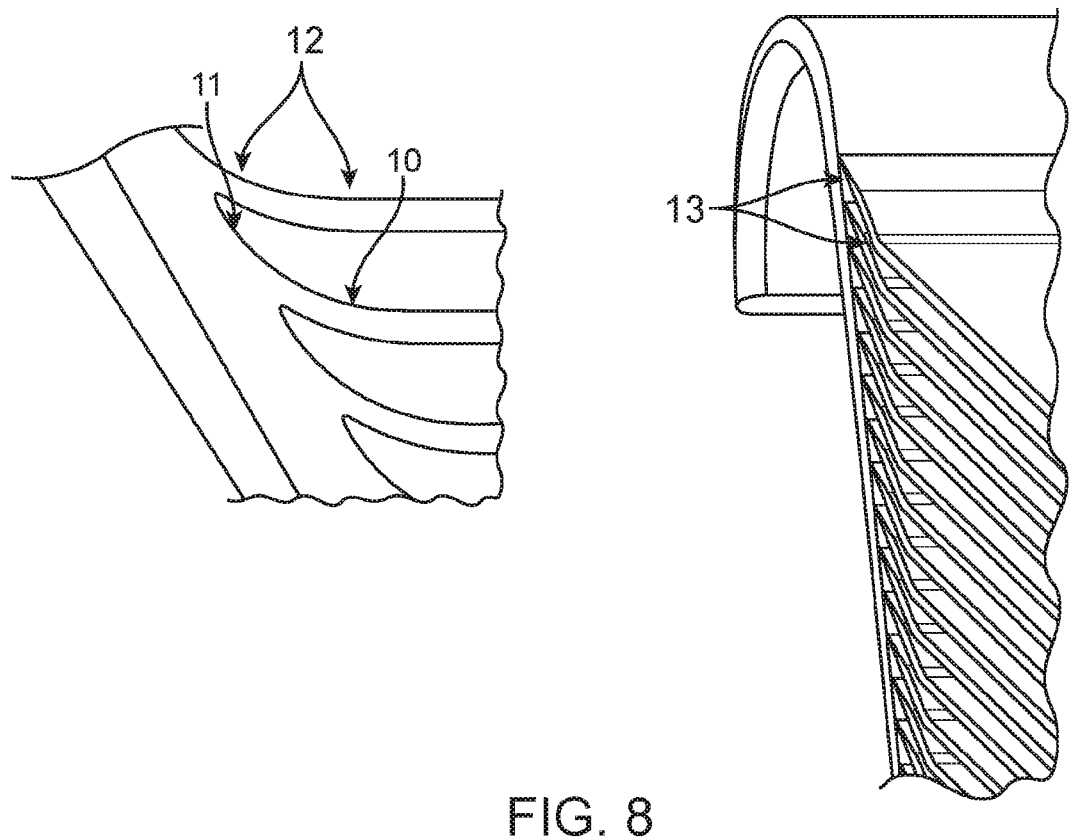
FIG. 8 provides different angle views of a hemofilter with an inlet manifold connected with multiple substantially parallel conduits.

FIG. 8 depicts the height of curved transitional region 12 of the first curved section of the plurality of the filtration channels. The length 13 of the first curved section of the plurality of the filtration channels is also depicted. As noted herein, in some embodiments, height of the curved region can be in the range between 0.2 mm and 1.8 mm and the height of the channel may expand to a height in the range between 0.25 mm and 2 mm over the length of the filtration channel. In some embodiments, the height of the curved transitional region may increase from the inlet toward the filtration section of the channels. In some embodiments, the width of the curved transitional flow conduit may vary over the length. In such embodiments, the width varies from a value range between 8 mm and 50 mm at the entry to a value range between 7 mm and 40 mm over the length.

Figure 9:
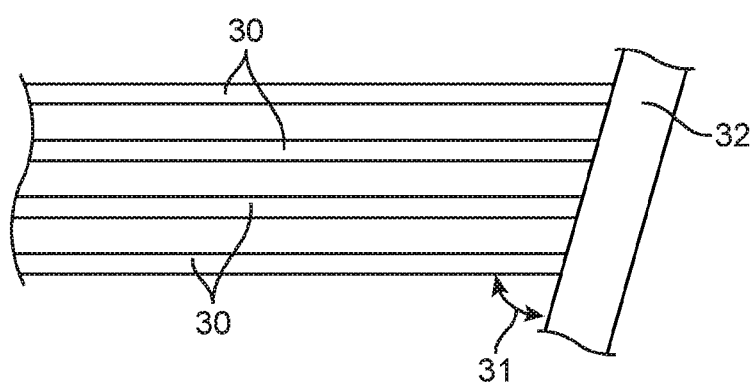
FIG. 9 shows a schematic of hemofilter with multiple substantially parallel conduits connected to an outlet manifold.

FIG. 9 shows a schematic of hemofilter with extended inlet manifold and a parallel-plate arrangement of the filtration channels according to embodiments of the present invention. Specifically, FIG. 9 shows an inlet manifold conduit 32 and a plurality of parallel conduits or channels 30 at an angle of orientation 31 relative to inlet manifold conduit 32. The orientation of the hemofilter is flipped compared to the orientation depicted in FIG. 6.

Figure 10:
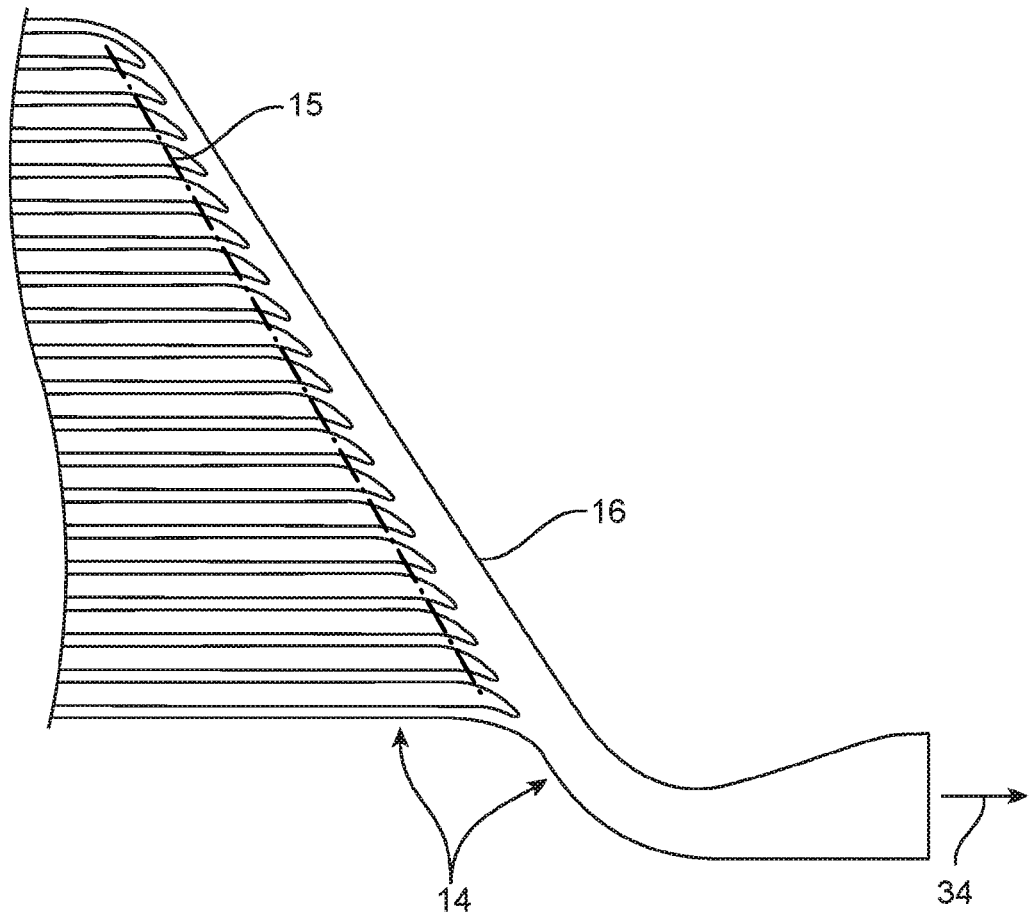
FIG. 10 provides a hemofilter with an outlet manifold connected with multiple substantially parallel conduits (connected to an inlet manifold).

FIG. 10 provides a view of the outlet manifold of a hemofilter in accordance to the embodiments of the present invention. FIG. 10 depicts a configuration where blood is delivered from the multiple parallel plate channels with a rectangular cross-sectional geometry with a curved section 14 that connects to the outlet manifold. The dashed lines 15 demarcated the end of the linear section of the filtration channel and the start of the curved section. Additionally, FIG. 10 shows a tapered outlet manifold 16, where the cross-sectional area of the manifold increases over the length. The height of the outlet manifold conduit 16 increases from an initial height of between 0.25 mm and 2 mm to a final height between 1 mm and 10 mm. The height of the outlet manifold conduit increases with the square root of volumetric flow rate as described in Equation 1. Height of the manifold conduit may also increase linearly with a local volumetric flow rate as described in Equation 2.

Figure 11:
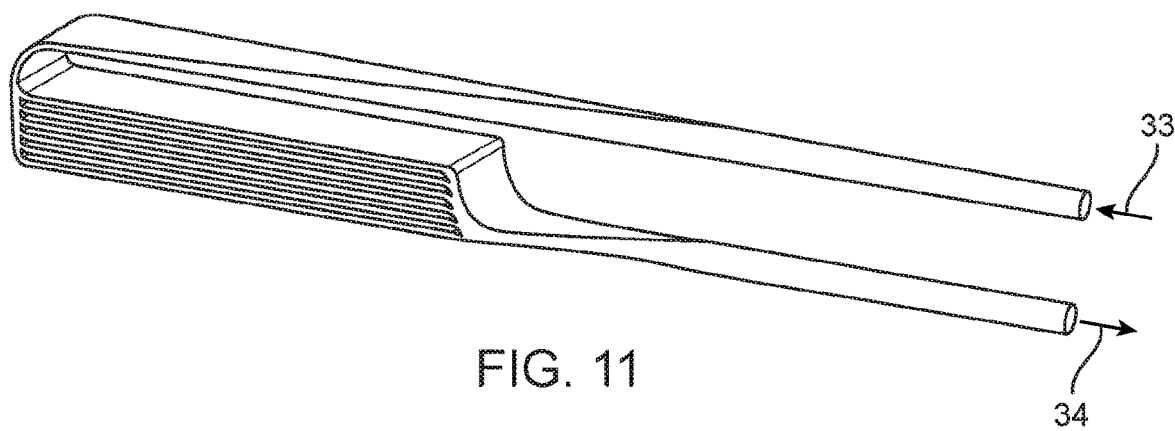
FIG. 11 illustrates an embodiment of a hemofilter as disclosed herein.

FIG. 11 provides a hemofilter in accordance to the embodiments of the present invention. Specifically, the hemofilter of FIG. 11 depicts an inlet 33, an outlet 34 and six filtration sections between the inlet and outlet.

Figure 12:
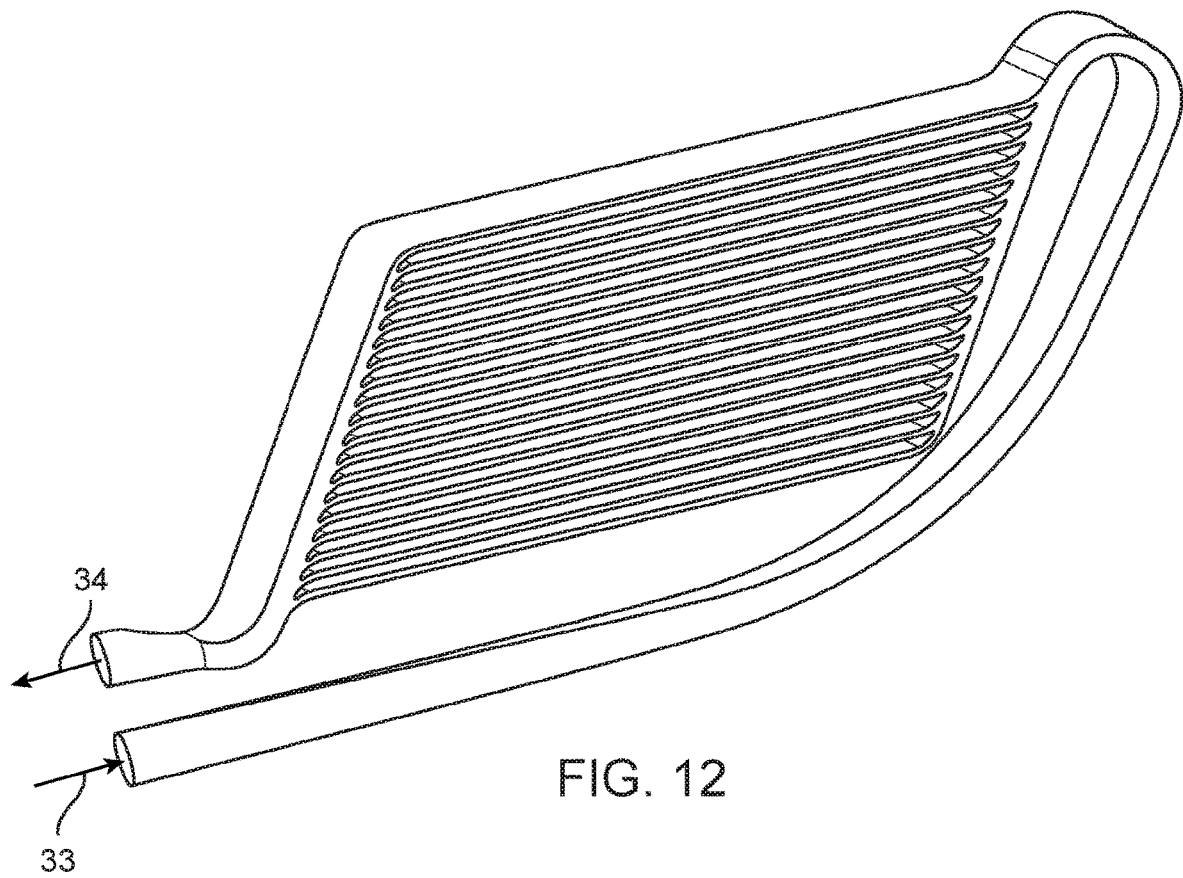
FIG. 12 illustrates an embodiment of a hemofilter as disclosed herein.

FIG. 12 provides a hemofilter in accordance to the embodiments of the present invention. Specifically, the hemofilter of FIG. 12 depicts an extended inlet manifold with opening 33, an outlet manifold with opening 34, and twenty filtration channels between the inlet and the outlet. The channels of the plurality of channels have a length of 65 mm, a height of 0.5 mm, and a width of 30 mm.

Figure 13:
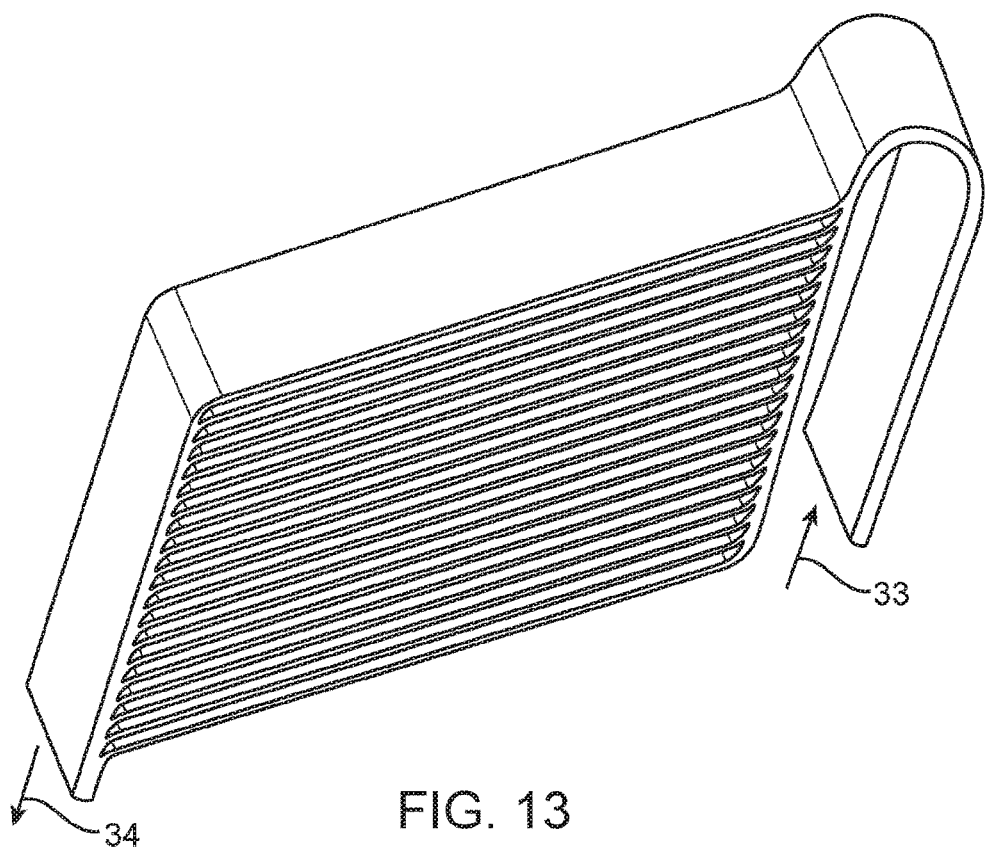
FIG. 13 illustrates an embodiment of a hemofilter as disclosed herein.

FIG. 13 provides a hemofilter in accordance to the embodiments of the present invention. Specifically, the hemofilter of FIG. 13 depicts a part of the extended inlet manifold with opening 33, an outlet manifold with opening 34 and twenty channels between inlet and outlet manifolds.

Figure 14:
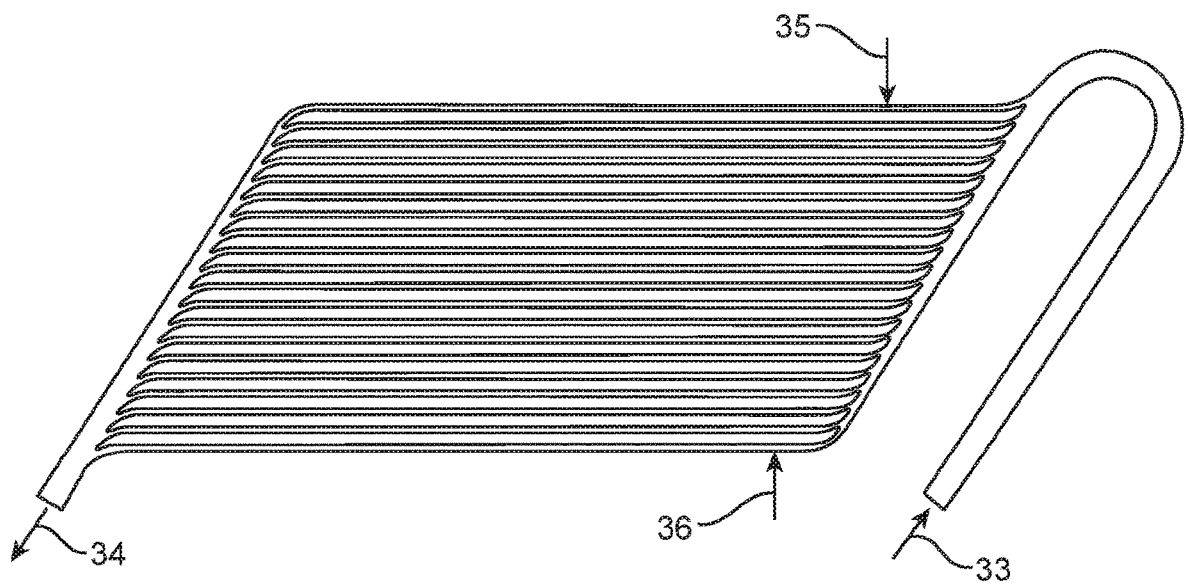
FIG. 14 provides a different view of the hemofilter depicted FIG. 13.

FIG. 14 provides a side view of the hemofilter of FIG. 13, illustrating a first (top) channel 35 and the last (bottom) channel 36.

FIGS. 15-17, and 19-23 provide CFD modeling of the hemofilter with the extended inlet in accordance to the embodiments of the present invention, illustrating transient simulations, laminar flow, and varying boundary conditions. Parameters of the CFD modeling for FIGS. 1-22 include laminar flow with a low Reynolds number flow. Inlet conduit parameters include a physiology-based pulsatile flow rate with a mean flow rate of 750 ml/min for the full hemofilter device, and a maximum flow rate of 827 ml/min for the full hemofilter device. Outlet parameters include an average static pressure of 0 mmHg. Additionally, CFD modeling was applied with parameters representing non-Newtonian blood at 37° C. using a cross-non-Newtonian viscosity model at a density of 1060 kg/m$^3$. The cross-non-Newtonian viscosity model included an infinite shear limit of 3.5 cps and a zero shear limit of 56.0 centipoise (cps). The CFD modeling of the hemofilter with the extended inlet in accordance to the embodiments of the present invention showed good distribution of flow amongst the channels (−10.8% to +5.5%), where the initial top five channels 1-5 had the lowest volumetric flow rates. Additionally, few areas in the hemofilter device had sustained low shear stress, specifically at the inlet diffuser and the entrance and exit from the channels. Lastly, the hemofilter device had a low pressure drop of 6 mmHg at a maximum flow rate of 827 ml/min, which helps maintain arterial driving pressure for ultra-filtration.

Figure 15:
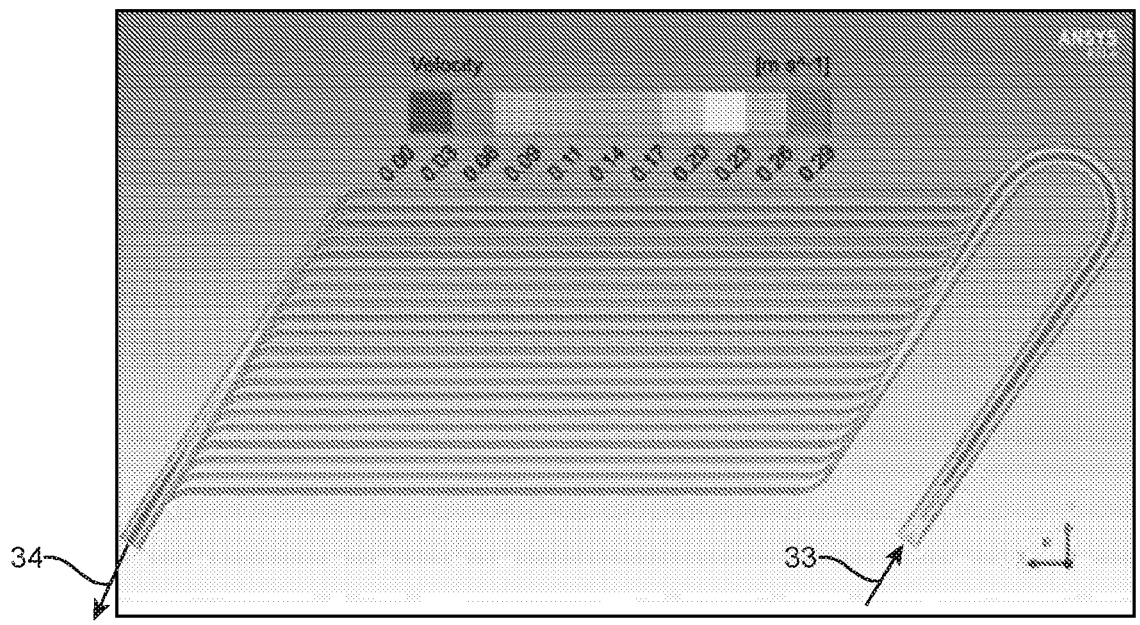
FIG. 15 illustrates the speed contours of blood on an XY-symmetry plane, showing a smooth transition from inlet to the inlet manifold to multiple conduits to outlet manifold and to outlet of a hemofilter.

FIG. 15 illustrates the speed contours of blood on an XY-symmetry plane, showing a smooth transition from inlet and outlet conduits to the flow channels. Inlet conduit shows an initial high fluid velocity in the range of 0.26-0.29 m/sec at the entrance of inlet conduit and decreases to a range of 0.03-0.09 m/sec as it flows to the end of inlet conduit and into the flow channels. Outlet conduit shows a fluid velocity in the range of 0.26-0.29 m/sec along the center of outlet conduit and decreases as blood flows into the channels.

Figure 16:
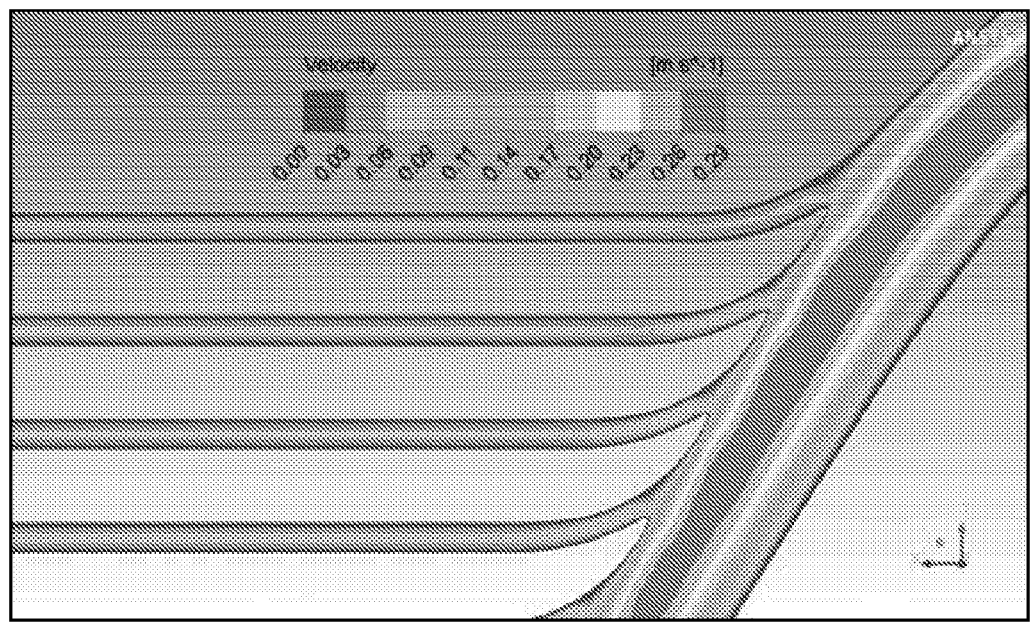
FIG. 16 provides a zoomed in image of FIG. 15.

FIG. 16 provides a zoomed in image of FIG. 15. The arrows in FIG. 16 illustrate lower speed regions and lower wall shear stress regions along top walls entering the channels.

Figure 17:
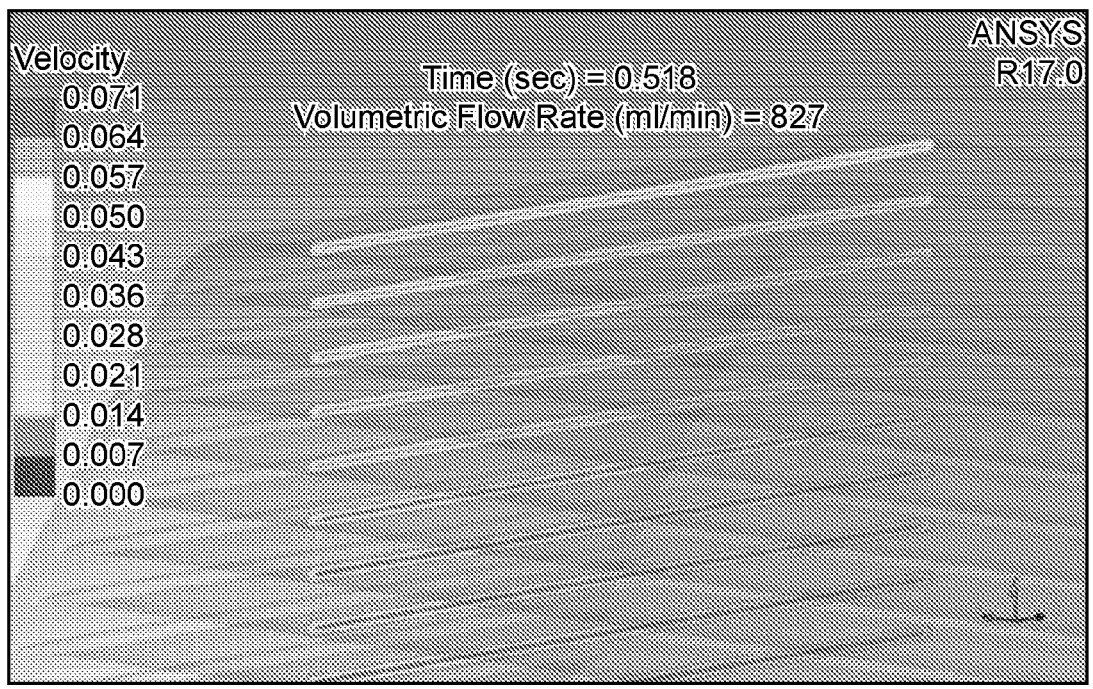
FIG. 17 provides an illustration of the flow velocity in the multiple conduits/channels.

FIG. 17 provides an illustration of the flow velocity in the channels at the maximum volumetric flow rate of 827 ml/min (0.518 seconds time step), showing good flow uniformity amongst channels, with slower flow velocities through the top 5 channels.

Figure 18:
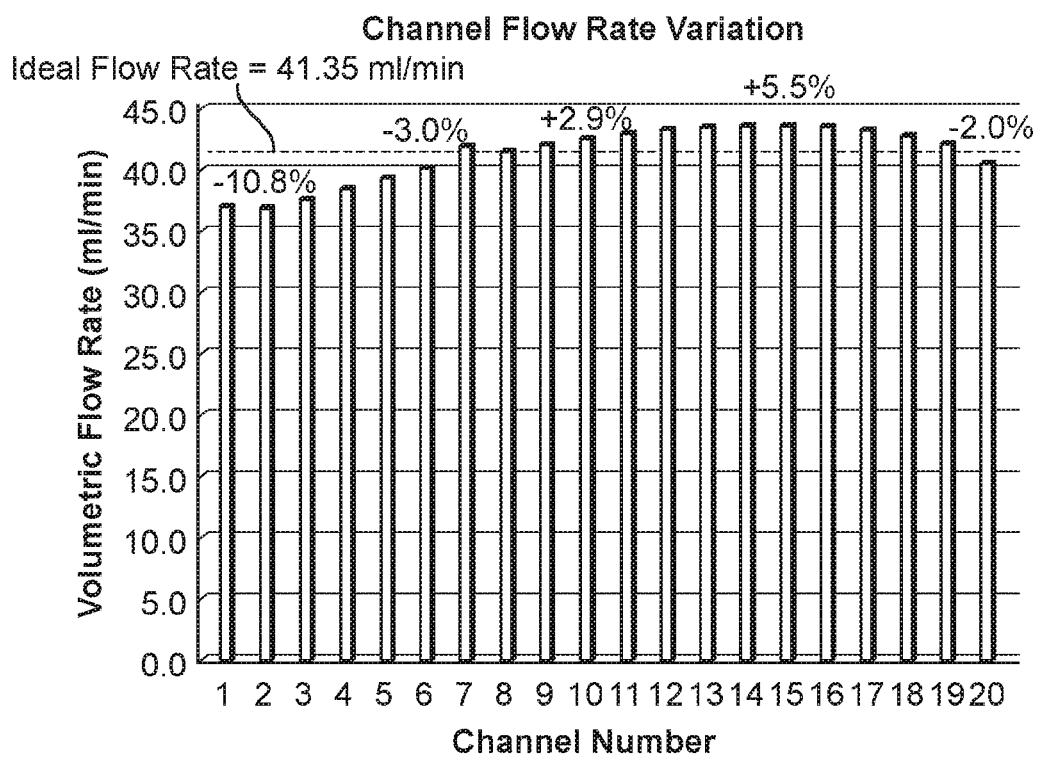
FIG. 18 provides a bar graph of a hemofilter of FIG. 17, showing flow rate (ml/min) variation in each channel.

FIG. 18 provides a bar graph for volumetric flow rate variation in each channel in a hemofilter comprising 20 parallel channels extending from the second region of the extended inlet manifold. The data shows overall good uniformity of flow amongst channels, with lower flow rates in channels 1-5 (top channels nearest the incoming flow).

Figure 19:
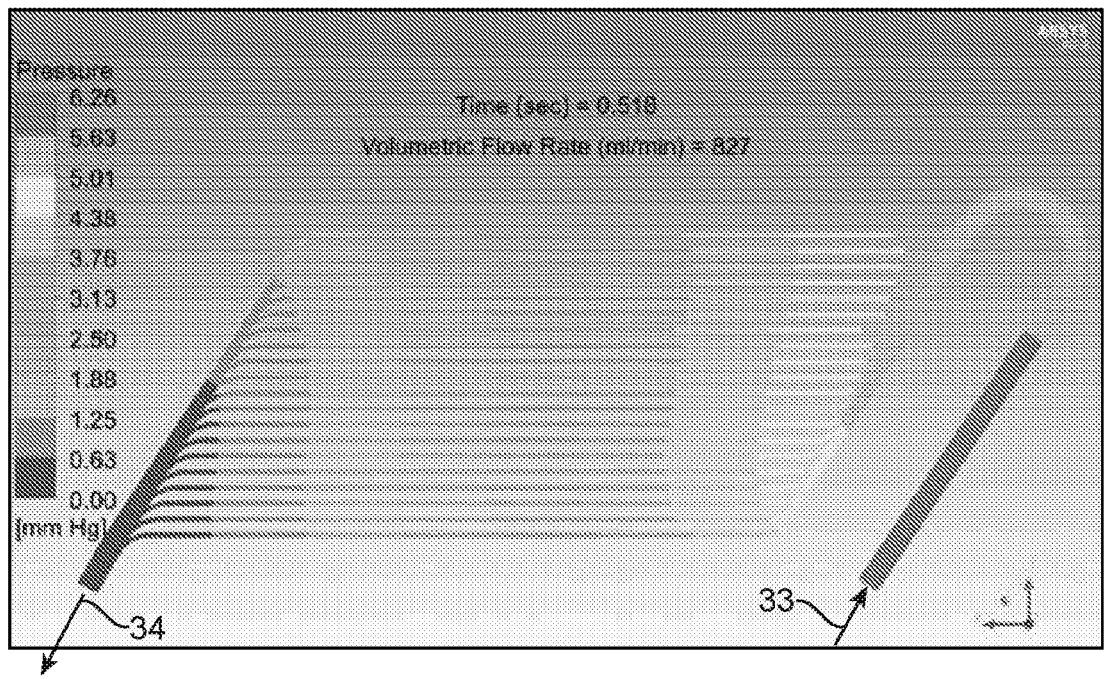
FIG. 19 provides an illustration of the static pressure contours in a hemofilter provided herein.

FIG. 19 provides an illustration of the static pressure contours in the hemofilter device. The volumetric flow rate tested was 827 ml/min, at 0.518 seconds, showing high pressure between 5.63-6.26 mmHg in the inlet conduit and lower pressures between about 1.70-0 mmHg in the outlet conduit.

Figure 20:
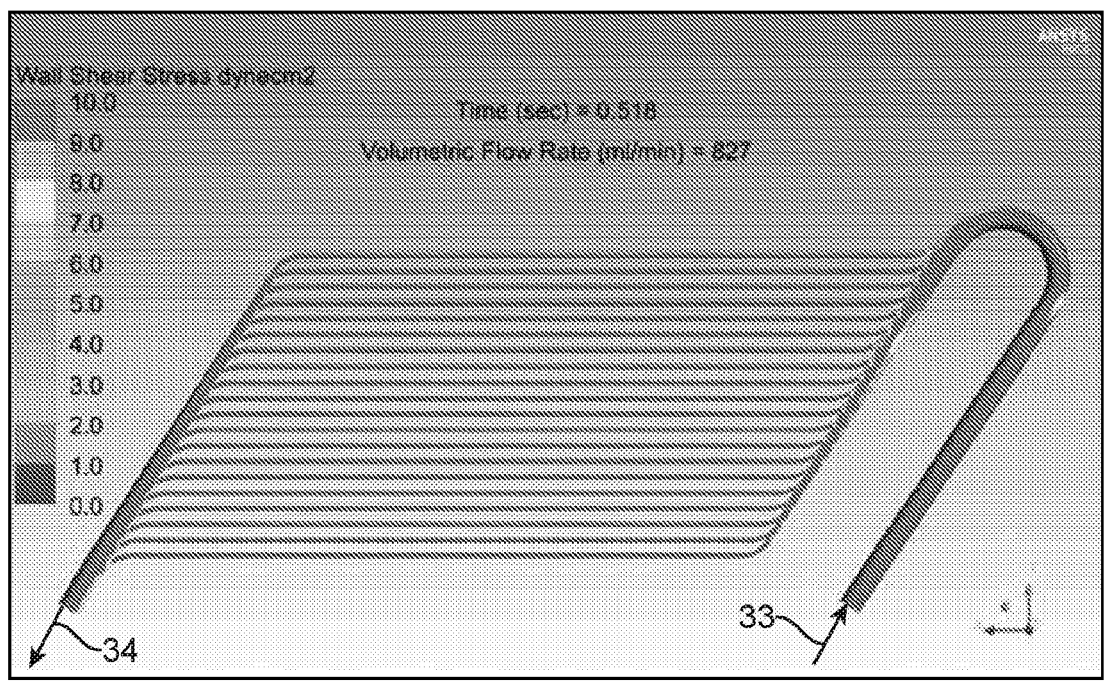
FIG. 20 provides an illustration of the wall shear stress in a hemofilter described herein.

FIG. 20 shows regions of lower wall shear stress in the hemofilter device. Channel walls have a wall shear stress at least 10 dyne/cm$^2$. Additionally, the regions at the entrance and exit of the channels have an even lower shear stress of about 8 dyne/cm$^2$.

Figure 21:
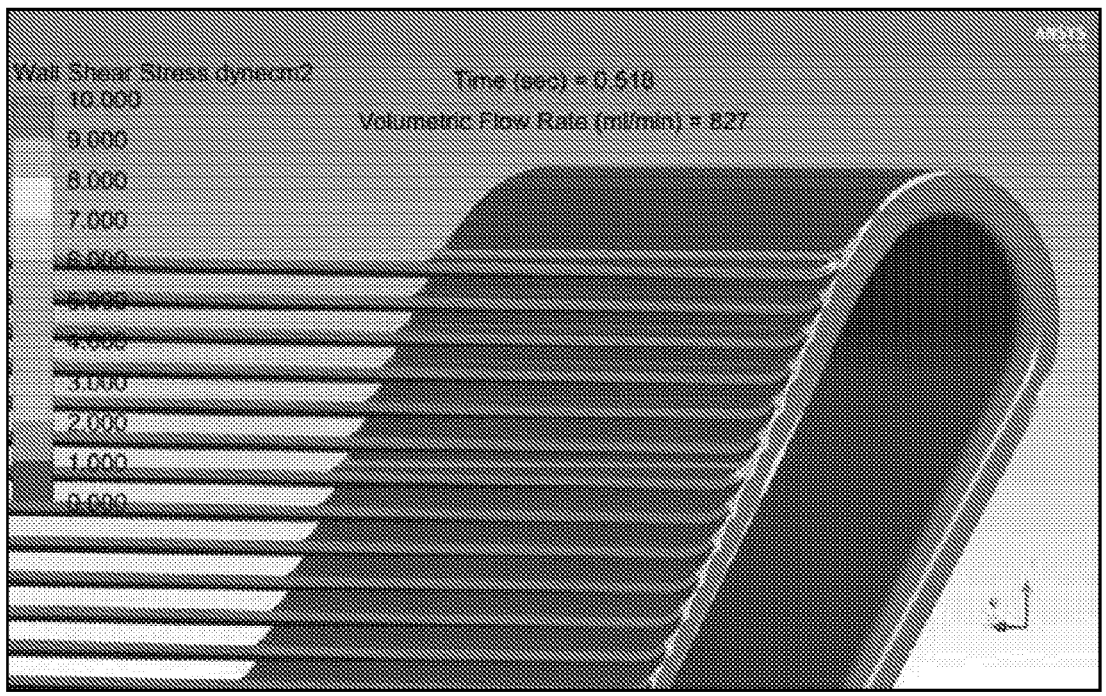
FIG. 21 provides an illustration of the wall shear stress at the transition from inlet manifold to the parallel conduits in a hemofilter.

FIG. 21 provides an illustration of the low wall shear stress regions in the hemofilter. The channel walls have a wall shear stress of at least 10 dyne/cm$^2$ and areas of low shear stress are present at the entrance and exit of the channels, and very small areas of low shear (0-7 dyne/cm$^2$) at the entrance of the channels.

Figure 22:
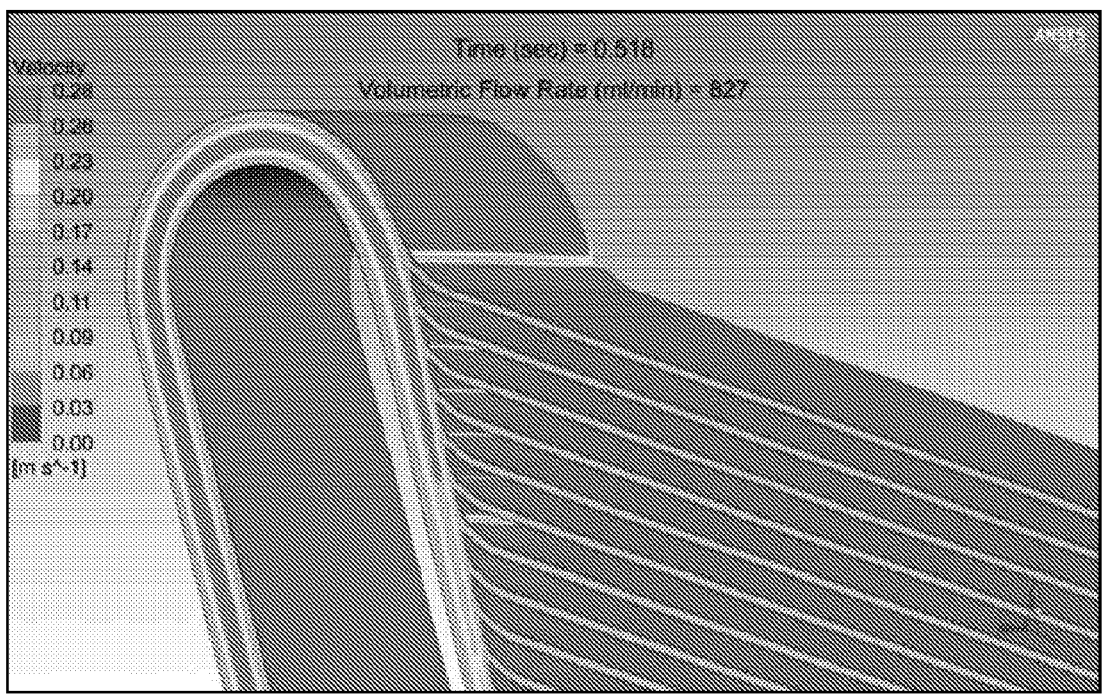
FIG. 22 provides an illustration of the blood velocity along an XY-symmetry plane and wall shear stress in a hemofilter device described herein.

FIG. 22 provides an illustration of blood velocity in the hemofilter. The blood velocity varies at the walls of the channels and conduits compared to the central area away from the walls. The flow rate ranges from 0.06 m/sec-0.28 m/sec in the inlet manifold and slows to a range of 0.03 m/sec-0.09 m/sec in the plurality of channels. This image also shows regions of low wall shear stress on the hemofilter walls.

Figure 23:
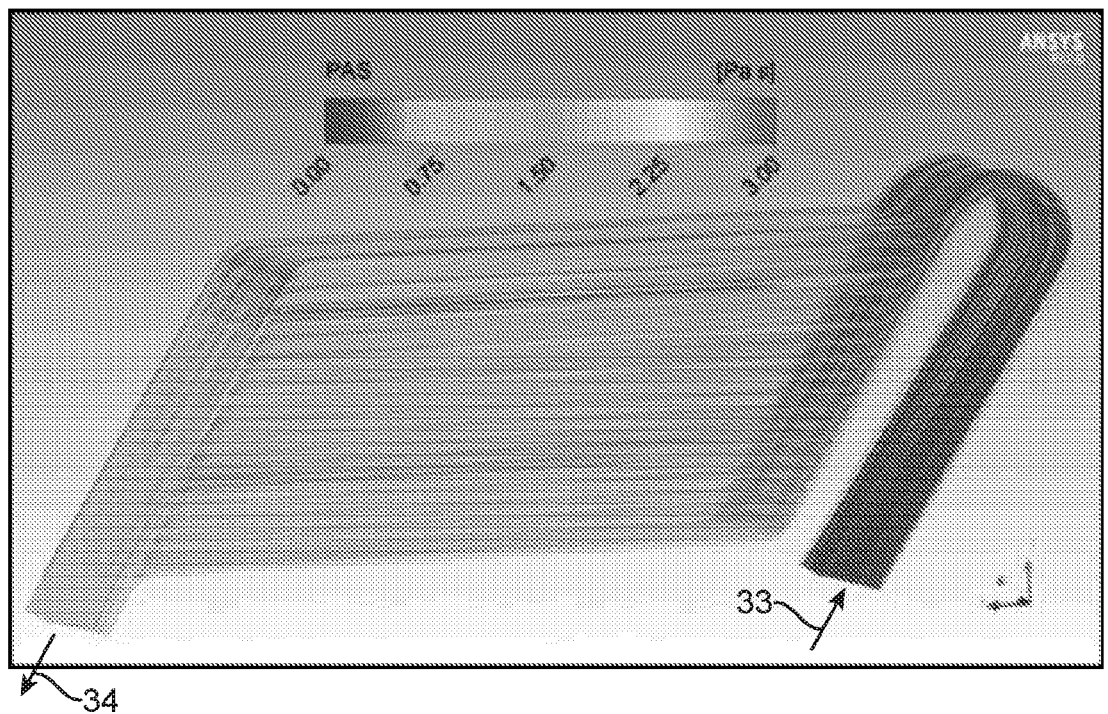
FIG. 23 provides an illustration of the platelet stress accumulation (PSA) along particle paths in a hemofilter device, where the highest PSA is present along the corners and near the walls in regions of the hemofilter where flow rate is lowest.

FIG. 23 provides an illustration of the platelet stress accumulation (PSA) along particle paths in the hemofilter device, where the highest PSA was shown along the corners and near the walls in the slowest moving regions of the hemofilter. The upper limit of the PSA range was limited to 3 Pa*sec to visualize the variations. The CFD model input parameters for the steady state simulations included laminar flow with a low Reynolds number flow; particle tracking with 3 mm diameter platelet particles, neutrally buoyant particles, and a two-way couple particle/flow field model; boundary conditions included an inlet flow rate of 827 ml/min (maximum flow rate), and an outlet average static pressure of 0 mmHg; and non-Newtonian blood at 37° C. using a cross non-Newtonian viscosity model and a density of 1060 kg/m3. The cross-non-Newtonian viscosity model included an infinite shear limit of 3.5 cps, and a zero shear limit of 56.0 cps.

Hemofilters with Serpentine Filtration Channel

Embodiments of the hemofilters provided herein include an extended inlet conduit, a single serpentine filtration channel, and an outlet conduit. The extended inlet conduit may include a first region having an opening having a substantially circular cross section geometry configured for connection to a blood vessel of an individual into whom the in vivo filtration device is implanted. The first region of the extended inlet conduit may also include a transition region in which the circular opening transitions into a substantially rectangular cross section in order to guide the blood flow into the substantially rectangular cross section region. As such, the space enclosed by the extended inlet conduit transitions from having a circular cross-section into a substantially rectangular cross-section. The second region of the extended inlet conduit starts at the point where the transition into the substantially rectangular cross section is complete and at which point, along the extended inlet conduit, the cross section area is constant. The second region of the extended inlet conduit includes a curved region having the substantially rectangular cross section. The curved section of the inlet conduit is connected to a serpentine filtration channel that includes linear sections connected by turnarounds such that the direction of flow of blood in the linear sections reverses at each adjacent linear section connected by a turnaround section. In some embodiments, the curved section of the inlet conduit may lead into a substantially planar section of the first filtration section of the serpentine channel. In some embodiments, the curved section of the inlet may include a U-shaped curve, providing a turnaround section similar to those in the serpentine channel, see e.g., FIG. 24. In other embodiments, the curved section of the inlet conduit connected to a linear section of the serpentine channel may include a curve that connects the inlet to the first filtration section of the serpentine channel at an angle of about 90 degree, see e.g., FIG. 25.

Figure 76A:
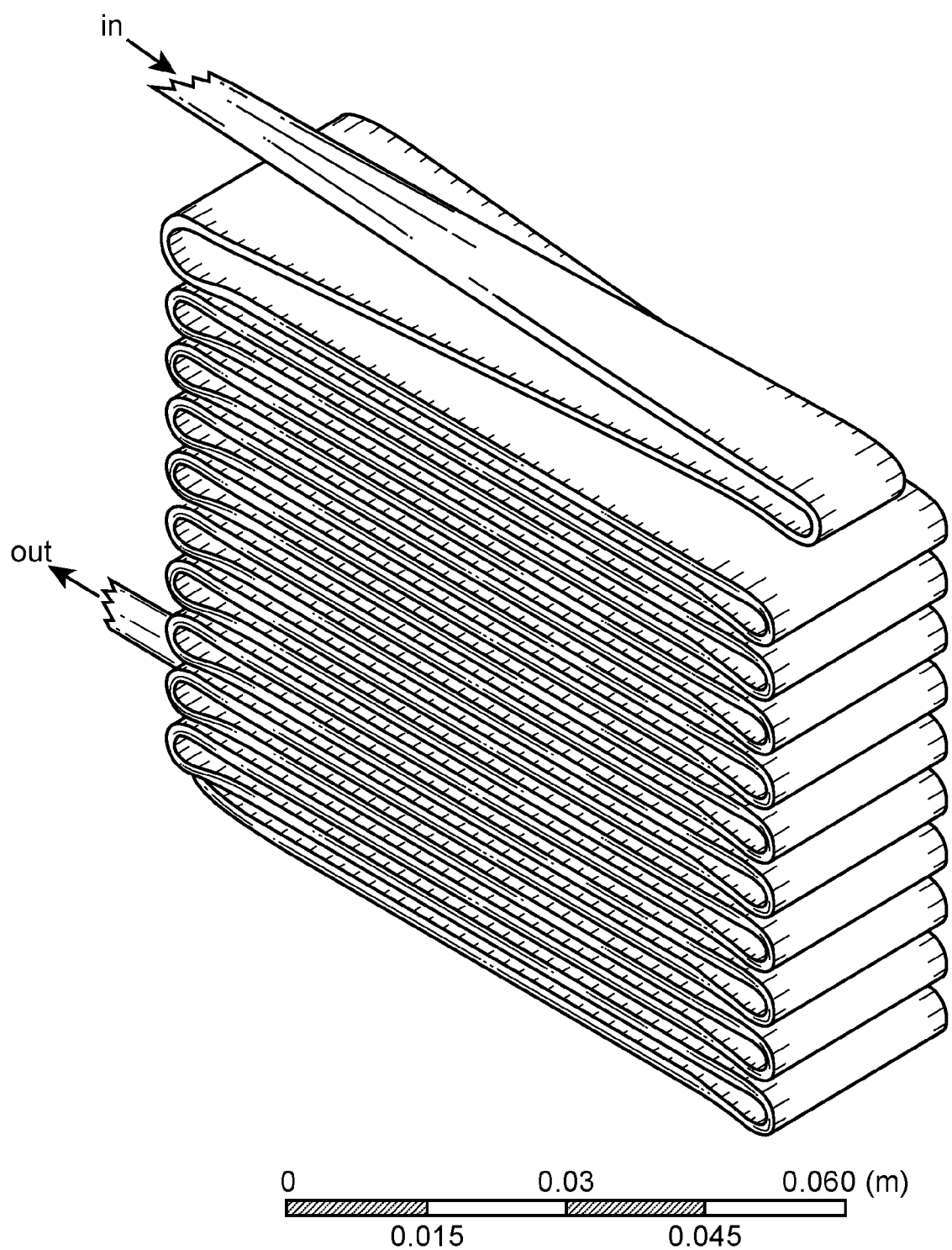
FIGS. 76A and 76B provide an illustration of the hemofilter comprising an extended inlet conduit with two turnaround sections, an outlet conduit, and serpentine flow channel between inlet and outlet conduits.
Figure 76B:
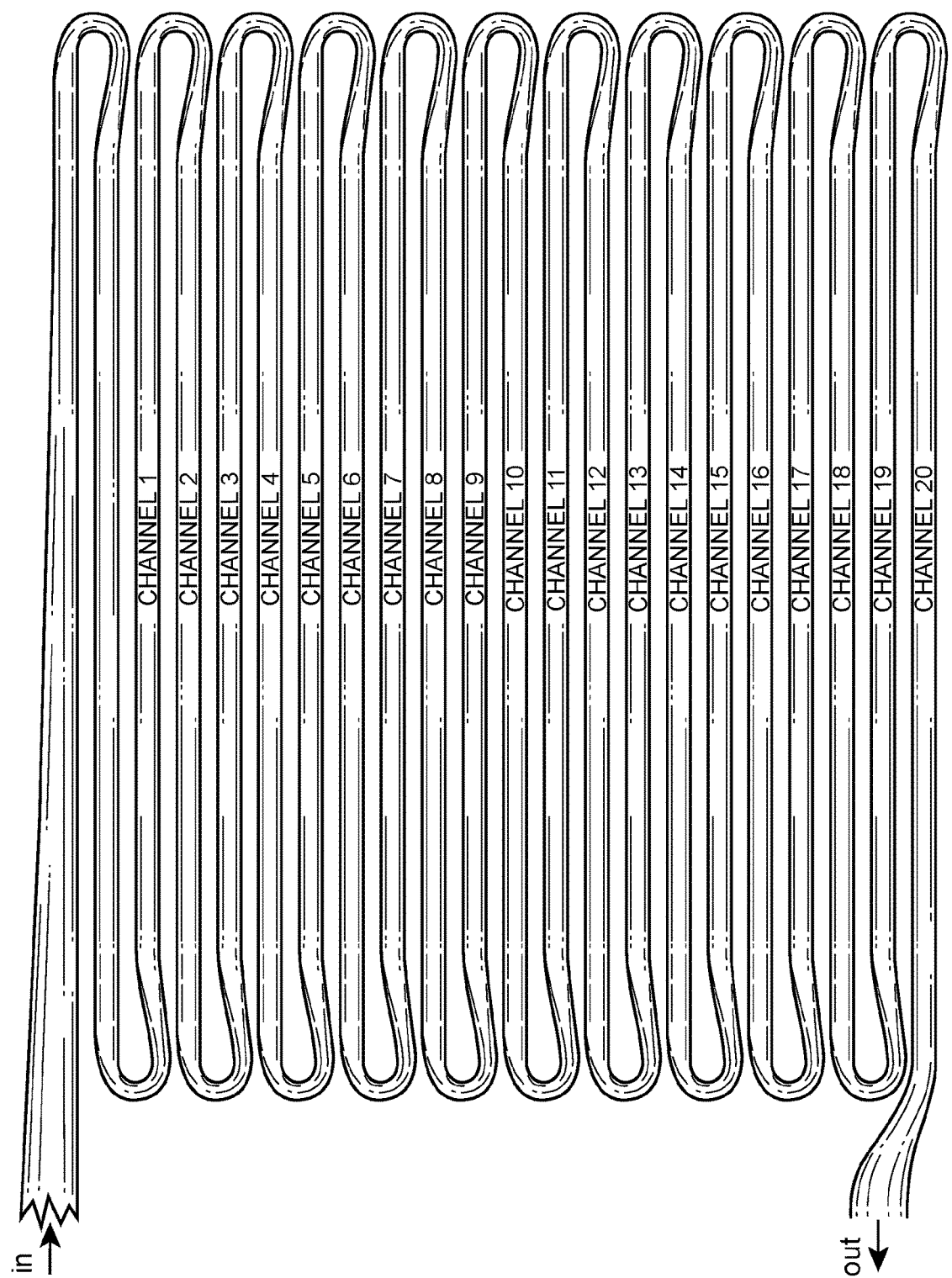

In certain embodiments, a hemofilter having a serpentine filtration channel may have an extended inlet with two turnaround sections. The extended inlet may include a first transition region separated from a second transition region by a first turnaround section. The second transition region may terminate in a second turnaround section connected to a substantially planar section of the first filtration section of the serpentine channel. The first transition region may have a circulate opening for connecting to a blood vessel, which circular opening flattens in height and expands in width to produce a substantially rectangular shape which is connected to the second transition region via the first turnaround section. The lumen of the inlet in the second transition region increases in cross sectional area by expansion of width of the lumen and terminates in the second turnaround such that the dimensions of the cross-section of the lumen of the inlet at the end of the second transition region and the second turnaround section are substantially the same and such that the cross sectional dimension of the lumen of the second turnaround area matches that of the filtration sections of the serpentine channel. A hemofilter with an extended inlet with two turnaround sections of different size is depicted in FIGS. 76A and 76B. Cross section area here refers to the area of the interior of the conduit, i.e., lumen of the conduit.

The serpentine channel may have a substantially rectangular cross section through which blood flows in the channel and may include a first linear section followed by a first turnaround, followed by a second linear section, followed by a second turnaround and so forth and the last linear section or the last turnaround may be connected to an outlet having a first region that is substantially rectangular and a second region that transitions from rectangular to a circular cross section to terminate in a circular outlet configured for connection to a blood vessel of the individual. The linear sections of the serpentine channel may be in a stacked spaced-apart arrangement and may be substantially parallel to each other.

Figure 25:
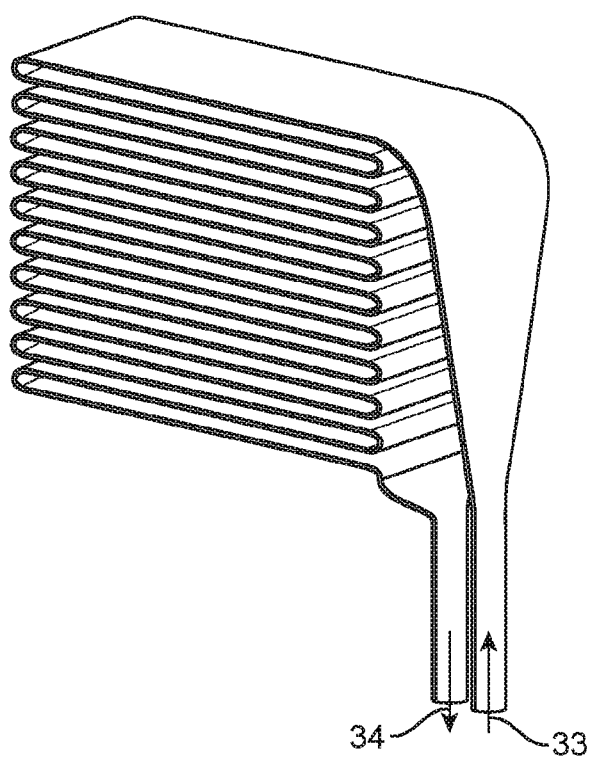
FIG. 25 illustrates a hemofilter device with an extended serpentine flow channel and an extended inlet.

One or more curves or turns may be included in the inlet and the outlet conduits to provide a hemofilter in which the inlet and outlet openings are placed adjacent to each other to facilitate connecting the in vivo filtration device to the blood vessels of the individual, for example, for connecting the in vivo filtration device comprising the hemofilter with adjacent inlet and outlet openings to an artery and a vein, respectively, of the individual, see, e.g., FIG. 25.

The dimensions of the inlet opening, outlet opening, and rectangular cross section areas may be as provided for the hemofilter with extended inlet manifold in the preceding section. For example, the diameter of the inlet may range from 3 mm-8 mm and may be selected based upon the blood vessel to which the in vivo filtration device will be connected. In certain embodiments, the diameter of the inlet may range from 3 mm-7 mm, 3 mm-6 mm, 3 mm-5 mm, 4 mm-7 mm, or 4 mm-6 mm. The inlet may be grafted (e.g., sewed) directly to a blood vessel or may be connected to a biocompatible tubing that in turn is grafted to a blood vessel.

The dimensions of the substantially rectangular cross section region of the inlet conduit at the first region may be about 2 mm-8 mm height and 5 mm-10 mm in width (transitioning from a diameter of 3 mm-8 mm, respectively) and may transition to a substantially rectangular cross section having a dimension at the start of the second region ranging from 7 mm-50 mm in width and 0.5 mm-8 mm height. In certain embodiments, the diameter of the inlet may range from 4 mm-7 mm and the rectangular cross section at the start of the second region may range from 0.5 mm-3 mm height and 20 mm-50 mm width, e.g., 0.5 mm-2.5 mm height and 20 mm-40 mm width, 0.5 mm-2 mm height and 20 mm-35 mm width, 0.75 mm-2 mm height and 25 mm-35 mm width, or 1 mm-2 mm height and 25 mm-30 mm width.

The serpentine channel may have a width that substantially matches the width of the rectangular second region of the inlet conduit and the rectangular first region of the outlet conduit. In certain aspects, the height of the linear sections of the serpentine channel may be comparable to the height of the rectangular second region of the inlet conduit and the rectangular first region of the outlet conduit. For example, the linear section of the filtration channel may have a height in the range of 0.5 mm-5 mm (e.g., of 0.5 mm-4 mm, 1 mm-4 mm, 1 mm-3 mm, 1 mm-2 mm, 1.5 mm-2 mm, 1 mm-2 mm, or 0.5 mm-2 mm) and the width in the range of 8 mm-50 mm (e.g., 9 mm-50 mm, 10 mm-50 mm, 10 mm-40 mm, or 20 mm-40 mm). The length of the filtration channels can vary based on a number of factors, such as, the surface area of the membrane section in the filtration channels, the height and width of the channels as well as the number of channels. In certain embodiments, the length of each of the channel may be in the range of 40 mm-100 mm (e.g., 40 mm-90 mm, 40 mm-80 mm, 40 mm-70 mm, or 50 mm-70 mm). The portion of the filtration channels where a membrane forms the walls (e.g., top and bottom walls) of the channels may vary depending upon the dimensions and number of the linear sections of the channels. In certain embodiments, at least a quarter, at least a half, at least a two third, or more of the linear section of the channel is formed from a membrane. In certain embodiments, a surface area of between 0.016 and 0.16 square meters of the channel may be covered by a membrane. In certain embodiments, the linear sections of the serpentine channel may each have a membrane section providing a surface area of 0.0008 $m^2$-0.008 $m^2$ per linear section for filtration of blood flowing through the channel. In certain embodiments, the serpentine channel in the hemofilter may provide a filtration area (formed by the membrane) in the range of 0.016 $m^2$-0.16 $m^2$, e.g., 0.032 $m^2$-0.16 $m^2$, 0.064 $m^2$-0.16 $m^2$, 0.064 $m^2$-0.10 $m^2$, or 0.064 $m^2$-0.09 $m^2$. The number of repeats of the linear regions separated by the turnaround regions can be in the range of 10-40, such as, 10-35, 10-30, 15-40, or 15-30. As noted herein, the number of linear regions can be increased and at least one of length or width of the channel decreased or vice versa to achieve a target filtration surface area for the hemofilter.

In certain embodiments, the membrane portion of the linear sections of the serpentine channel may be affixed to the turnaround sections. In certain aspects, the membrane may be attached to a scaffold defining two side walls of the linear section of the channel and providing an open top and/or an open bottom which may be covered by the membrane to provide the filtration surface.

The flow of blood through the linear sections for filtration may be determined by the shape and angle of curvature of the turnaround sections and/or height of the turnaround sections. In a first aspect, the turnaround region may include a constriction at the beginning of the turnaround region where the height of the channel is reduced and an expansion at the end of the turnaround region at which the height of the channel returns to the height prior to start of the turnaround region. In this aspect, the rate of blood flow into the turnaround region is reduced by the constriction and increased by the expansion. In this aspect, optionally, the radius of curvature of the inner wall of the turnaround region may be constant or may increase from the beginning to the end of the turnaround region. The increase in the radius of curvature may result in the blood moving through the X-X plane that is lower than the X-X plane of the linear section and hence the blood moves from a lower plane to a slightly higher plane. In certain cases, the constriction may reduce the channel height by about 1%-50% and the expansion may restore the reduction in the height.

In certain aspects, the turnaround region may have an inner radius of curvature (defined by the inner wall of the turnaround region) equal to or greater than half the distance between the adjacent parallel linear filtration sections of the serpentine channel. R=C*S; where R equals the inner radius of curvature, C equals a constant value between 0.5 and 4, S equals the spacing between adjacent parallel linear filtration sections.

In another aspect, the rate of flow of blood in the serpentine channel may be controlled by varying height of the channel, where height of the channel may increase across the linear section of the channel and decrease around the turnaround section and increase again across the next linear section of the channel and so forth.

In another aspect, the rate of flow of blood in the serpentine channel may be controlled by the curvature of the turnaround section, where the turnaround section may include a canted turn at the start of the turnaround section followed by a smoother curvature at the end of the turnaround section. In such an aspect, the height of the channel at the turnaround section may remain the same or may increase, for example, the height of the channel at the start of the turnaround section may be higher compared to the height before and after the turnaround section.

Figure 24:
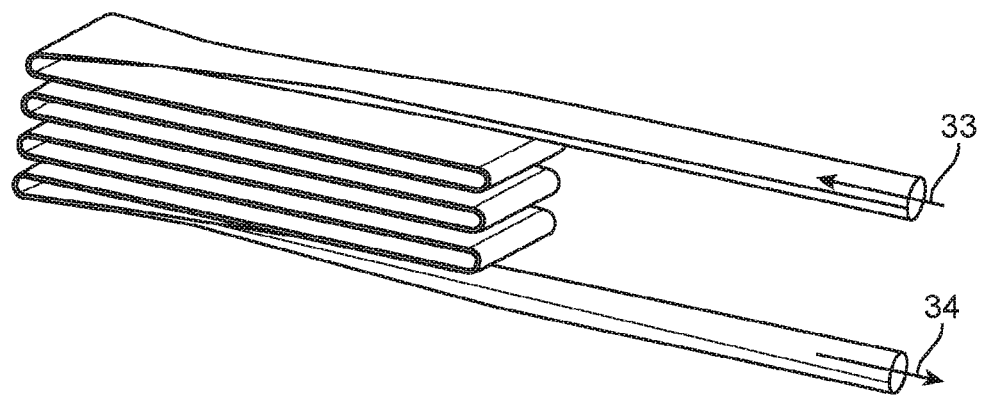
FIG. 24 provides an illustration of the hemofilter comprising an inlet conduit, an outlet conduit, and serpentine flow channel between inlet and outlet conduits.
Figure 75:
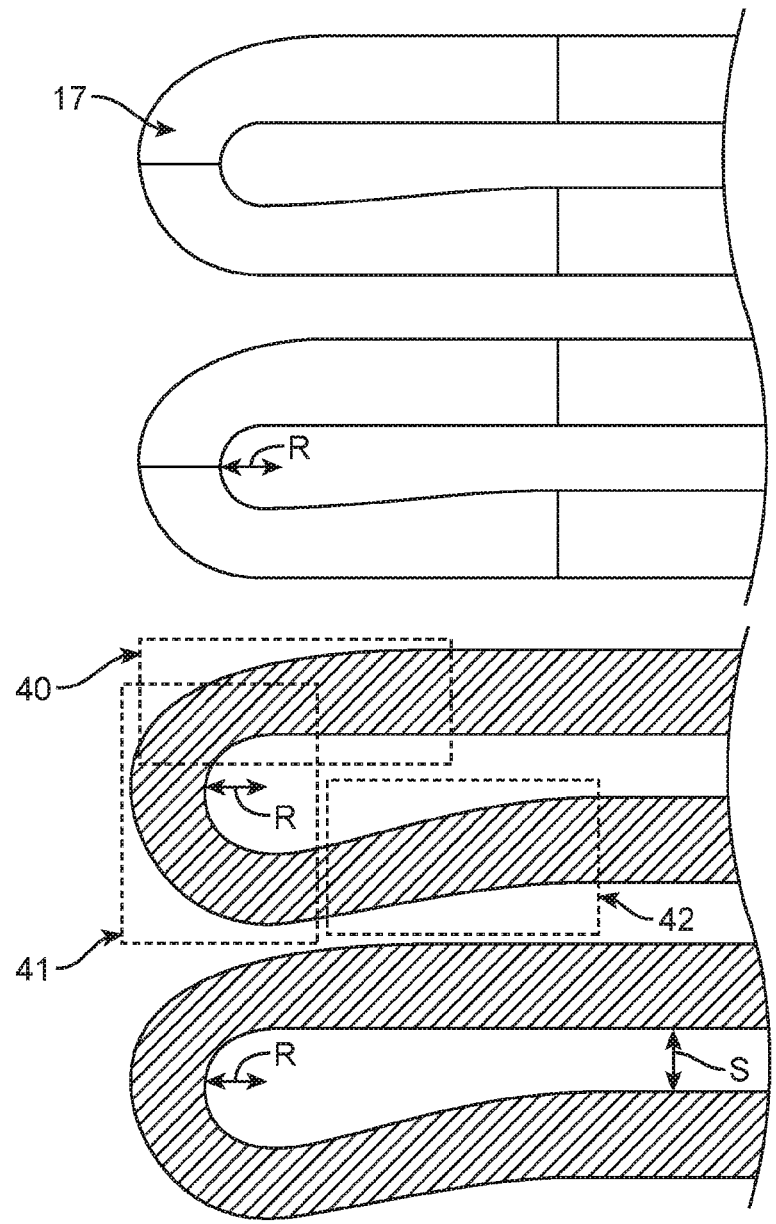
FIG. 75 illustrates regions of a serpentine channel of a hemofilter where the channel flow path shows varying geometric profiles (i.e., circular, elliptical, parabolic).

FIGS. 24-75 illustrate a hemofilter device comprising an extended inlet conduit, an outlet conduit, and serpentine flow channel between the inlet and outlet conduits.

CFD modeling of the hemofilter with serpentine channel, such as, those depicted in FIGS. 24-75 was performed to assess flow characteristics of blood flowing through the lumen of the hemofilter. Laminar flow was observed based on the CFD modeling. Inlet conduit parameters included a physiology-based pulsatile flow rate with a mean flow rate of 750 ml/min for the full hemofilter device, and a maximum flow rate of 827 ml/min for the full hemofilter device (CFD results). Outlet parameters included an average static pressure of 0 mmHg. Additionally, CFD modeling was applied with parameters representing non-newtonian blood at 37° C. using a cross-non-Newtonian viscosity model at a density of 1060 kg/m$^3$. The CFD modeling of the hemofilter with the serpentine channel showed good distribution of flow throughout the serpentine channel, where a refined turnaround geometry eliminated the low shear stress regions within the channel sections. The pressure drop of 88.5 mmHg was much higher than the extended inlet manifold (6 mmHg) of the hemofilter shown in FIGS. 1-23.

FIG. 24 provides an illustration of a hemofilter comprising an inlet conduit, an outlet conduit, and a serpentine flow channel between inlet and outlet conduits. FIG. 24 illustrates a hemofilter device with a serpentine flow channel having six filtration sections each with a height of 1 mm, a width of 30 mm, and a length of 65 mm. The inlet 33 and outlet 34 are circular. The inlet conduit includes a transition region in which the circular opening transitions into a substantially rectangular cross section. The rectangular cross section region includes a U-turn after which a filtration section of the channel begins.

FIG. 25 provides a hemofilter comprising an extended inlet conduit with a circular opening 33, an outlet conduit with a circular opening 34, and a serpentine channel having 20 rectangular filtration sections each having a height of 1.5 mm, a width of 30 mm, and a length of 65 mm. A first region of the extended inlet conduit includes a transition region in which the circular opening transitions into a substantially rectangular cross section. The second region of the extended inlet conduit starts at the point where the transition into the substantially rectangular cross section is complete and at which point, along the extended inlet conduit, the cross section area is constant. The second region of the extended inlet conduit includes a curved region having the substantially rectangular cross section. The curved section of the inlet conduit is connected to a serpentine filtration channel that includes linear sections connected by turnarounds such that the direction of flow of blood in the linear sections reverses at each adjacent linear section connected by a turnaround section. The curved section of the inlet conduit leads into a substantially planar section of the inlet conduit that connects to a turnaround section of the serpentine channel.

Figure 26:
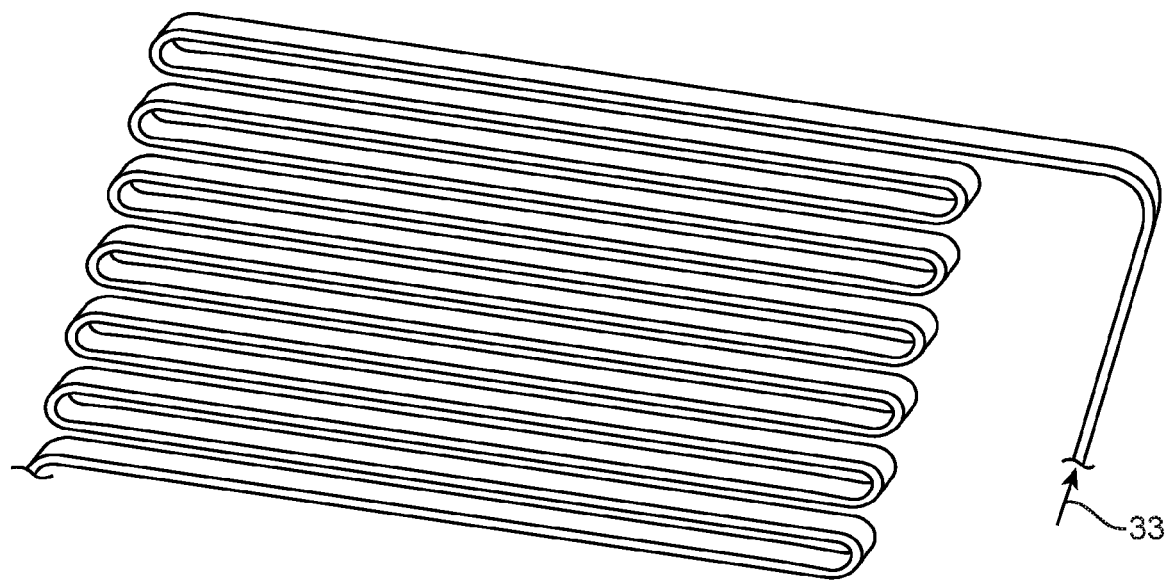
FIG. 26 provides a zoomed in view of the inlet and serpentine channel of FIG. 25.

FIG. 26 provides a zoomed-in view of the inlet conduit and serpentine channel of FIG. 25.

Figure 27:
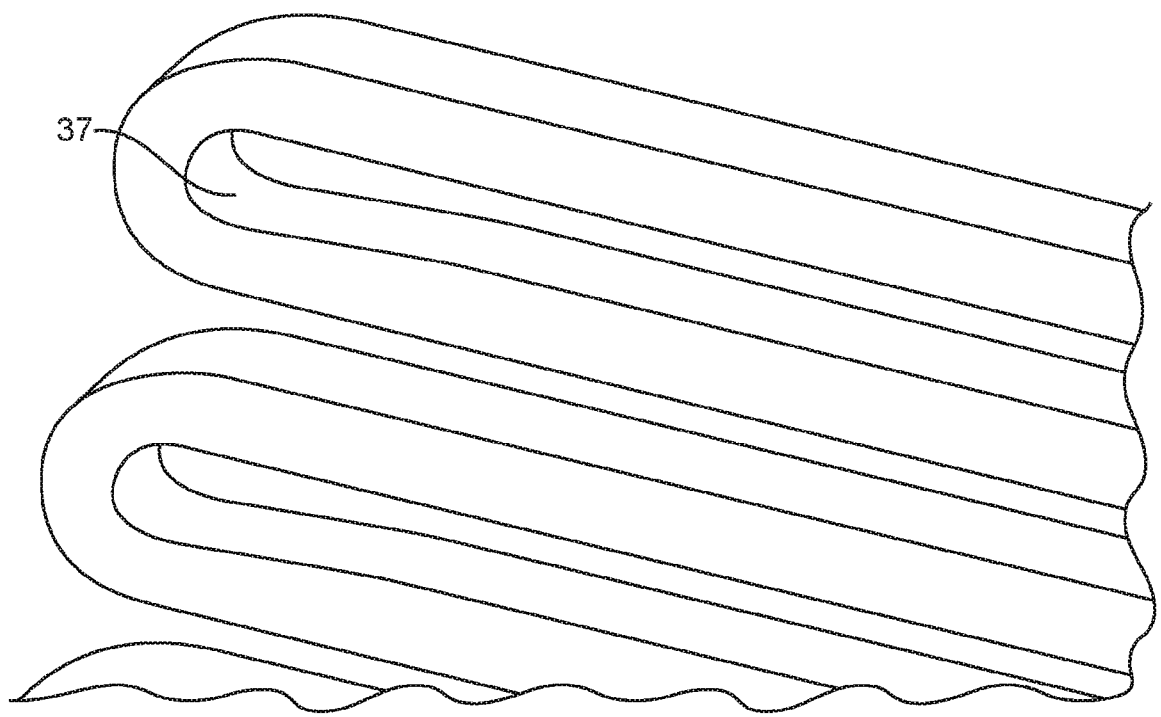
FIG. 27 provides a zoomed in view of the serpentine channels of FIG. 25 showing a contoured turnaround region 27.

FIG. 27 provides a further zoomed-in view of the serpentine channel of FIG. 25 showing the contoured turnaround regions 37 which remove low shear regions.

Figure 28:
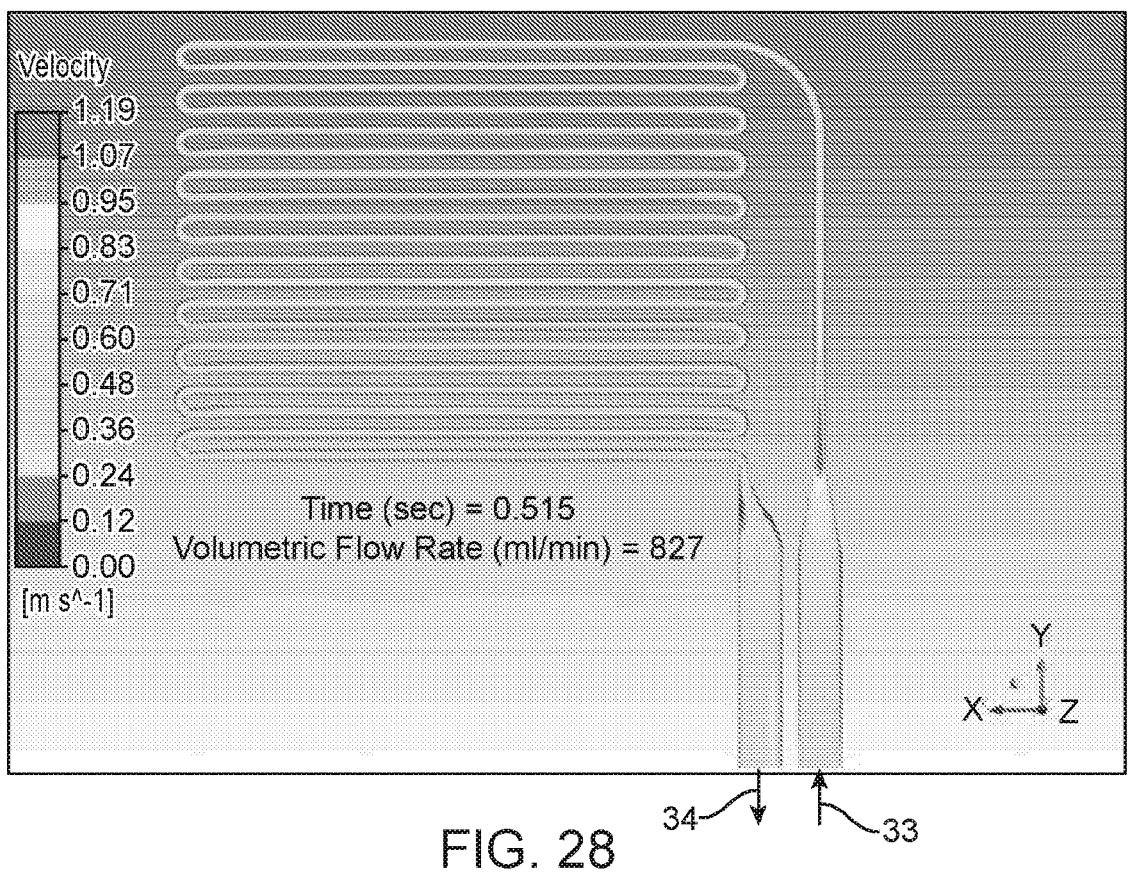
FIG. 28 illustrates blood velocity on an XY-symmetry plane, showing smooth flow patterns through the turnaround sections of the serpentine flow channel.

FIG. 28 illustrates the speed contours of blood on an XY-symmetry plane, showing smooth flow patterns through the turnaround sections. Inlet conduit shows an initial fluid velocity in the range of 0.36-0.83 m/sec at the entrance of inlet conduit, with an short region with an increase of fluid velocity (in the region where the cross-sectional area of the inlet transitions from a circular to a rectangular geometry), followed by a decrease ranging from 0.24-0.36 m/sec as the fluid flows into the filtration regions of the serpentine channel. Outlet conduit shows a fluid velocity in the range of 0.36-0.83 m/sec.

Figure 29:
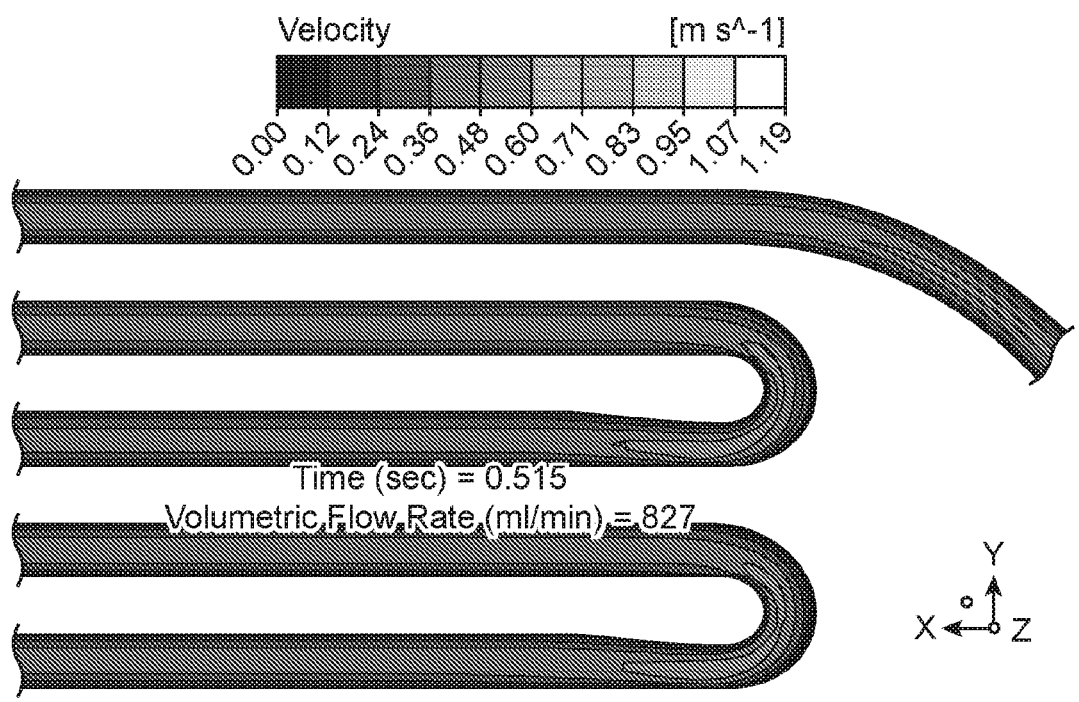
FIG. 29 illustrates a zoomed in view of contour for velocity of blood through the serpentine channel of FIG. 28, showing a good transition from the inlet to the serpentine channel with the range of 0.24-0.48 m/sec, with smooth and repeatable flow patterns through the turnaround sections.

FIG. 29 illustrates speed contours of the serpentine channel of FIG. 28, showing a good transition from the inlet conduit to the serpentine channel with speed in the range of 0.24-0.48 m/sec, with smooth and repeatable flow patterns through the turnaround sections.

Figure 30:
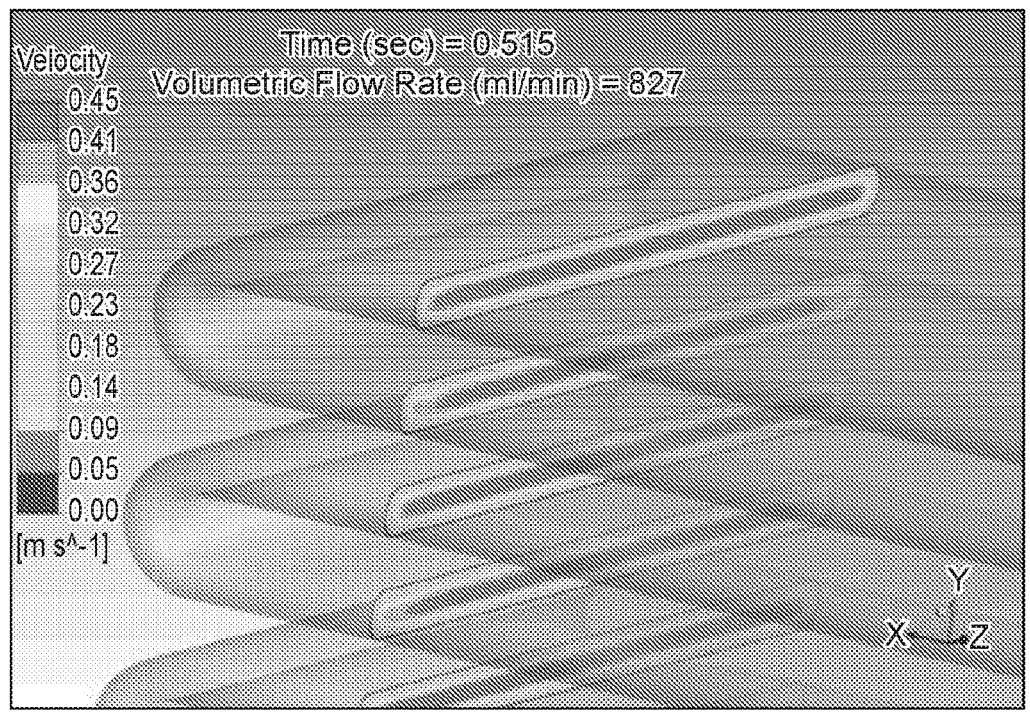
FIG. 30 illustrates speed contours in the YZ plane, near the turnaround regions of the serpentine channel with good uniformity and repeatability of flow amongst and within the serpentine channel.

FIG. 30 illustrates speed contours in the YZ plane, near the turnaround regions of the serpentine channel with good uniformity and repeatability of flow amongst and within the sequential filtration regions of serpentine channel.

Figure 31:
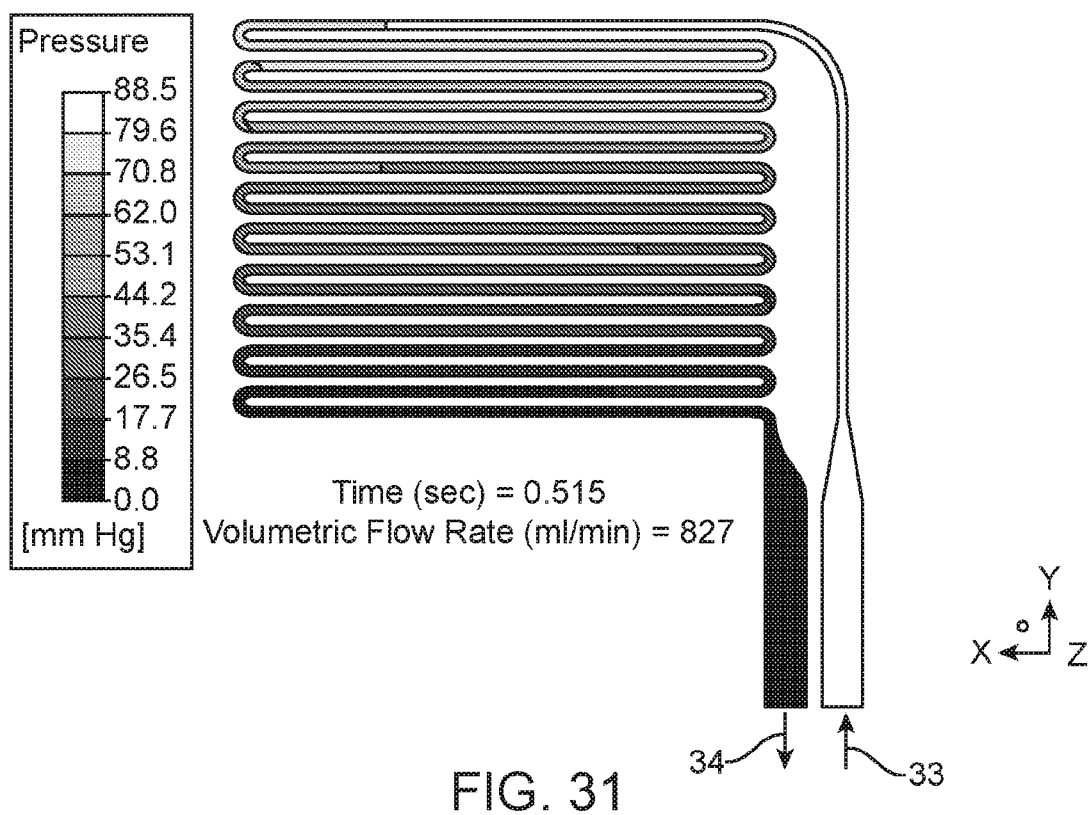
FIG. 31 illustrates the static pressure contours in the XY centerline plane of the hemofilter.

FIG. 31 illustrates the static pressure contours in the XY centerline plane of the hemofilter, where a pressure drop of 88.5 mmHg occurs, which is significantly higher than 6 mmHg of the extended inlet design of FIGS. 1-23. To reduce the pressure drop, the thickness of the flow paths within the channel can be increased from 1.5 mm to 2.50 mm, or the hemofilter can have a two system design with 10 filtration regions in each serpentine channel.

Figure 32:
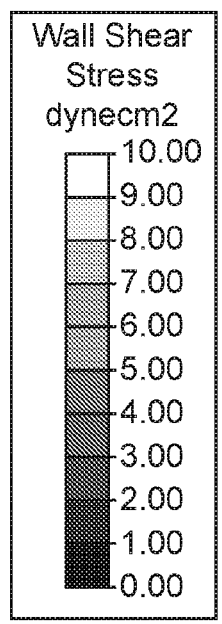
FIG. 32 illustrates regions of low wall shear stress in the hemofilter.
Figure 32:
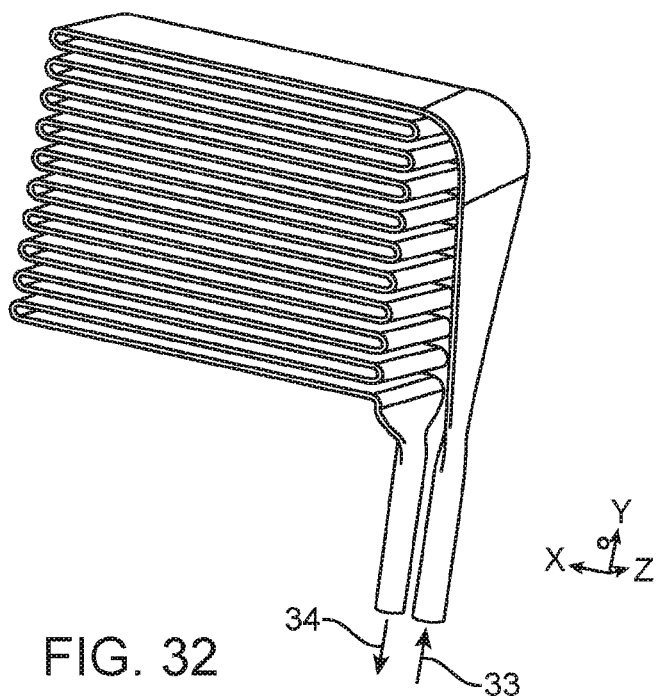

FIG. 32 illustrates the wall shear stress at a low range of about 10 dyne/cm$^2$.

Figure 33:
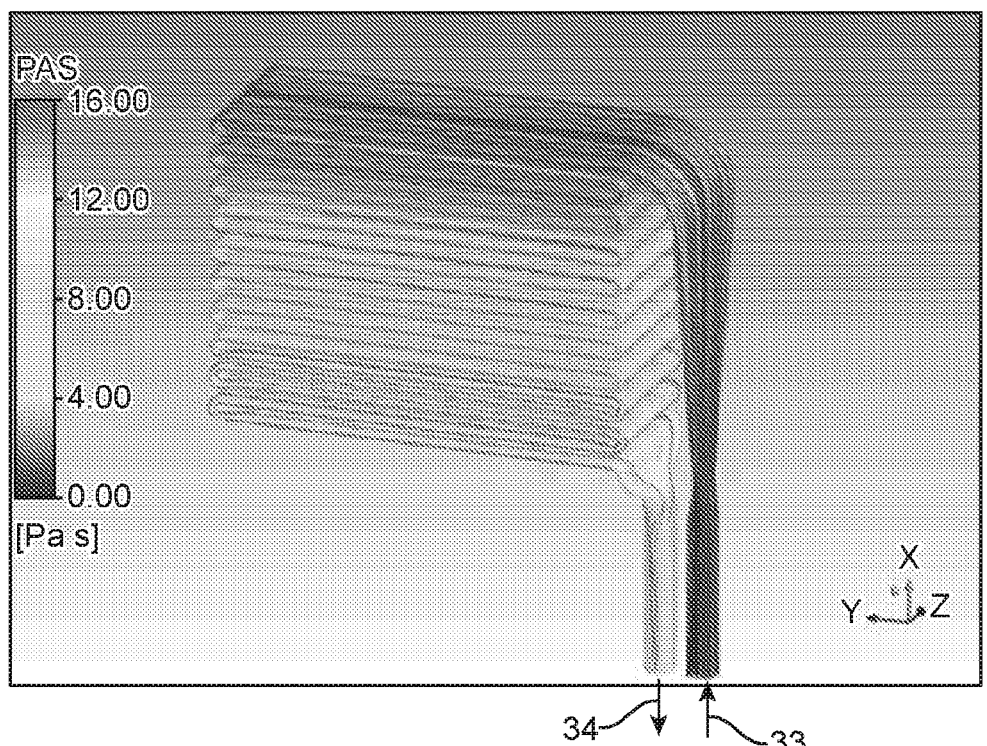
FIG. 33 illustrates platelet stress accumulation along particle paths in a hemofilter with serpentine channel, showing the highest PSA along the corners and near the walls in the slowest moving regions of the channels.

FIG. 33 illustrates the platelet stress accumulation (PSA) along particle paths of the hemofilter with a serpentine channel, showing the highest PSA along the corners and near the walls in the slowest moving regions of the channels. The results show higher PSA values for the serpentine channel (16 Pa*sec) compared with the extended inlet manifold of FIG. 23 (3 Pa*sec). The upper limit of PSA range was limited to 16 Pa*sec to better visualize the variations in FIG. 33. The CFD model input parameters for the steady state simulations included laminar flow with a low Reynolds number flow; particle tracking with 3 mm diameter platelet particles, neutrally buoyant particles, and a two-way couple particle/flow field model; boundary conditions which included an inlet flow rate of 827 ml/min (maximum flow rate), and an outlet average static pressure of 0 mmHg; and non-Newtonian blood at 37° C. using a cross non-newtonian viscosity model and a density of 1060 kg/m$^3$. The cross-non-Newtonian viscosity model included an infinite shear limit of 3.5 cps, and a zero shear limit of 56.0 cps.

Figure 34:
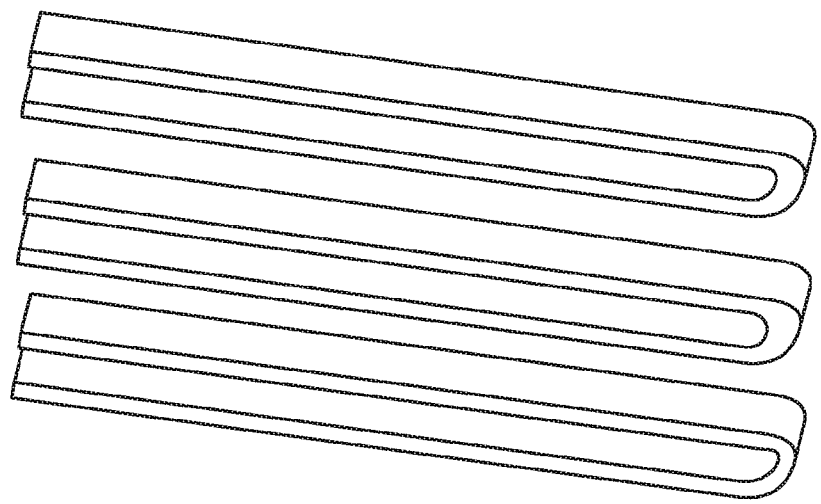
FIG. 34 illustrates channel flow path geometry of a hemofilter with a serpentine channel.

FIG. 34 illustrates channel flow path geometry of the serpentine channel and the turnaround regions.

Figure 35:
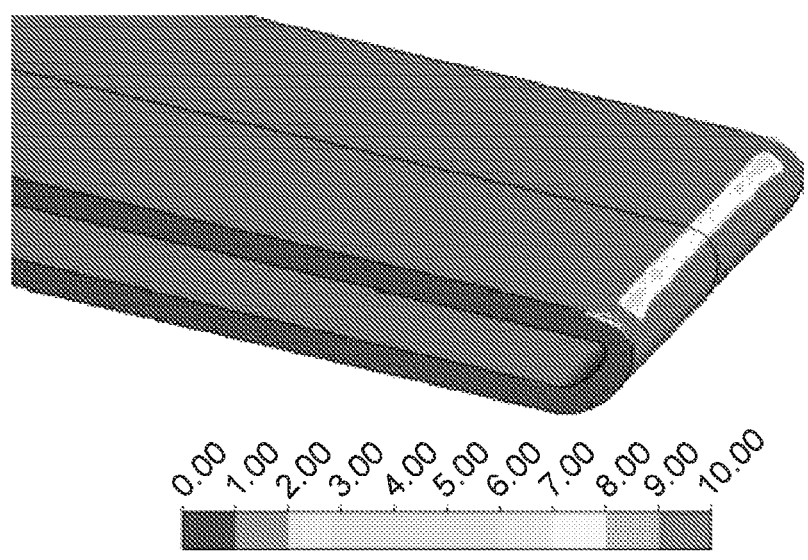
FIG. 35 illustrates an outer view of an ellipse shaped channel flow path geometry (ellipse 1) with wall shear stress contours.
Figure 36:
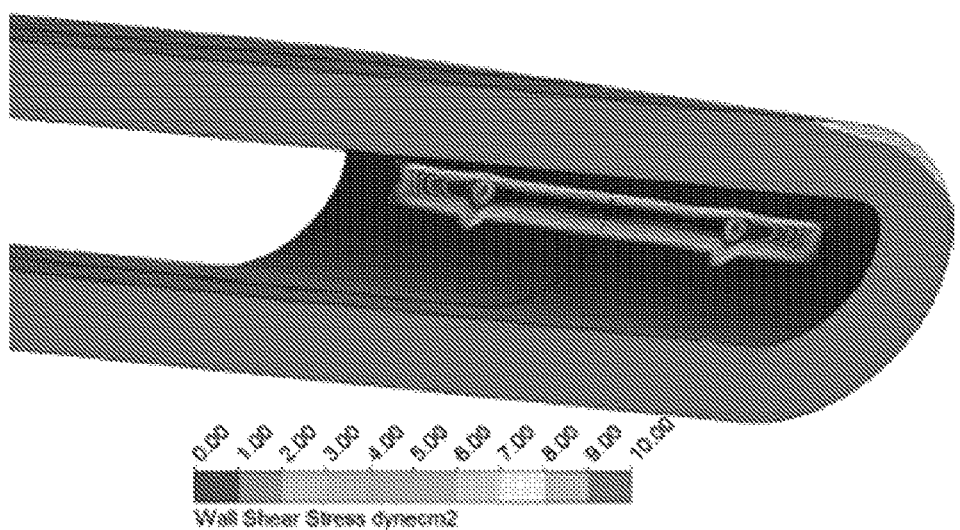
FIG. 36 illustrates an inner view of an ellipse shaped channel flow path geometry (ellipse 1) with wall shear stress contours.
Figure 37:
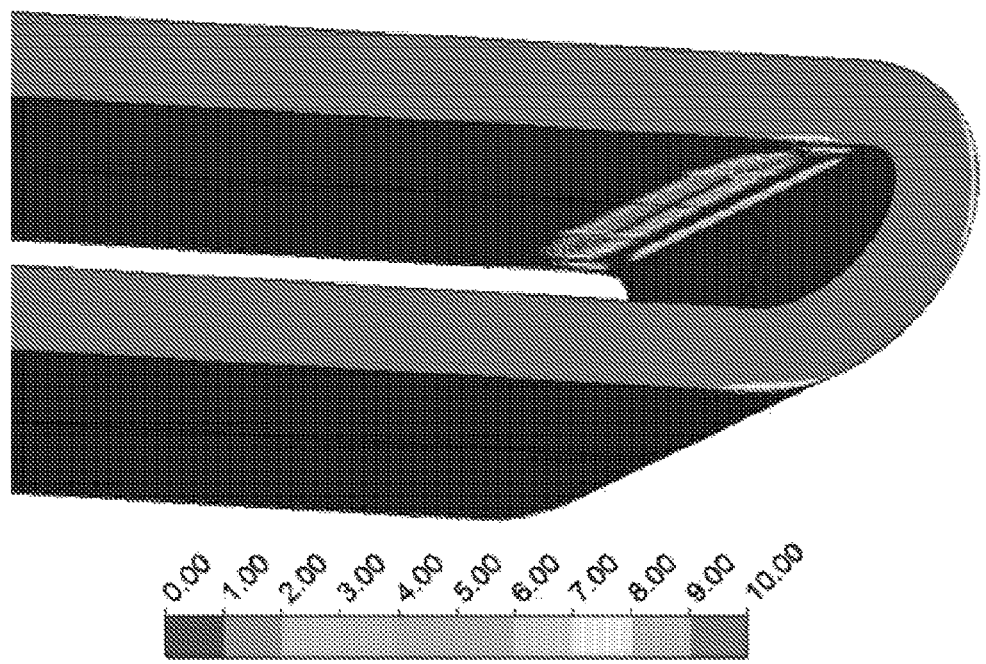
FIG. 37 illustrates another view of an ellipse shaped channel flow path geometry (ellipse 1) with wall shear stress contours.
Figure 38:
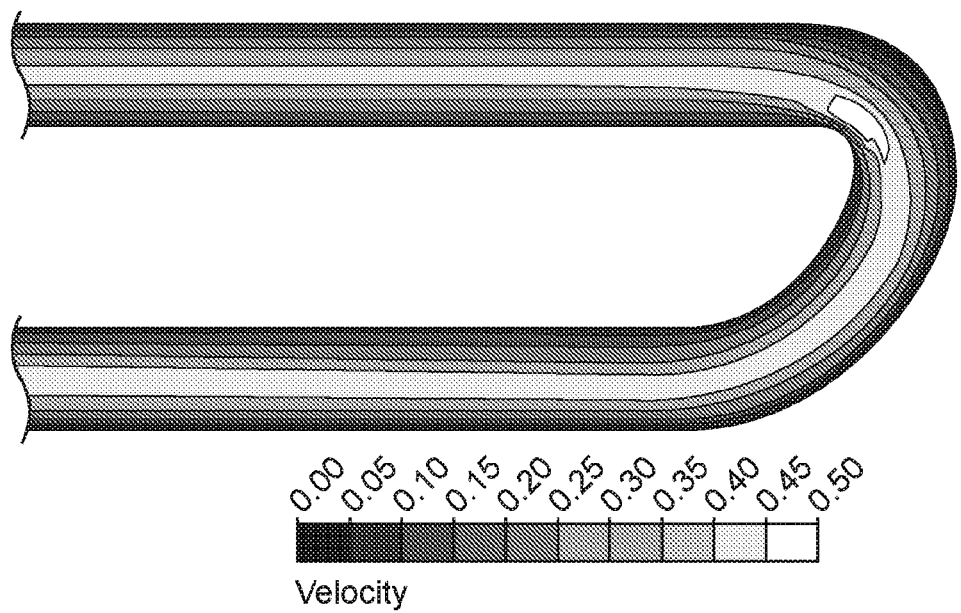
FIG. 38 illustrates an ellipse shaped channel flow path geometry (ellipse 1) showing fluid velocity for blood flowing from top region to bottom region of a serpentine channel on XY symmetry plane.
Figure 39:
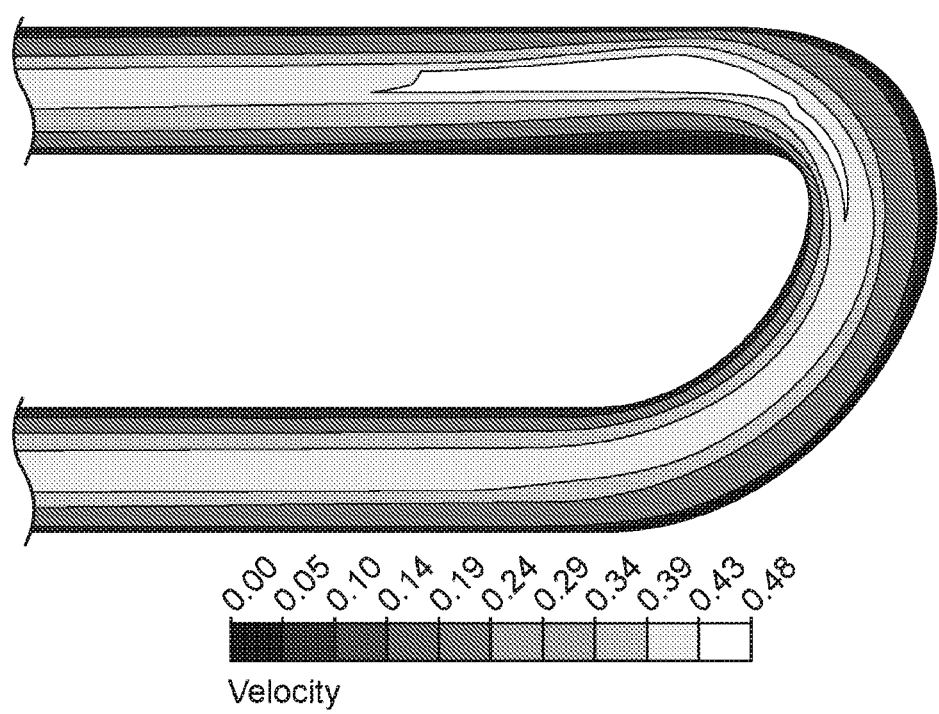
FIG. 39 illustrates an ellipse shaped channel flow path geometry (ellipse 1) showing fluid velocity for blood flowing from bottom region to top region of a serpentine channel on XY symmetry plane.
Figure 40:
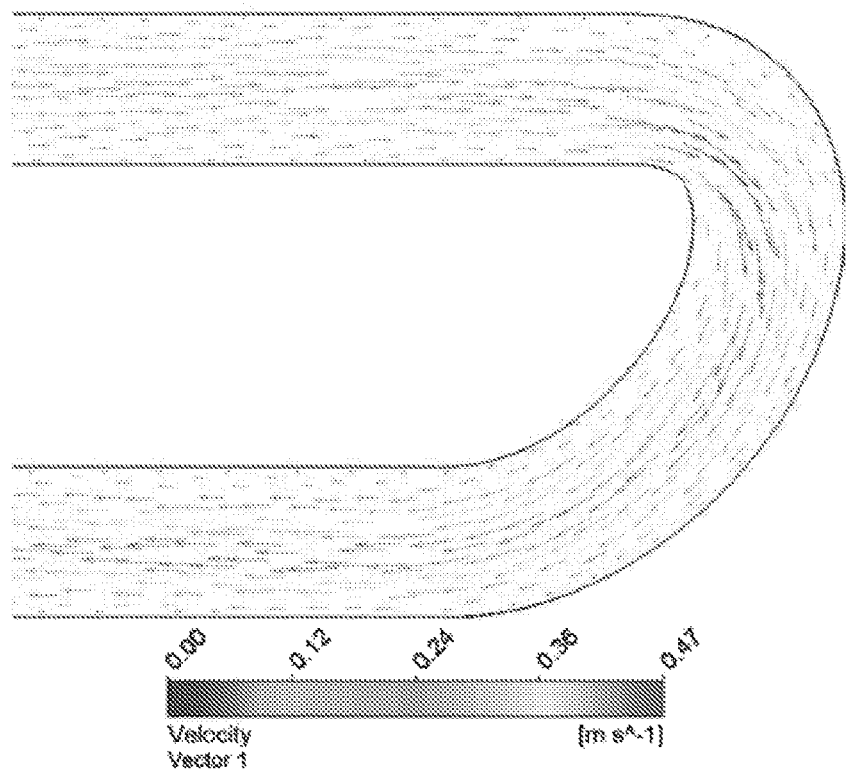
FIG. 40 illustrates an ellipse shaped channel flow path geometry (ellipse 1) showing velocity vectors for blood flowing from top region to bottom region of a serpentine channel on XY symmetry plane.
Figure 41:
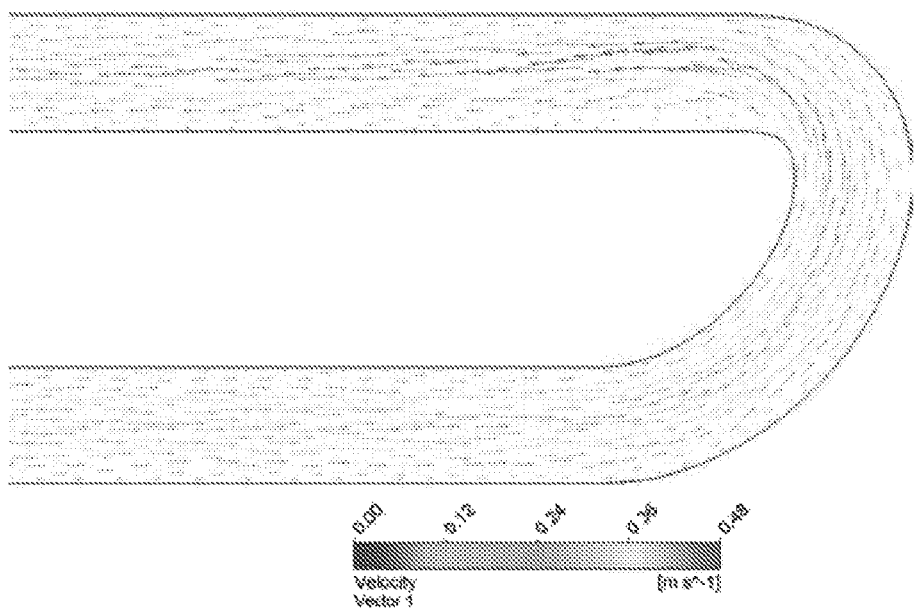
FIG. 41 illustrates an ellipse shaped channel flow path geometry (ellipse 1) showing velocity vectors for blood flowing from bottom region to top region of a serpentine channel on XY symmetry plane.

FIG. 35 illustrates regions of low wall shear stress of an ellipse-shaped (ellipse 1) turnaround region of the serpentine channel. FIG. 36 illustrates an inner view of an ellipse (ellipse 1) shaped turnaround region highlighting wall locations with wall shear stress below 10 dyne/cm$^2$. Shear stress less than 10 dyne/cm$^2$ occurs along the outer and inner walls of the turnaround region. FIG. 37 illustrates another view of an ellipse shaped (ellipse 1) turnaround region showing wall shear stress contours. FIG. 38 illustrates an ellipse shaped (ellipse 1) turnaround region showing fluid velocity (top to bottom) on the symmetry plane. FIG. 39 illustrates an ellipse shaped (ellipse 1) turnaround region showing fluid velocity in the reverse direction (bottom to top) on the symmetry plane. FIG. 40 illustrates an ellipse shaped (ellipse 1) turnaround region showing velocity vectors (top to bottom) on the XY symmetry plane. FIG. 41 illustrates an ellipse shaped (ellipse 1) turnaround region showing velocity vectors (bottom to top) on the XY symmetry plane.

Figure 42:
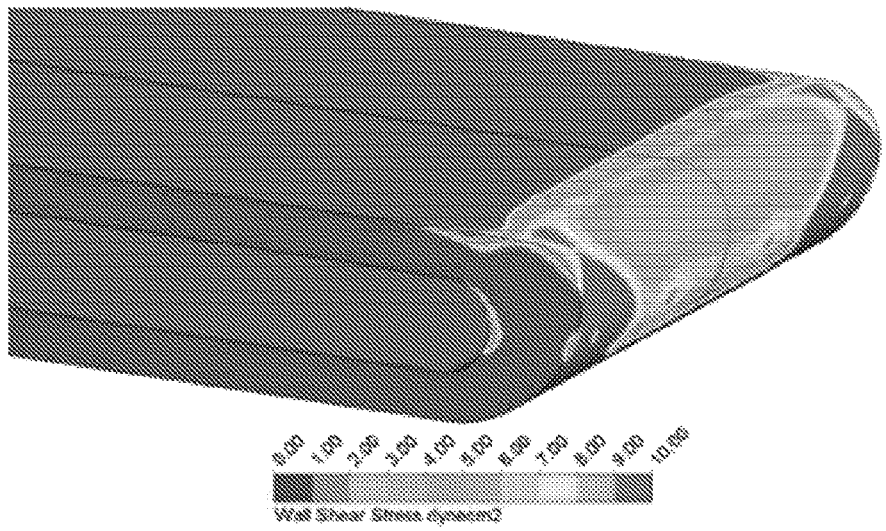
FIG. 42 illustrates an ellipse shaped channel flow path geometry (ellipse 2) showing wall shear stress contours for blood flowing from top region to bottom region of a serpentine channel on XY symmetry plane.
Figure 43:
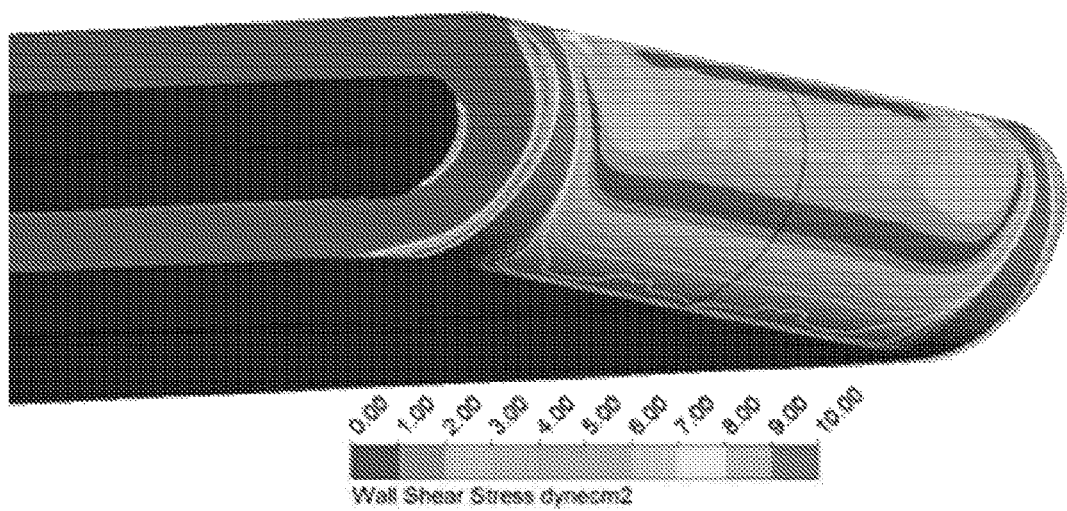
FIG. 43 illustrates an ellipse shaped channel flow path geometry (ellipse 2) showing wall shear stress for blood flowing from bottom region to top region of a serpentine channel on XY symmetry plane.
Figure 44:
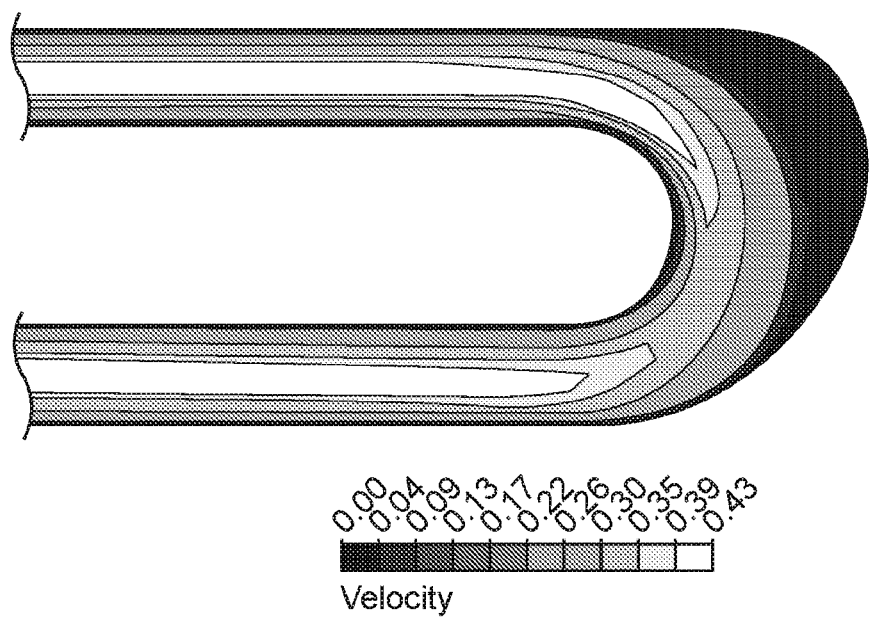
FIG. 44 illustrates an ellipse shaped channel flow path geometry (ellipse 2) showing fluid velocity for blood flowing from top region to bottom region of a serpentine channel on XY symmetry plane.
Figure 45:
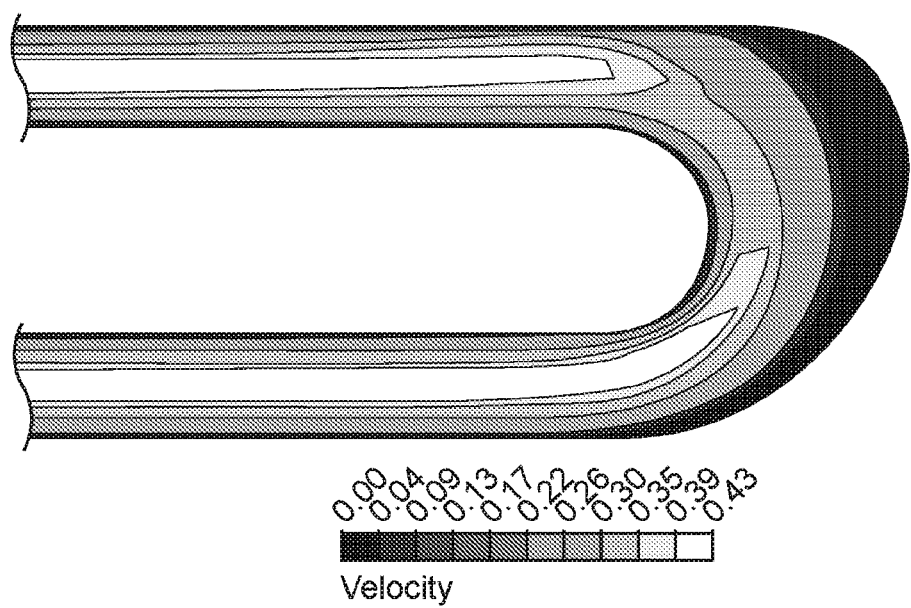
FIG. 45 illustrates an ellipse shaped channel flow path geometry (ellipse 2) showing fluid velocity for blood flowing from bottom region to top region of a serpentine channel on XY symmetry plane.
Figure 46:
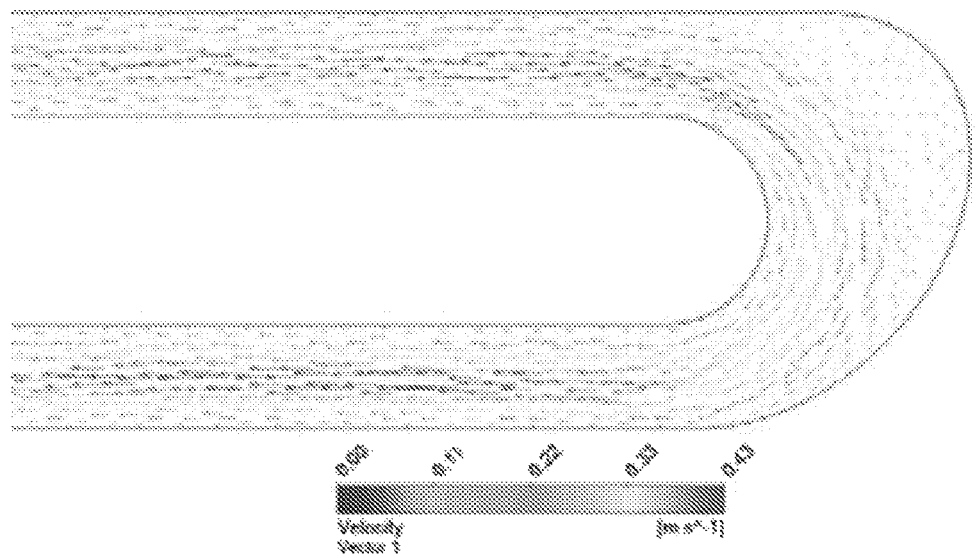
FIG. 46 illustrates an ellipse shaped channel flow path geometry (ellipse 2) showing velocity vectors for blood flowing from top region to bottom region of a serpentine channel on XY symmetry plane.
Figure 47:
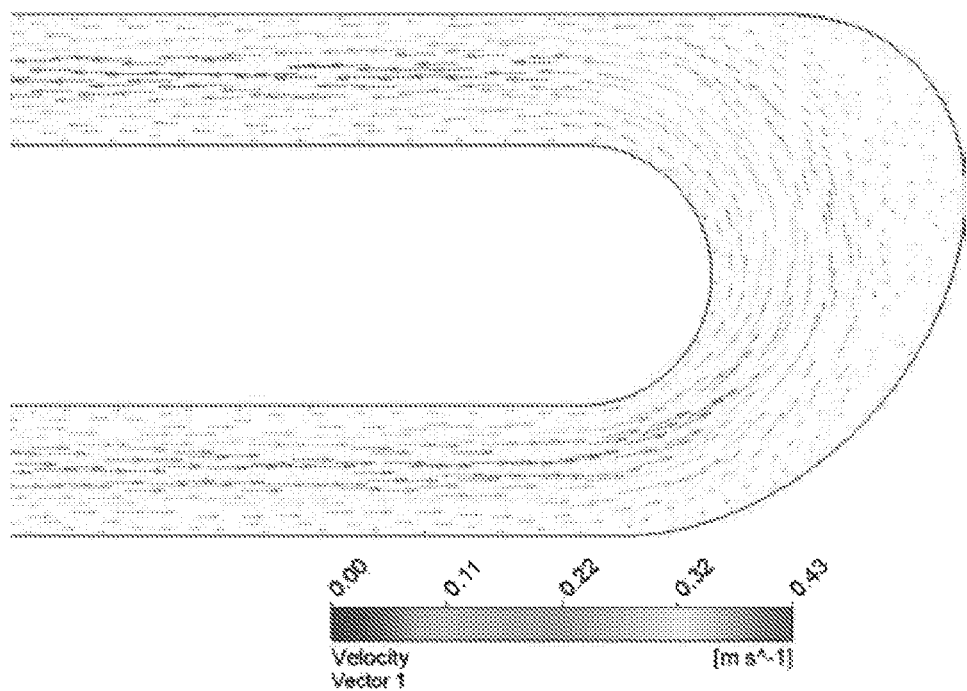
FIG. 47 illustrates an ellipse shaped channel flow path geometry (ellipse 2) showing velocity vectors for blood flowing from bottom region to top region of a serpentine channel on XY symmetry plane.

FIG. 42 illustrates a semi-ellipse shaped turnaround region (ellipse 2) showing wall shear stress contours (top to bottom) on the symmetry plane. FIG. 43 illustrates a semi-ellipse shaped turnaround region (ellipse 2) showing wall shear stress contours (bottom to top) on the symmetry plane. FIG. 44 illustrates a semi-ellipse shaped turnaround region (ellipse 2) showing fluid velocity (top to bottom) on the XY symmetry plane. FIG. 45 illustrates a semi-ellipse shaped turnaround region (ellipse 2) showing fluid velocity in the reverse direction (bottom to top) on the symmetry plane. FIG. 46 illustrates a semi-ellipse shaped turnaround region (ellipse 2) showing velocity vectors (top to bottom) on the symmetry plane. FIG. 47 illustrates a partial ellipse shaped turnaround region (ellipse 2) showing velocity vectors (bottom to top) on the symmetry plane.

Figure 48:
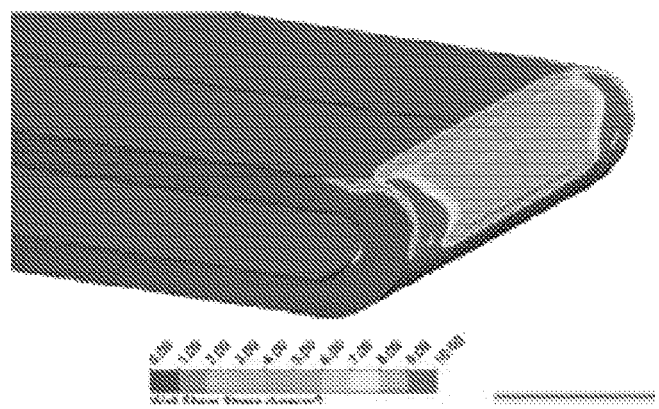
FIGS. 48 and 49 illustrate an ellipse shaped channel flow path geometry (ellipse 3) showing wall shear stress contours for blood flowing from top region to bottom region of a serpentine channel on XY symmetry plane.
Figure 49:
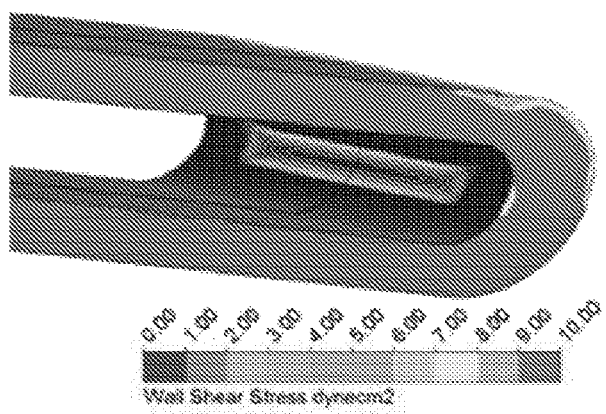
Figure 50:
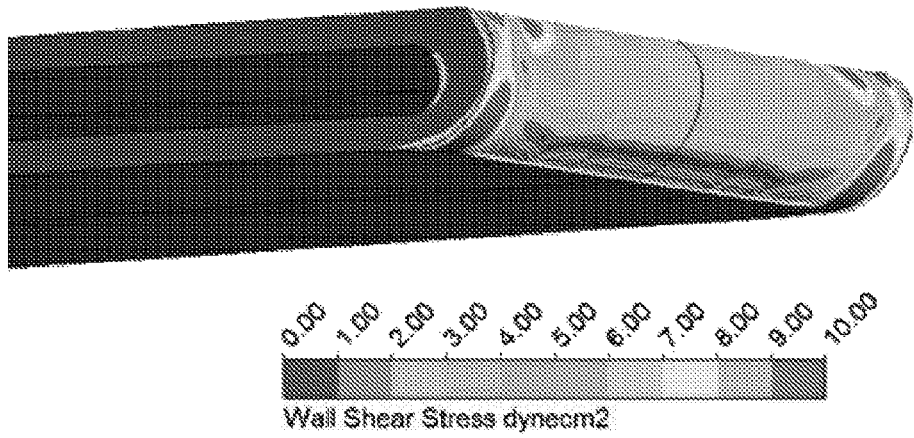
FIG. 50 illustrates an ellipse shaped channel flow path geometry (ellipse 3) showing wall shear stress contours for blood flowing from bottom region to top region of a serpentine channel on XY symmetry plane.
Figure 51:
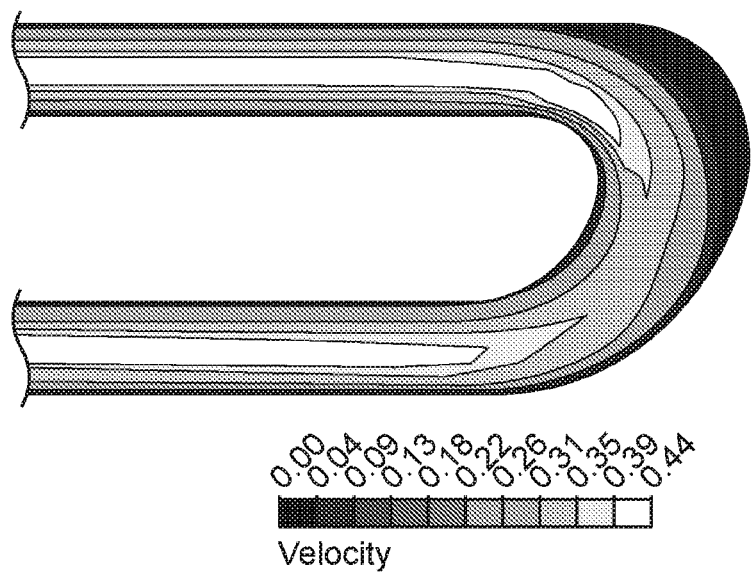
FIG. 51 illustrates an ellipse shaped channel flow path geometry (ellipse 3) showing fluid velocity for blood flowing from top region to bottom region of a serpentine channel on XY symmetry plane.
Figure 52:
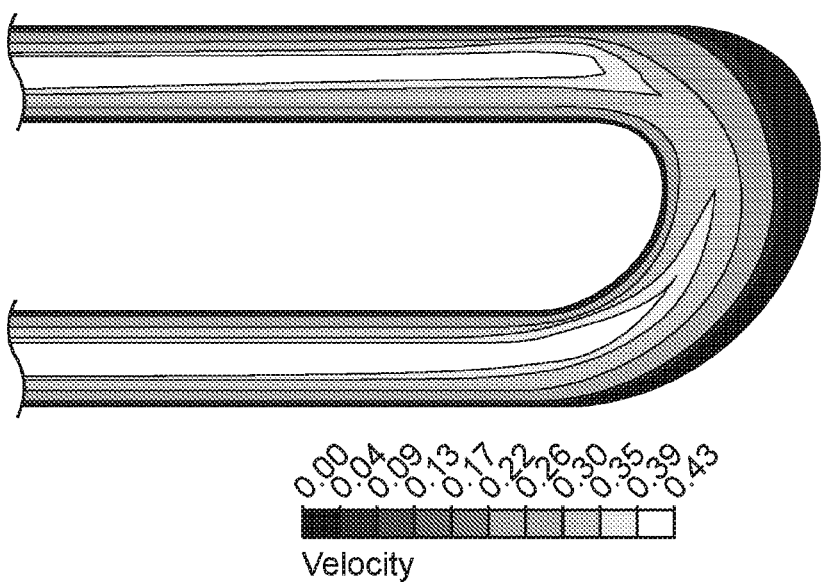
FIG. 52 illustrates an ellipse shaped channel flow path geometry (ellipse 3) showing fluid velocity for blood flowing from bottom region to top region of a serpentine channel on XY symmetry plane.
Figure 53:
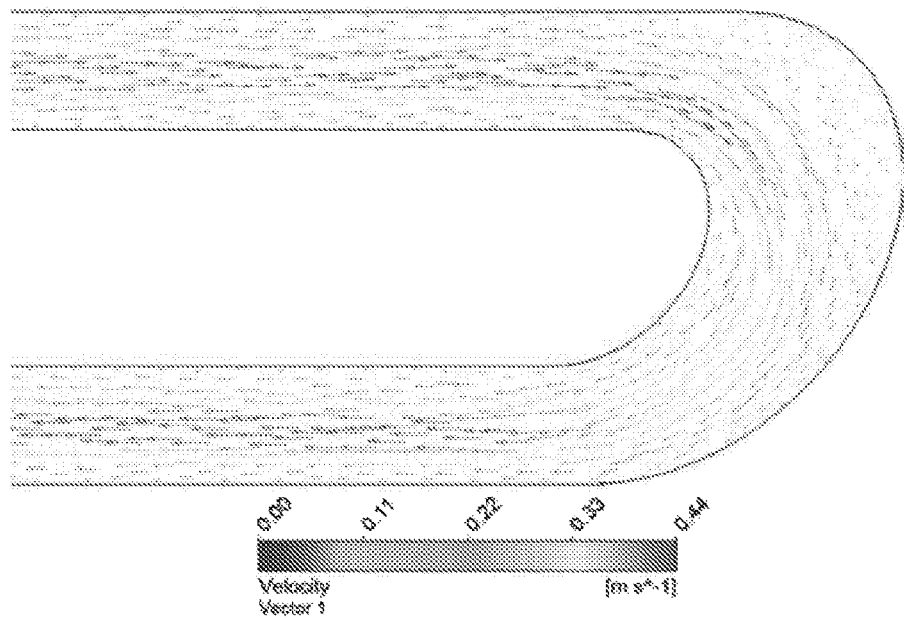
FIG. 53 illustrates an ellipse shaped channel flow path geometry (ellipse 3) showing velocity vectors for blood flowing from top region to bottom region of a serpentine channel on XY symmetry plane.
Figure 54:
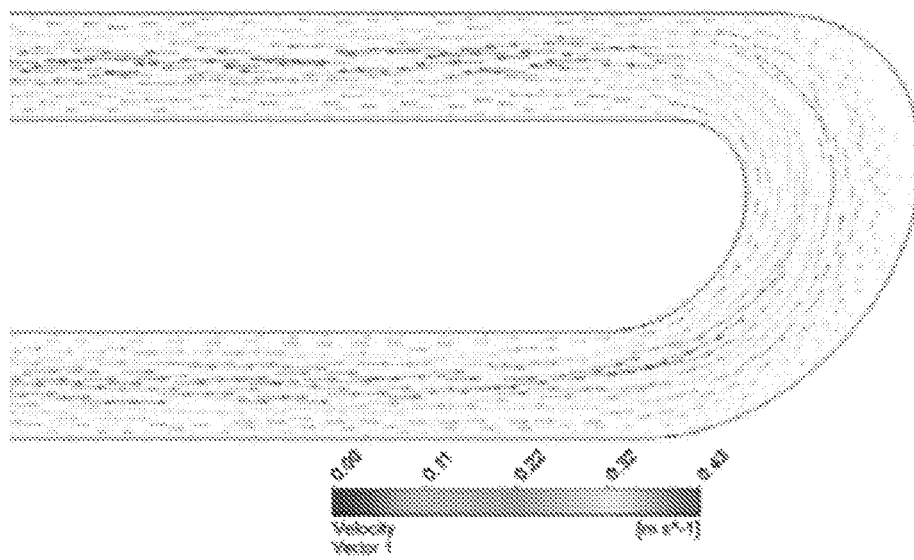
FIG. 54 illustrates an ellipse shaped channel flow path geometry (ellipse 3) showing velocity vectors for blood flowing from bottom region to top region of a serpentine channel on XY symmetry plane.

FIGS. 48-49 illustrate another partial ellipse shaped turnaround (ellipse 3) showing wall shear stress contours (top to bottom) on the symmetry plane. FIG. 50 illustrates another partial ellipse shaped turnaround (ellipse 3) showing wall shear stress contours (bottom to top) on the symmetry plane. FIG. 51 illustrates another partial ellipse shaped turnaround (ellipse 3) showing fluid velocity (top to bottom) on the symmetry plane. FIG. 52 illustrates another partial ellipse shaped turnaround (ellipse 3) showing fluid velocity in the reverse direction (bottom to top) on the symmetry plane. FIG. 53 illustrates another partial ellipse shaped turnaround (ellipse 3) showing velocity vectors (top to bottom) on the symmetry plane. FIG. 54 illustrates another partial ellipse shaped turnaround (ellipse 3) showing velocity vectors (bottom to top) on the symmetry plane.

Figure 55:
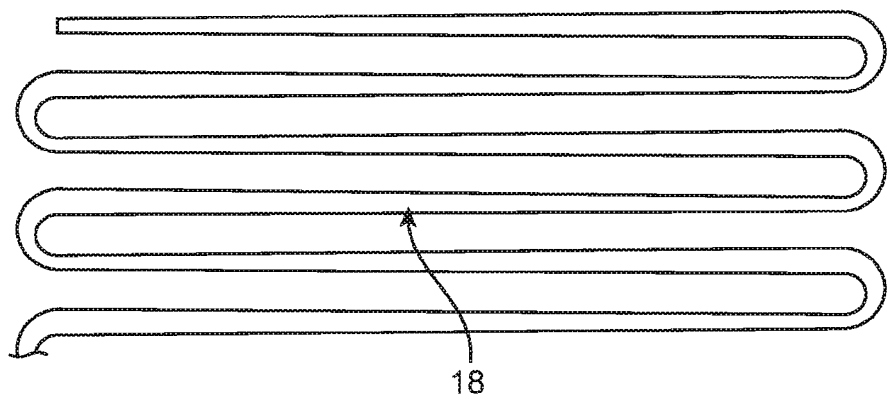
FIGS. 55 and 56 illustrate channel flow path geometries of a hemofilter provided herein.
Figure 56:
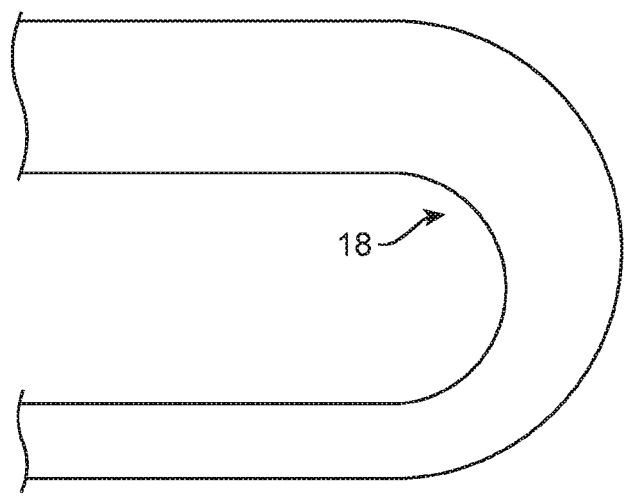

FIGS. 55-56 illustrate channel flow path geometries of the hemofilter having a single serpentine with a plurality of turnaround regions separating the filtration regions. The channel height increases across the filtration section 18 and starts to decrease towards the end of each turnaround region and has the shortest height at the end of the turnaround after which the height increases again across the next filtration region 18 and so on. The reduction in area in the turnaround accelerates flow around the turnaround avoiding areas of sustained low wall shear stress which can lead to formation of blood clots. In such an embodiment, the filtration regions are stacked and have a substantially parallel configuration channels that deviates by up to 10 degrees from a parallel configuration. In some embodiments, the height of the flow channel can increase from 1 mm to 2 mm (from start of a filtration region to end of the turnaround region) and decrease from 2 mm to 1 mm (from start of the filtration region to start of the next turnaround region).

Figure 57:
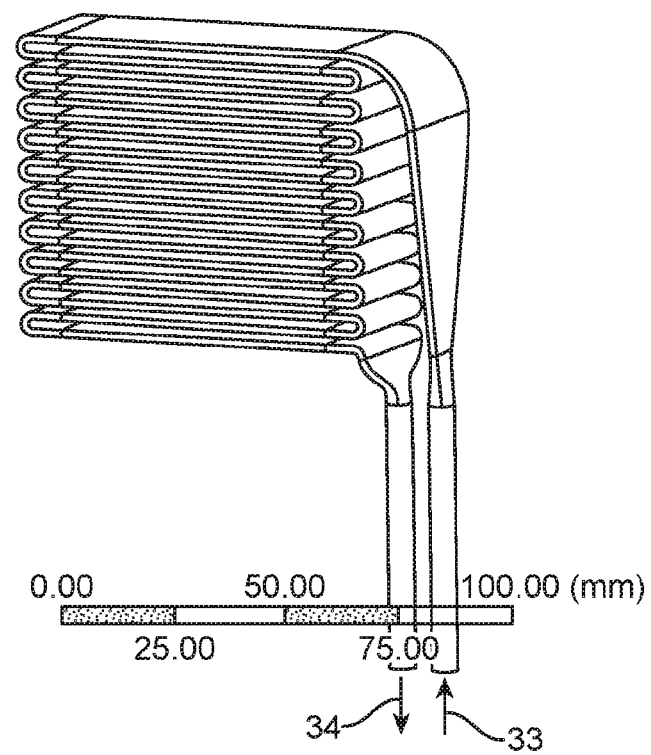
FIGS. 57 and 58 illustrate channel flow path geometries of a hemofilter.
Figure 58:
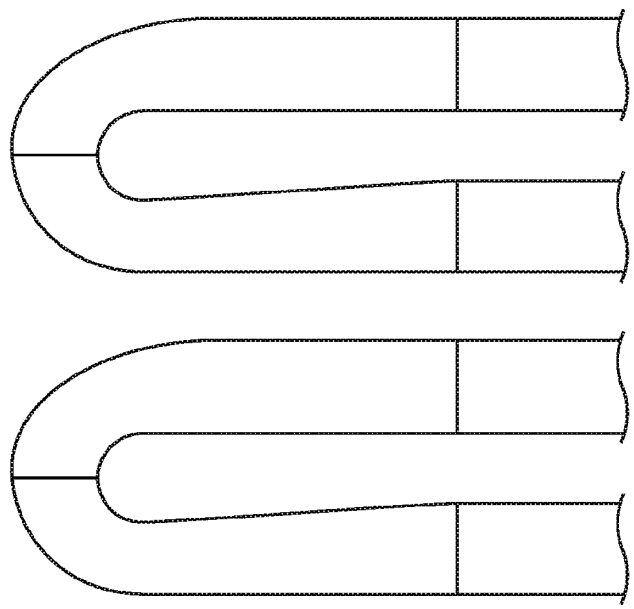
Figure 59:
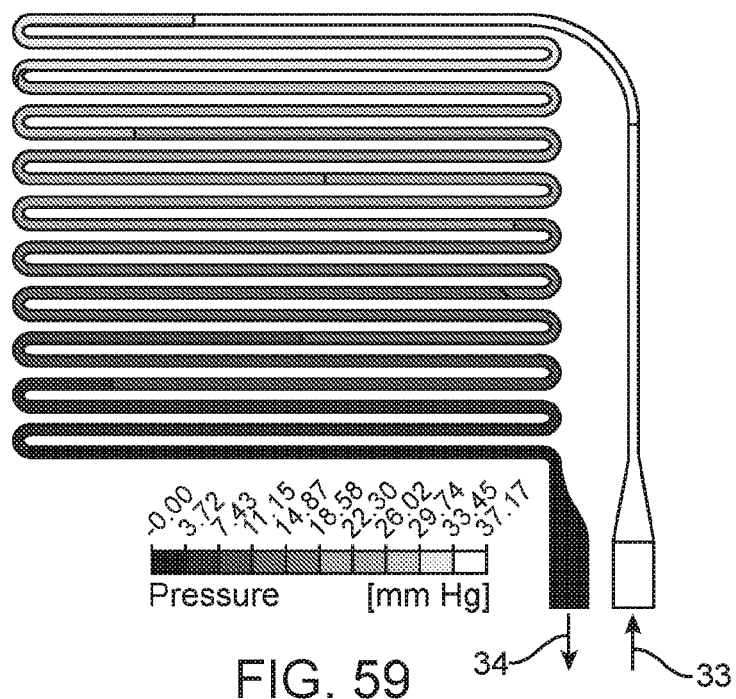
FIG. 59 illustrates static pressure contours of a hemofilter with serpentine channel provided herein.
Figure 60:
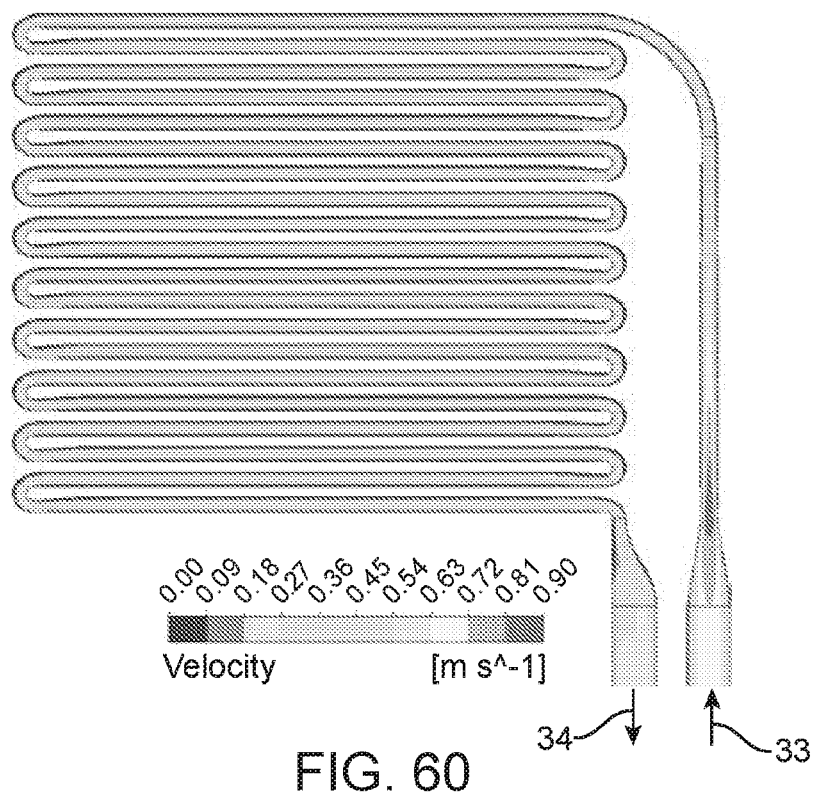
FIG. 60 illustrates symmetry plane velocity contours of a hemofilter with serpentine channel provided herein.

FIGS. 57-58 illustrate channel flow path geometries of the hemofilter. FIG. 59 illustrates static pressure contours of the hemofilter. FIG. 60 illustrates XY symmetry plane velocity contours of the hemofilter.

Figure 61:
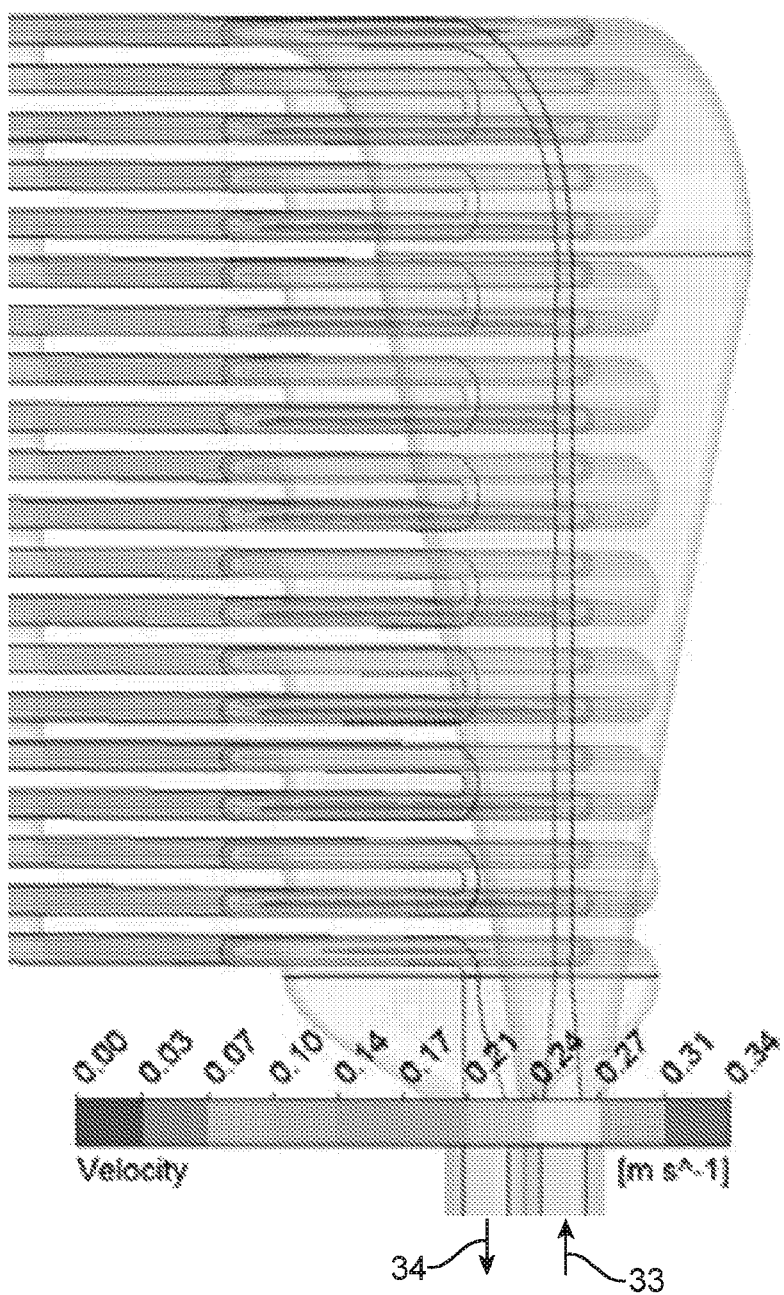
FIG. 61 illustrates velocity contours in a serpentine channel with a higher velocity at entrance of a section of the channel introduced due to blood traversing through a turn.

FIG. 61 illustrates inlet conduit and outlet conduit velocity contours, where velocity is at a peak going into the filtration region after traversing a turnaround region.

Figure 62:
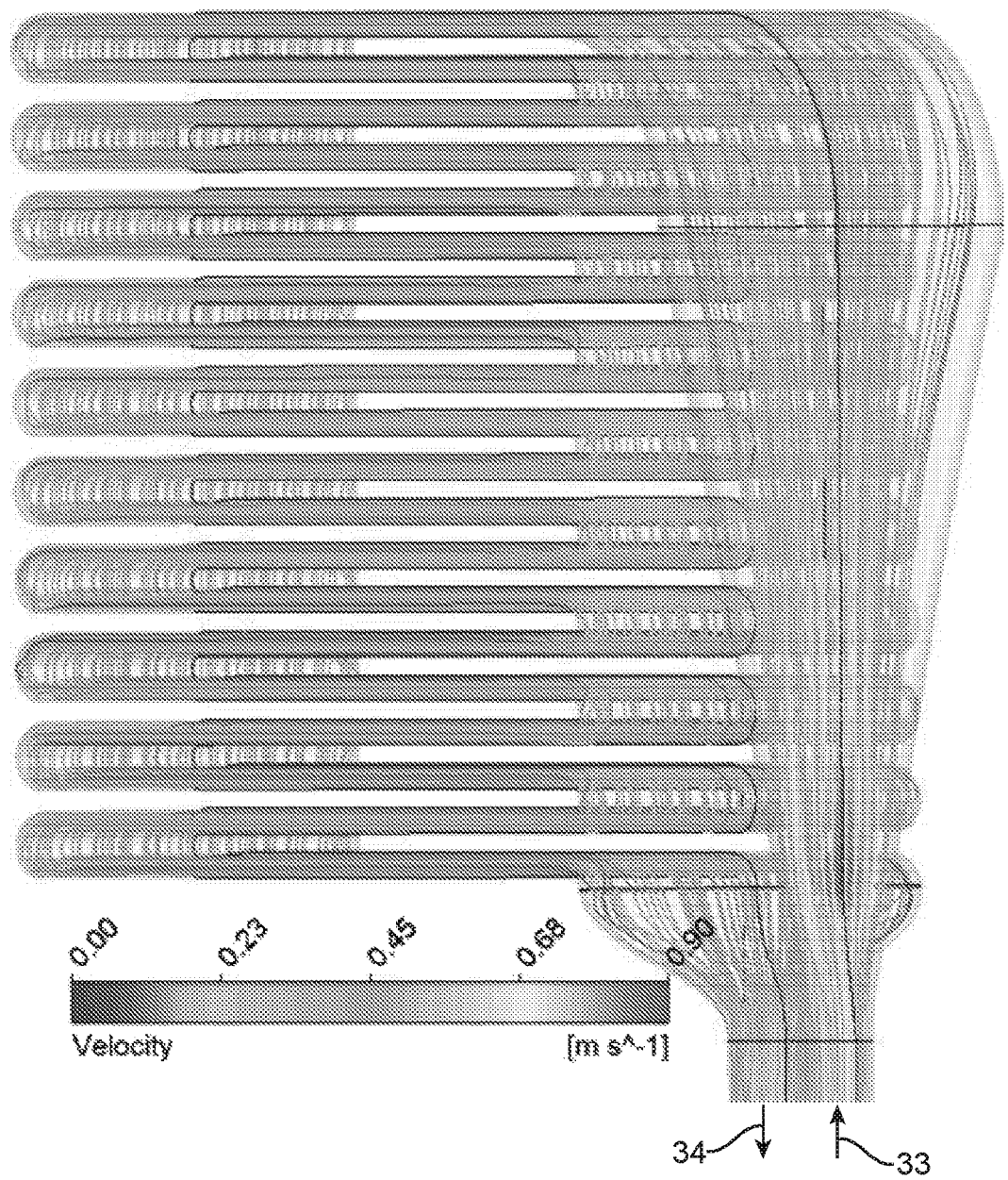
FIG. 62 illustrates streamlines colored by velocity of a hemofilter provided herein, where the flow fills the extended inlet.
Figure 63:
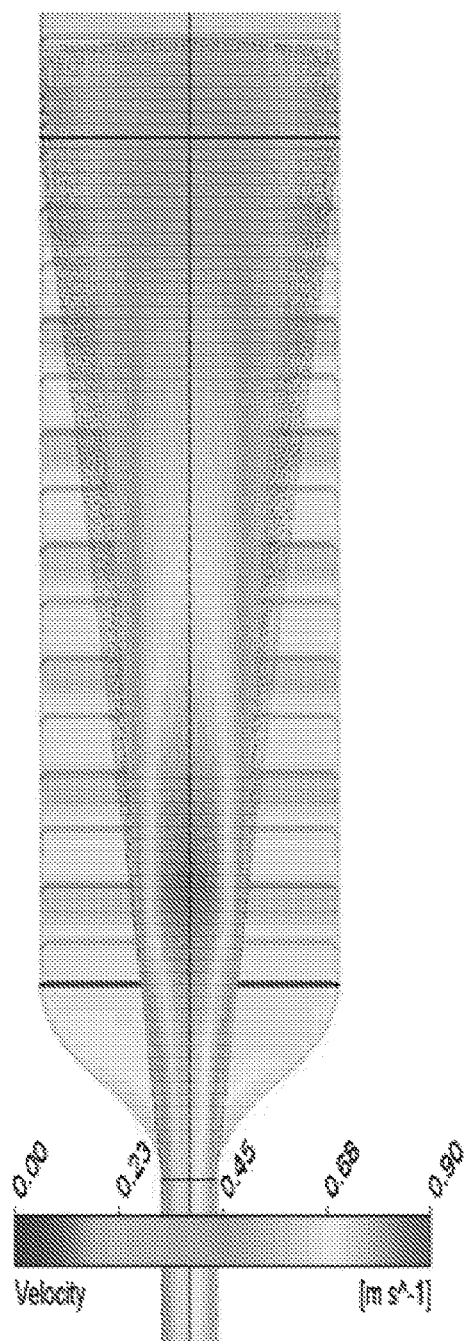
FIGS. 63 and 64 illustrate velocity vectors at the mid plane of the extended inlet of the hemofilter.
Figure 64:
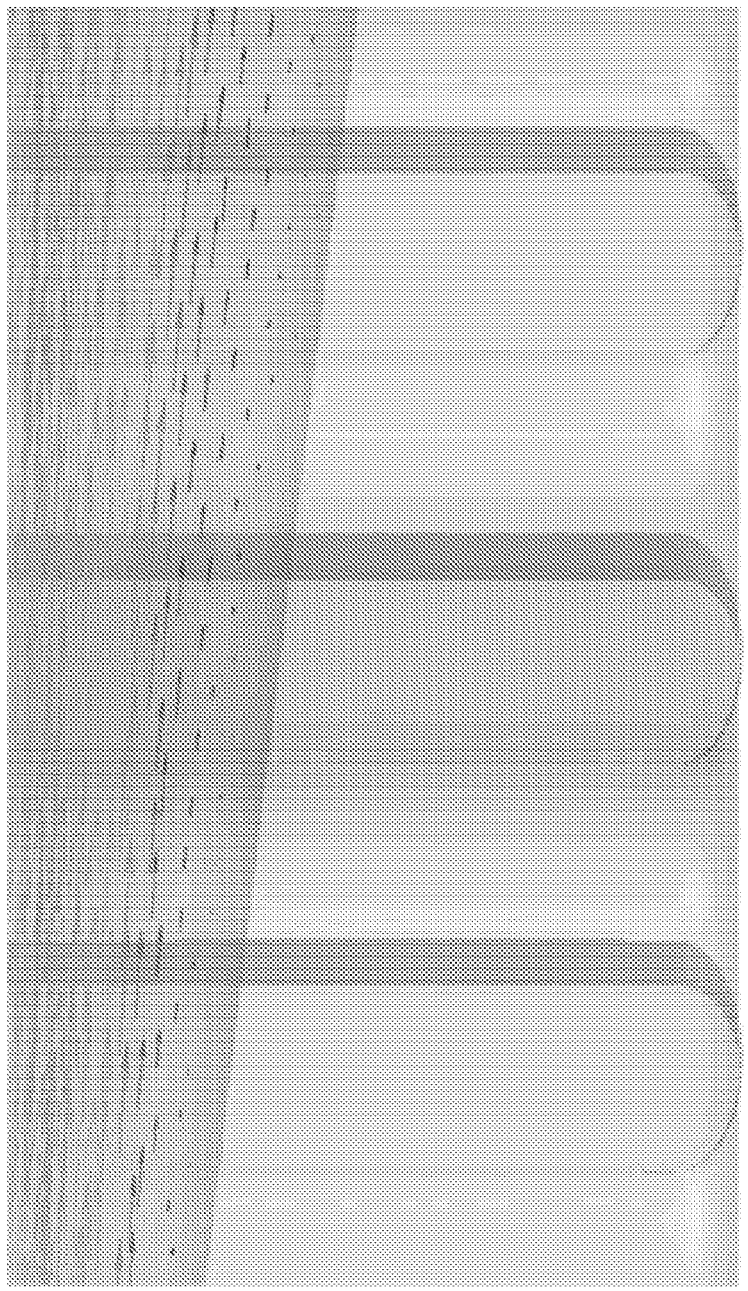

FIG. 62 illustrates streamline velocity contours in the hemofilter. FIGS. 63-64 illustrate velocity vectors at the mid plane of the extended inlet of the hemofilter. FIG. 63-64 depict a higher velocity where inlet conduit is initially necked down from a circular cross section into a rectangular cross section, whereas velocity is low along the edge, but blood does not appear to recirculate.

Figure 65:
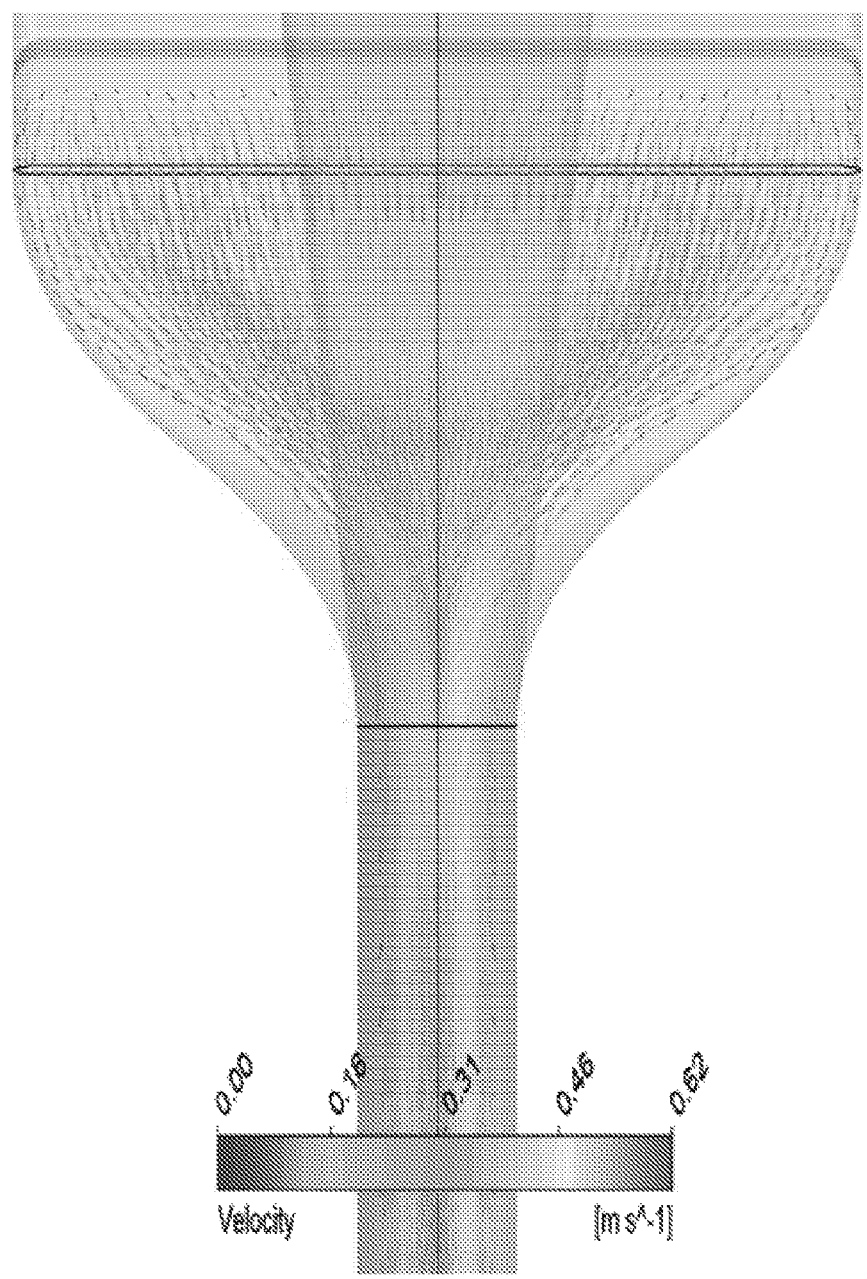
FIG. 65 illustrates velocity vectors at the midplane of the outlet conduit of the hemofilter.

FIG. 65 illustrates velocity vectors at the mid-plane of the outlet conduit. FIG. 65 shows a smooth flow into the outlet conduit.

Figure 66:
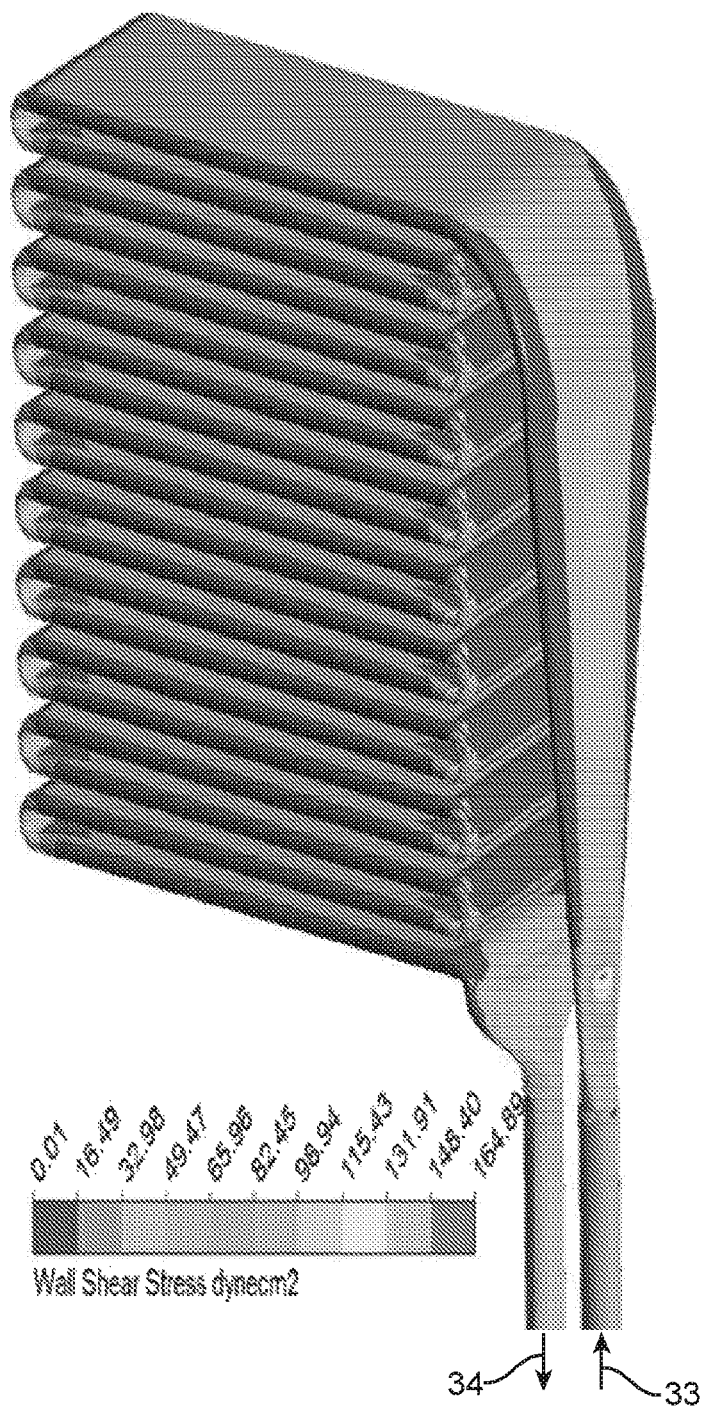
FIG. 66 illustrates wall shear stress contours of the hemofilter device, depicting a small region of higher wall shear stress where the inlet transitions from a circular cross section to a rectangular cross section.
Figure 67:
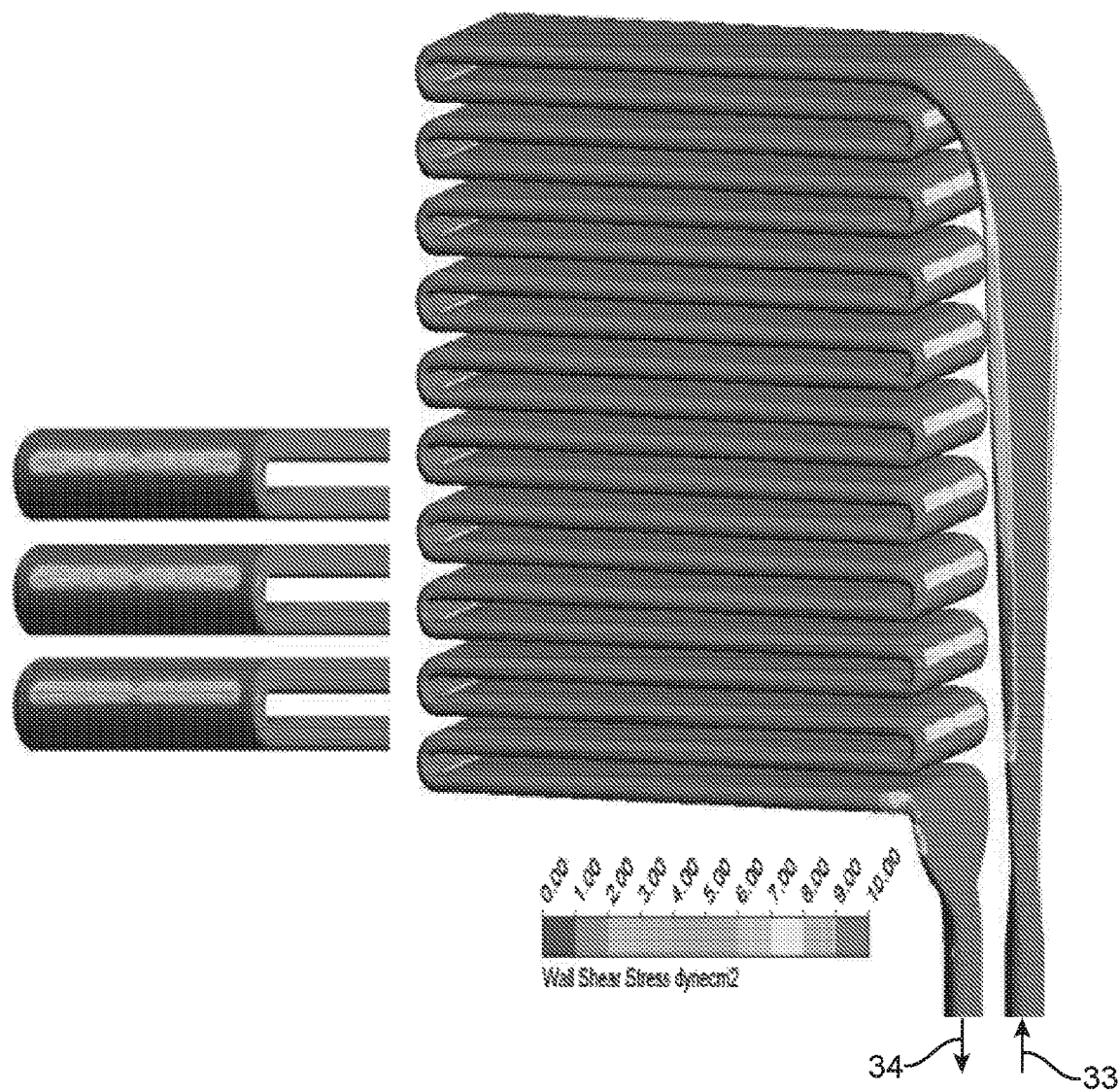
FIG. 67 illustrates wall shear stress contours of the hemofilter shown in FIG. 66.

FIG. 66 illustrates wall shear stress contours of the hemofilter, depicting a small region of higher wall shear stress where the inlet necks. FIG. 67 illustrates wall shear stress contours of the hemofilter.

Figure 68:
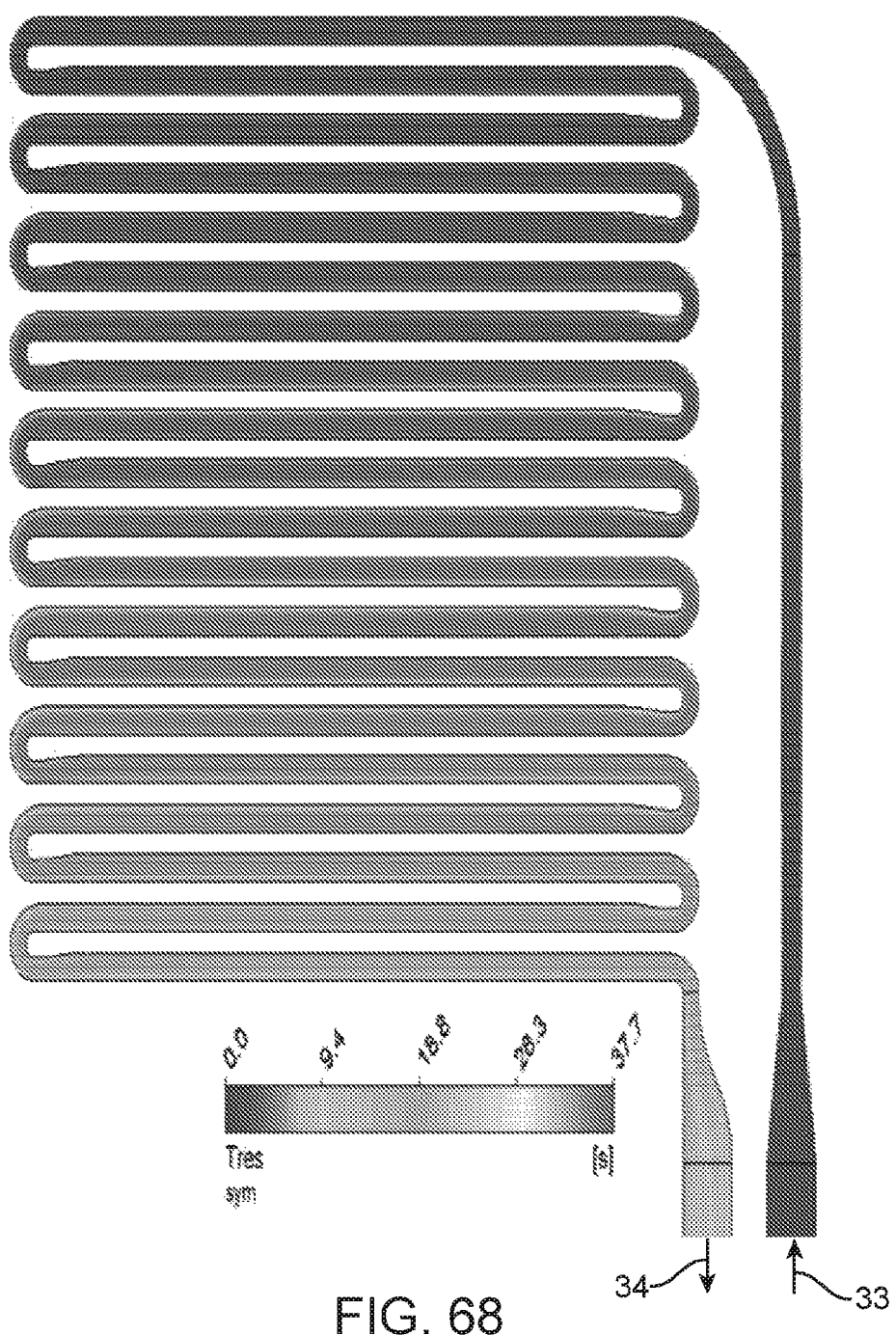
FIG. 68 illustrates resident time on the XY symmetry plane of the hemofilter shown in FIG. 66, where the mass average resident time at the outlet conduit is 9.04 seconds, whereas longer resident times occur for the blood flow near the walls.

FIG. 68 illustrates resident time on the XY symmetry plane of the hemofilter, where the mass average resident time at the outlet conduit is 9.04 seconds, whereas longer resident times occur along the walls.

Figure 69:
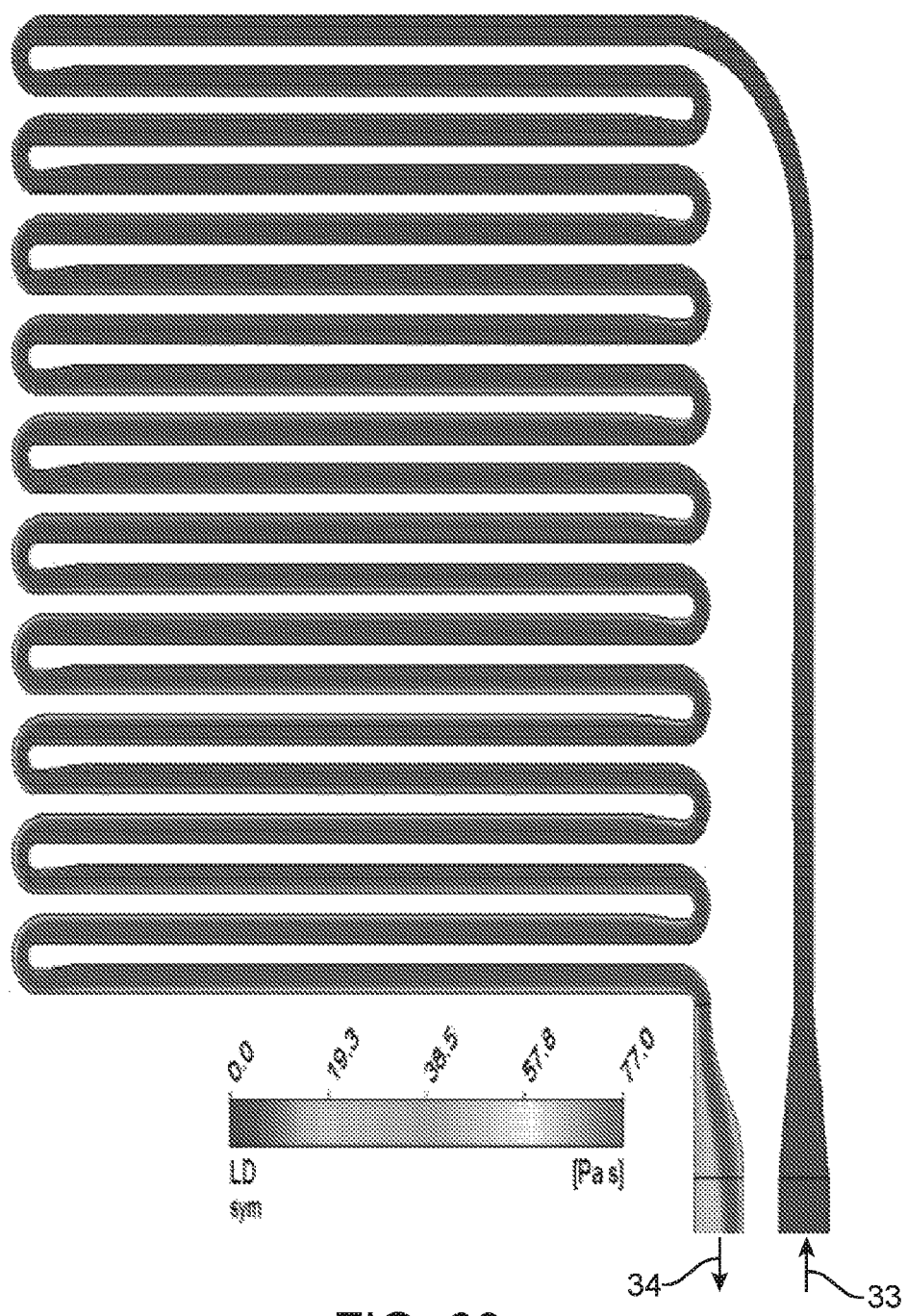
FIG. 69 illustrates accumulated stress on XY symmetry plane of the hemofilter, where accumulated stress is a time integral of viscosity X strain rate along the channel flow path.

FIG. 69 illustrates accumulated stress on the XY symmetry plane of the hemofilter, where accumulated stress is a time integral of viscosity times strain rate along the channel flow path. The mass average accumulated stress at the outlet is 10.6 Pa*sec, whereas higher accumulated stress was for the blood flow moving near the walls.

Figure 70:
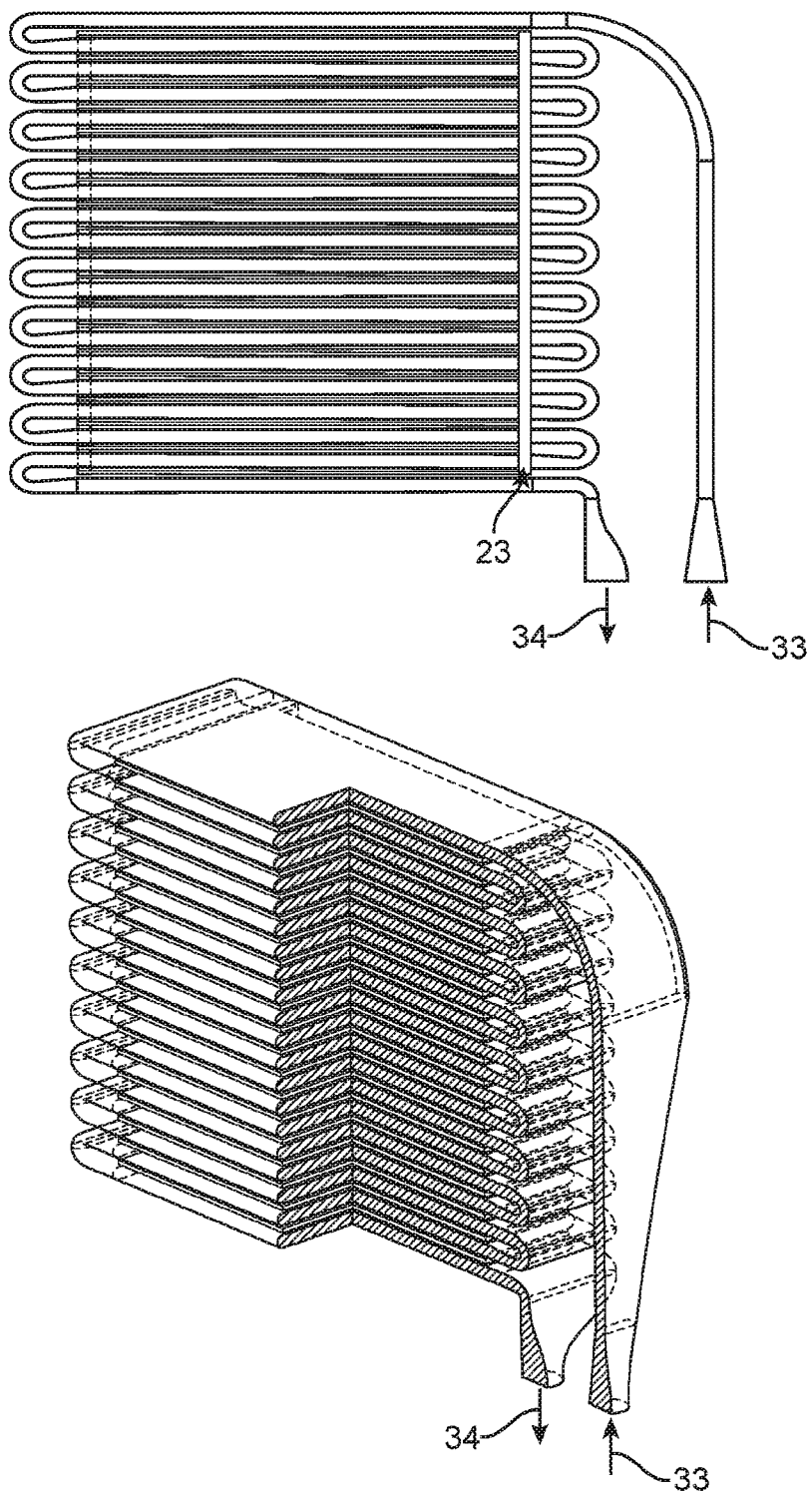
FIG. 70 illustrates a hemofilter device that includes a serpentine channel and a dialysate/conduit.
Figure 71:
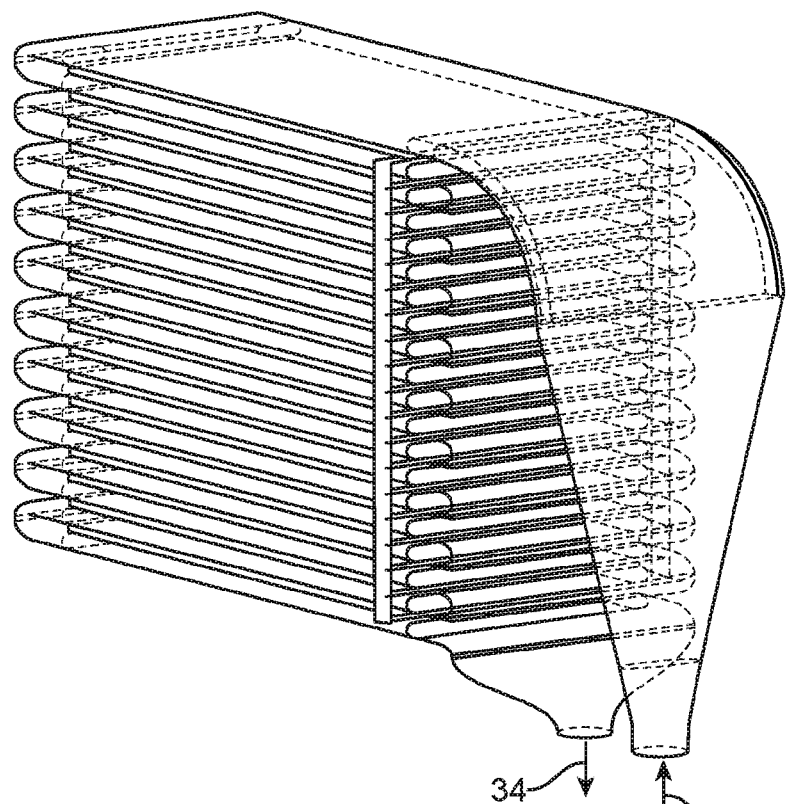
FIGS. 71 and 72 illustrate a hemofilter device that includes a serpentine channel and a ultrafiltrate conduit.
Figure 72:
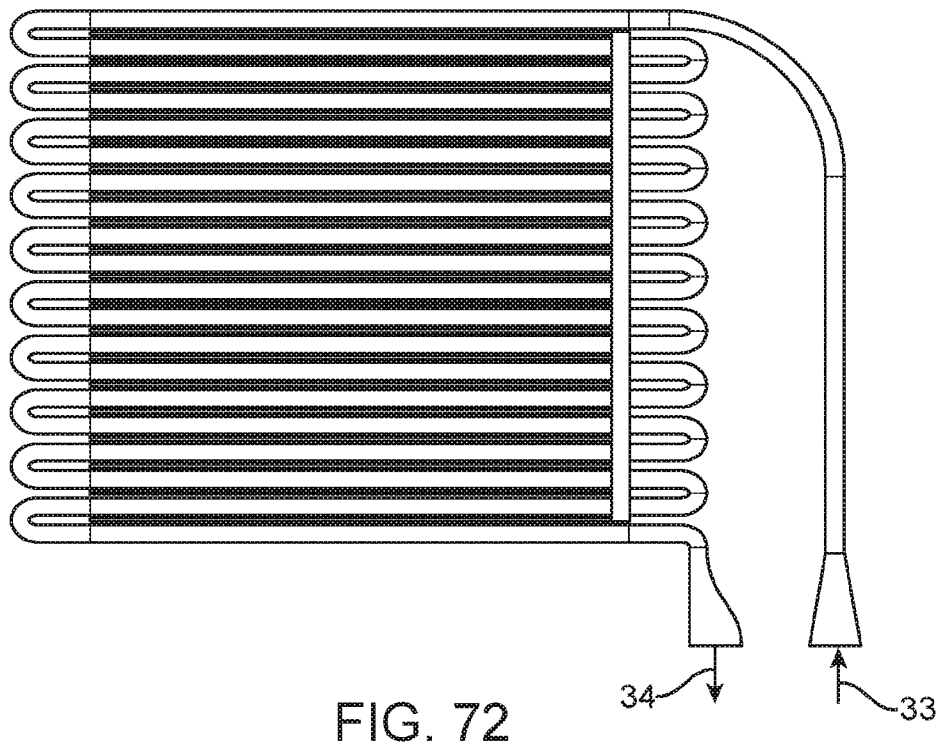

FIGS. 70-72 illustrate a hemofilter with a serpentine channel comprising filtration regions and a dialysate/ultrafiltrate chamber 23 with parallel plate conduits oriented across from the filtration regions for collecting molecules that pass through the filter.

Figure 73:
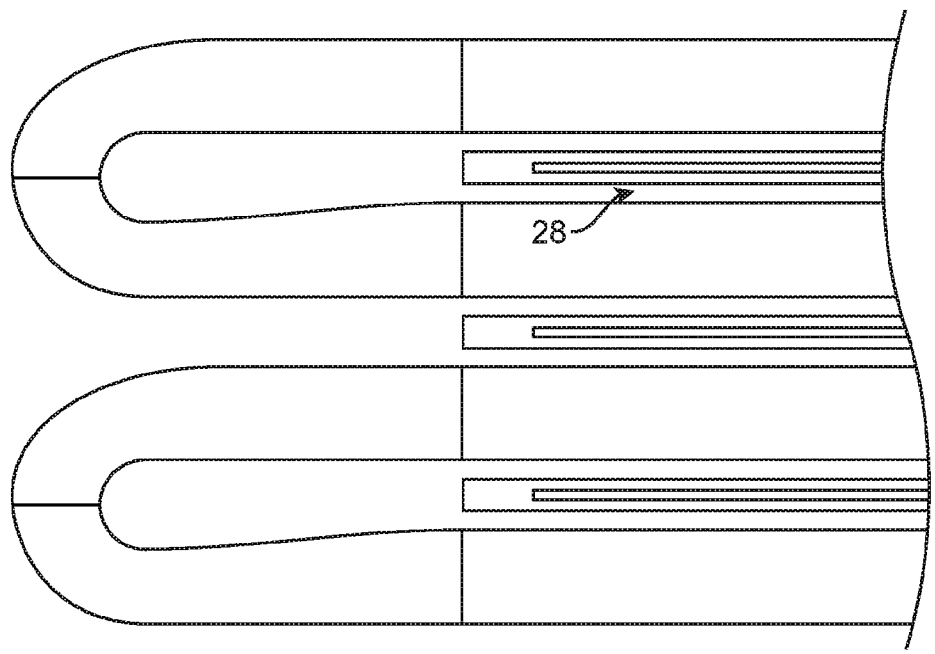
FIG. 73 illustrates a section of a serpentine channels and an ultrafiltrate conduit of a hemofilter device provided herein.

FIG. 73 illustrates serpentine channel of a hemofilter and a dialysate conduit 28 that changes flow direction between 150 to 210 degrees between alternate stacked regions to maintain counter current dialysis flow arrangement.

Figure 74:
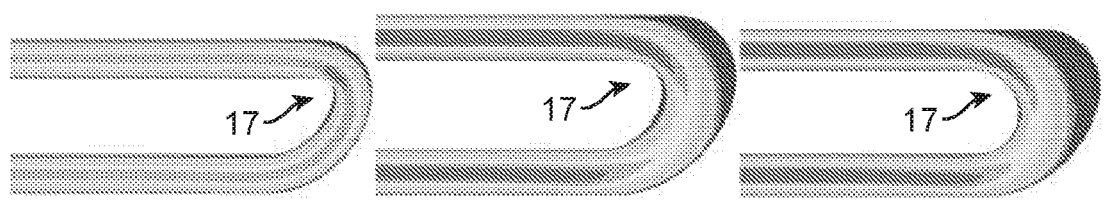
FIG. 74 illustrates a hemofilter where different turnaround regions configurations change flow direction by 150 to 210 degrees.

FIG. 74 illustrates a hemofilter with a serpentine flow channel in which the turnaround regions change flow direction by 150 to 210 degrees at each subsequent filtration region with reference to the filtration regions immediately adjacent to the filtration region. The turnaround region 17 can have different turn trajectories as depicted.

In some embodiments, the channel height varies through each turn. In some embodiments, the change in channel height and/or curvature in the flow reversal sections is configured to maintain the desired level of sustained (time-averaged) wall shear stress along all interior surfaces to minimize the potential for thrombus formation.

FIG. 75 illustrates a hemofilter, where the channel flow shows varying geometric profiles (i.e. circular, elliptical, parabolic, spline). In some embodiments, the channel flow path has configuration 40 comprising a converging flow path prior to turn, wherein the channel height decreases upstream of the channel turnaround by between 0 and 50%. In some embodiments, the channel flow path has configuration 41, where the inner radius of curvature for the turnaround is equal to or greater than half the distance (S) between adjacent parallel channel walls. In some embodiments, the channel flow path has a diverging flow downstream of the turnaround region, where the channel height increases by between 0 and 50%. In some embodiments, the channel flow path has configuration 42, wherein the channel flow path comprises a diverging flow downstream of the turnaround region, wherein the channel height increases by between 0 and 50%, and the flow returns to the initial height after the turn. The serpentine flow channels have an inner radius (R) of curvature at a turnaround region 17 (FIG. 75) equal to or greater than half of the distance between the adjacent parallel conduit walls. Calculation of the inner radius of curvature is shown in Equation 3:

$$R = C \times S;$$

where C is a constant value between 0.5 and 4, R is the inner radius of curvature, and S is the spacing between adjacent parallel conduits.

FIGS. 76A and 76B illustrate a hemofilter having a configuration similar to the hemofilter depicted in FIG. 24 but including twenty filtration sections and an extended inlet having two turnaround sections instead of a single turnaround section as in FIG. 24. The hemofilter shown in FIG. 24 includes an inlet that includes a transition region in which the cross section of the inlet changes from a circular lumen to a rectangular lumen, the rectangular lumen connects to a first filtration section via a turnaround section which reverses the direction of blood flow with reference to the direction in a region upstream to the turnaround section. In the hemofilter illustrated in FIGS. 76A and 76B, the extended inlet includes two turnaround sections in the transition region, such that, in addition to transitioning from a circular to a rectangular lumen, the extended inlet includes two turnaround sections that reverse the direction in which blood flows in the extended inlet twice. In the extended inlet depicted in FIGS. 76A and 76B, the first turnaround section occurs in a transition region of the extended inlet in which the lumen of the inlet is rectangular but has a cross-sectional area smaller than the cross-sectional area of the rectangular lumen of the inlet at and/or after the second turnaround. The second turnaround section connects the first filtration section of the stack to the extended inlet. Therefore, the direction of blood flow is reversed twice in the extended inlet. In contrast, the direction of blood entering the first filtration section of the device in FIG. 25, is changed by about 90 degrees as compared to the direction in the inlet. A hemofilter having the configuration as depicted in FIG. 25 is also referred to as a "Serpentine" hemofilter. A hemofilter having the configuration as depicted in FIGS. 76A and 76B is also referred to as a "Alt Serpentine" hemofilter.

The hemofilter depicted in FIGS. 76A and 76B includes an extended inlet with two turnaround sections where the cross-sectional area of the inlet in the first turnaround section is smaller than the cross-sectional area of the inlet in the second turnaround section. However, in other embodiments, the cross-sectional area at both turnarounds may be the same.

Figure 77:
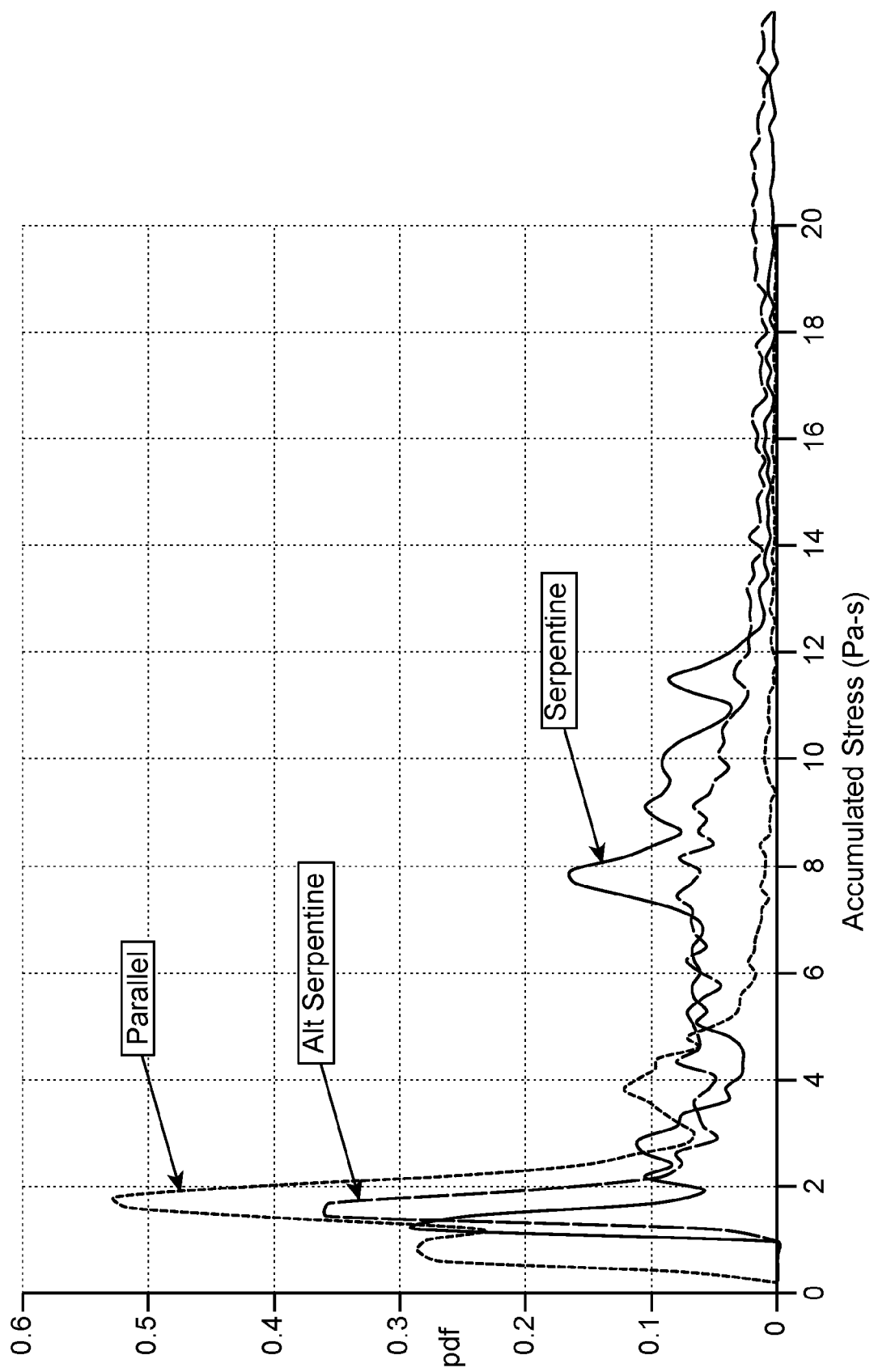
FIG. 77 illustrates probability density function (pdf) and accumulated stress as measured in hemofilters with Parallel configuration, Alt Serpentine configuration, or Serpentine configuration.

FIG. 77 depicts comparison of linear stress accumulation in hemofilters with parallel configuration of the filtration channels, a serpentine configuration of the filtrations channels, or an altered serpentine ("Alt Serpentine") configuration. A hemofilter with parallel configuration of the filtration channels has an extended inlet manifold having a plurality of filtration channels connected directly to the extended inlet (e.g., see FIG. 1). A hemofilter with serpentine filtration channel with an inlet connecting with the first filtration channel at about a 90 degree angle is referred to as "Serpentine" configuration (see, e.g., FIG. 25). A hemofilter with an extended inlet having two turnarounds (about 180 degree angle each), wherein the first turnaround section has a rectangular lumen smaller than the rectangular lumen of the second turnaround section which has a rectangular lumen that matches the cross section of the filtration channel and is connected to the serpentine filtration channel is referred to as "Alt Serpentine" (see, e.g., FIGS. 76A-76B).

Probability density function (pdf) was used to visualize distribution of stress accumulation for the collection of particle tracks. PDF is the statistical distribution of all the stress accumulation values reached by each individual platelet along its corresponding flow trajectory through the device. See Marom and Bluestein, Expert Review of Medical Devices, 13: 113-122, 2016.

Figure 78:
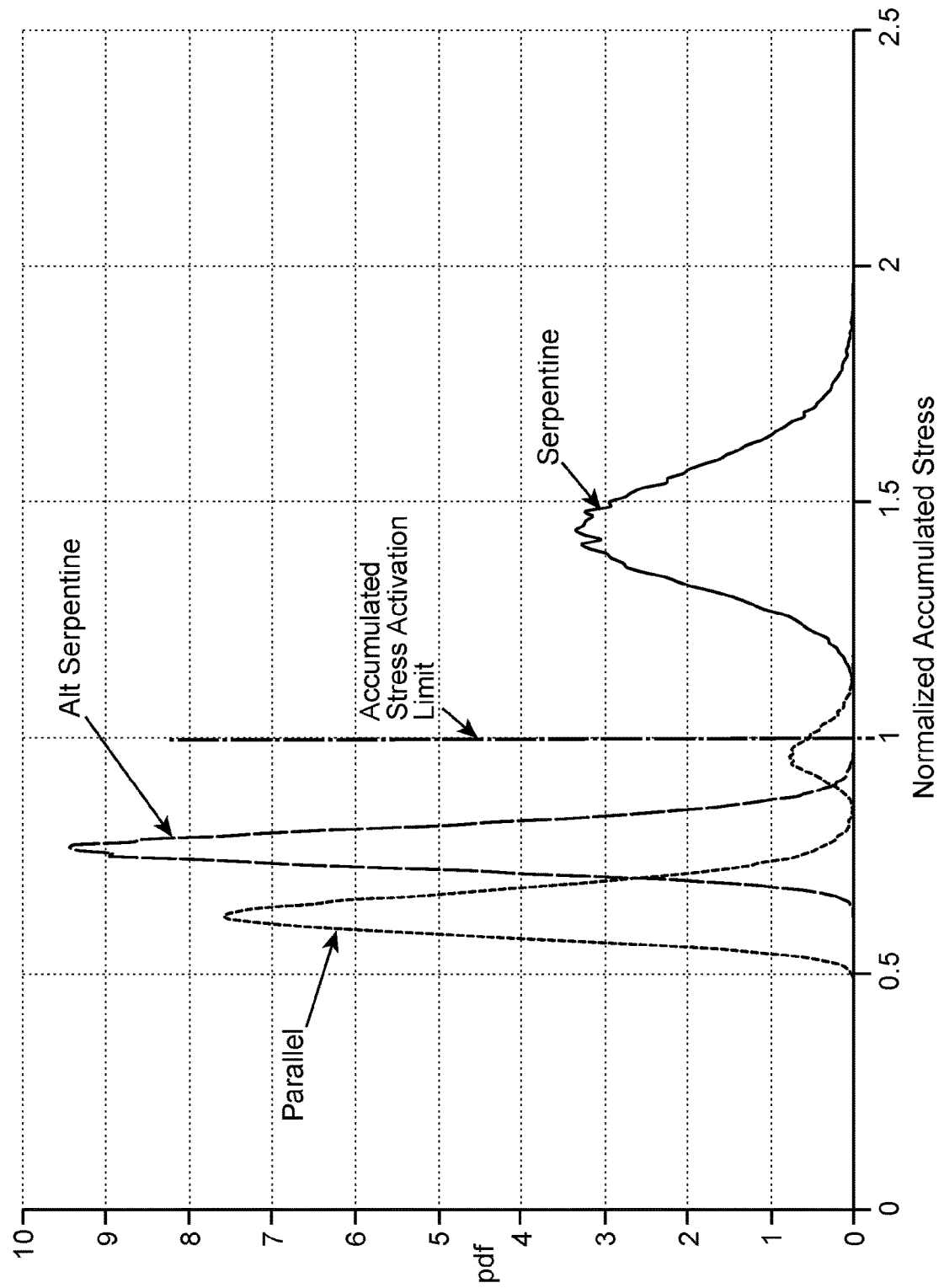
FIG. 78 illustrates probability density function (pdf) and normalized accumulated stress as measured in hemofilters with Parallel configuration, Alt Serpentine configuration, or Serpentine configuration. Accumulated stress activation limit was set at 1.

FIG. 78 shows platelet lifetime normalized accumulated stress in hemofilters with Parallel, Serpentine, or Alt Serpentine configuration. FIG. 78 shows that difference in the degree of change in direction of blood flow in results in a difference in stress accumulation in the hemofilters, with the hemofilters with Parallel (see e.g., FIG. 1) or Alt Serpentine configuration (see, e.g., FIGS. 76A and 76B) having a lower normalized accumulated stress as compared to hemofilter with Serpentine configuration (see, e.g., FIG. 25).

In some embodiments, the hemofilters disclosed herein have a configuration that allow for blood flow at a low shear stress such that platelet accumulated stress remains below the platelet activation limit. Platelet activation limit may be calculated as follows:

$$4.632e\text{-}5\ \tau^{2.30}t,$$

where $\tau$=shear stress (Pa), t=residence time (s). In some embodiments, the hemofilters provided herein are configured to minimize shear stress such that the platelet accumulated stress is below platelet activation limit. The Parallel or Alt Serpentine configurations such as those depicted in FIG. 1 and FIGS. 76A and 76B, respectively have a minimal shear stress such that the platelet accumulated stress is below the platelet activation limit of 1 while the Serpentine configuration offers a shear stress such that the platelet accumulated stress is above the platelet activation limit of 1. In some cases, the platelet accumulated stress may be calculated as described in J. D. Hellums, D. M. Peterson, N. A. Stathopoulos, J. L. Moake and T. D. Giorgio, "Studies on the Mechanisms of Shear-Induced Platelet Activation," Cerebral Ischemia and Hemorheology, 1987.

In some embodiments of the hemofilter of the present invention, ultrafiltrate is generated from filtration channels and enters a series of parallel plate conduits that remove the ultrafiltrate, draining the ultrafiltrate out of the hemofilter.

In some embodiments, ultrafiltrate is generated from parallel plate membranes and enters a series of ultrafiltrate drainage network comprising a combination of parallel plate conduits and non-parallel plate conduits. In some embodiments, ultrafiltrate is generated from parallel plate membranes and enters a series of ultrafiltrate drainage networks that do not comprise parallel plate conduits. In some embodiments, the ultrafiltrate exits parallel plate conduits and enters manifold oriented perpendicular to parallel ultrafiltrate conduits.

In some embodiments, dialysate is distributed to and collected from parallel plate conduits by a manifold oriented perpendicular to parallel plate conduits. In some embodiments, a dialysate is distributed to and collected from a network of dialysate conduits comprising a combination of parallel plate conduits and non-parallel plate conduits. In some embodiments, a dialysate is distributed to and collected from a dialysate conduit network that does not comprise parallel plate conduits. In some embodiments, parallel dialysate conduits run between blood conduits and are separated by a membrane from a blood conduit on both the top and bottom. In some embodiments, mass transfer occurs through both membranes. In some embodiments, the direction of the dialysate flow relative to the blood flow is perpendicular (cross flow), the same (co-current), or the opposite (counter current).

In certain embodiments, the membrane included in the hemofilters (e.g., hemofilter with serpentine channel or plurality of stacked channels) provided herein may include a plurality of pores having a width in the range of 5 nm-5 micron. In certain embodiments, one or more surface of the membrane and or the inner surface of the conduits of the hemofilters may be treated to limit protein adsorption. Such a treatment may include treatments that alter or confer surface charge, surface free energy, or treatments that promote adhesion of specific cell types. Examples of surface treatments can be found, for example, in U.S. Patent Application Publication No. 20090131858, which is hereby incorporated by reference in its entirety.

In certain embodiments, the membrane may include a plurality of nanopores having a circular or slit shaped opening with a diameter or width, respectively, of 1 nm-500 nm, e.g., 1 nm-90 nm, 2 nm-50 nm, 3 nm-40 nm, 4 nm-50 nm, 4 nm-40 nm, 5 nm-50 nm, 5 nm-20 nm, 4 nm-20 nm, 7 nm-100 nm, 12 nm-20 nm, or 5 nm-10 nm. In certain embodiments, the membrane comprises a plurality of micropores having a circular or slit shaped opening with a diameter or width, respectively, in the range of 0.1 µm-5 µm, e.g., 0.1 µm-3 µm, 0.1 µm-0.5 µm, 0.5 µm-1 µm, 1 µm-1.5 µm, 1.5 µm-2 µm, 0.1 µm-1 µm, 0.1 µm-0.8 µm, 0.2 µm-0.7 µm, 0.2 µm-0.6 µm, 0.2 µm-0.5 µm. In certain embodiments, the plurality of pores are slit shaped and have a width as listed herein and have a length in the range of 1 µm-10 µm, e.g., 2 µm-3 µm, 3 µm-4 µm, 4 µm-5 µm, 5 µm-6 µm, 6 µm-7 µm, 7 µm-8 µm, 8 µm 9 µm, or 9 µm-10 µm. In certain cases, the slit shaped, i.e., rectangular pores have a depth of 100-1000 nm, a width of 3 nm-50 nm and a length of 1 micron-5 micron, e.g., a width×length×depth of 5 nm-50 nm×1 micron-2 micron×200 nm-500 nm. The depth of the pores may be defined by the thickness of the membrane which may be in the range of 0.1 micron-1000 micron.

The membrane may have any suitable hydraulic permeability for use in the in vivo filtration device, such as an, artificial kidney. In some cases, the hydraulic permeability of the membrane (e.g., SNM) is about 50 ml/h/mmHg/m$^2$ or greater, e.g., about 75 ml/h/mmHg/m$^2$ or greater, about 100 ml/h/mmHg/m$^2$ or greater, about 150 ml/h/mmHg/m$^2$ or greater, about 200 ml/h/mmHg/m$^2$ or greater, about 250 ml/h/mmHg/m$^2$ or greater, including about 300 ml/h/mmHg/m$^2$ or greater, and in some cases, is about 1,000 ml/h/mmHg/m$^2$ or less, e.g., about 900 ml/h/mmHg/m$^2$ or less, about 800 ml/h/mmHg/m$^2$ or less, about 700 ml/h/mmHg/m$^2$ or less, about 600 ml/h/mmHg/m$^2$ or less, including about 500 ml/h/mmHg/m$^2$ or less. In some embodiments, the hydraulic permeability of the silicon nanoporous membrane is from about 50 ml/h/mmHg/m$^2$ to about 1,000 ml/h/mmHg/m$^2$, e.g., from about 100 ml/h/mmHg/m$^2$ to about 900 ml/h/mmHg/m$^2$, from about 150 ml/h/mmHg/m$^2$ to about 800 ml/h/mmHg/m$^2$, from about 200 ml/h/mmHg/m$^2$ to about 700 ml/h/mmHg/m$^2$, including from about 200 ml/h/mmHg/m$^2$ to about 600 ml/h/mmHg/m$^2$.

In certain embodiments, the in vivo infiltration device, such as, a bioartificial kidney is dimensioned to fit in a body cavity of a subject. The in vivo infiltration device may be rectangular or cylindrical in shape. In certain case, the in vivo infiltration device may have a surface area of 50 cm$^2$ or less, such as 10-30 cm$^2$, 10-25 cm$^2$, 15-25 cm$^2$, 20-25 cm$^2$, 15-30 cm$^2$. In certain cases, the bioartificial kidney may be rectangular and have a length of 3 cm-10 cm, a width of 1 cm-6 cm, and a height of 0.3 cm-2 cm, such as dimension (length×width×height) of 3 cm×1 cm×0.5 cm to 6 cm×4 cm×1 cm, e.g., 3 cm×1 cm×0.5 cm, S cm×2 cm×1 cm, or 6 cm×4 cm×1 cm. In certain embodiments, the overall dimension of the hemofilter, specifically the filtration section of the hemofilter, such as those depicted in the figures provided herein may range from 45 mm-100 mm in height, 80-150 mm in length, and a width of 10-30 mm, such as, height× length×width of 45-80 mm×90-130 mm×10-30 mm, respectively.

Any material suitable for encasing in a housing of a in vivo infiltration device may be used to form the hemofilters provided herein. In some embodiments, the hemofilter may be fabricated, in part, from medical grade plastic, metals, such as, titanium, stainless steel, etc.

In some embodiments, the hemofilter may be encased in a chamber into which an ultrafiltrate produced by filtration of blood in the hemofilter is collected. The chamber may include an opening for draining the ultrafiltrate into a blood vessel or one or both ureter of the individual implanted with the artificial kidney.

In some embodiments the hemofilter may interface with a plurality of channels that collect the ultrafiltrate. In some embodiments, the plurality of channels may terminate into a single outlet. In other embodiments, the plurality of channels may include an inlet for circulating a dialysis fluid and an outlet for exit of the dialysis fluid. The arrangement of the ultrafiltration and dialysate channels may include a parallel plate assembly as described herein.

In some embodiments, the ultrafiltration/dialysis chamber may include a rectangular manifold comprising a plurality of openings connected to a plurality of U-shaped extensions where each U-shaped extension encases at least the filtration regions of the hemofilter and collects the molecules filtering out of the hemofilter and returns the dialysate/ultrafiltrate to the rectangular manifold for draining out of the dialysate/ultrafiltrate.

The flow rate of blood flowing through the hemofilters disclosed herein may be in the range of 500 ml/min-2000 ml/min, e.g., 500 ml/min-1500 ml/min, 500 ml/min-1000 ml/min, 500 ml/min-900 ml/min, 600 ml/min-900 ml/min, or 700 ml/min-900 ml/min. The flow rate of blood flowing through the channel(s) of the hemofilters disclosed herein may be in the range of 25 ml/min-100 ml/min, e.g., 25 ml/min-75 ml/min, 25 ml/min-70 ml/min, 25 ml/min-50 ml/min, 25 ml/min-45 ml/min, or 35 ml/min-45 ml/min.

In certain embodiments, the inlet and outlet manifolds may be shortened or lengthened based on desired parameters, such as, relative position within the in vivo infiltration device, relative position of the bioreactor chamber of the artificial kidney, etc. Similarly, the inlet and outlet conduits of the hemofilter with the serpentine channel may be shortened or lengthened based on desired parameters, such as, relative position within the in vivo infiltration device, relative position of the bioreactor chamber of the artificial kidney, etc.

Methods

Hemofilters of the present disclosure and in vivo infiltration device, e.g., artificial kidneys that include the same, find use in performing hemodialysis and/or hemofiltration. In general terms, a method for hemodialysis may include connecting a blood inlet and a blood outlet of the hemofilter to an individual's circulatory system such that blood circulates from the circulatory system, through the channel(s) of the hemofilter, and back into the circulatory system. The connection may be made at a suitable point in the circulatory system, such as, without limitation, the renal artery and vein. Thus, in some embodiments, the blood inlet is connected to the renal artery, and the blood outlet is connected to the renal vein. A suitable vascular graft connector may be used to connect the blood inlet and outlet to the circulatory system.

The vascular graft connectors may include any suitable biocompatible tubing for establishing a blood flow between the individual's circulation and the hemofilter. In some embodiments, the vascular graft connector includes a polymeric material, including, but not limited to, polyesters, such as polyethylene terephthalate (PET); fluorinated polymers, such as polytetrafluoroethylene (PTFE); polyurethanes and combinations thereof. Suitable polymers include DACRON™ (PET) from DuPont, and FUSION' (expanded PTFE and PET) from Maquet. The vascular graft connectors may have a suitable stiffness so as to provide flexibility for implanting at an implantation site, and to prevent excessive bending that may collapse the inner passageway (i.e., prevent kinking).

In some cases, the present method includes implanting the in vivo infiltration device, e.g., artificial kidney in the body of the individual. The in vivo infiltration device may be implanted using any suitable surgical means. In some cases, the in vivo infiltration device includes one or more (e.g., two or more, three or more, or four or more) suture tabs, and the device is positioned in an implantation site by suturing the in vivo infiltration device to a tissue wall of the implantation site via the suture tabs. In some embodiments, the in vivo infiltration device is enveloped in a biocompatible mesh (e.g., polymeric mesh, such as a polypropylene mesh), and the in vivo infiltration device is positioned in an implantation site by suturing the in vivo infiltration device to a tissue wall of the implantation site via the mesh.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A hemofilter for use in filtering blood in vivo, the hemofilter comprising:
   an extended inlet manifold;
   a plurality of filtration channels; and
   an extended outlet manifold,
   the extended inlet manifold comprising:
   a first region comprising:
      a circular inlet configured for connection to a blood vessel of an individual; and a transition section in which lumen of the extended inlet manifold transitions from having a circular cross-section to having a rectangular cross-section; and
   a second region comprising a U-shaped turn and followed by a linear tapered section, the linear tapered section comprising a plurality of openings in fluid communication with the plurality of filtration channels,
   wherein the plurality of filtration channels are arranged in a spaced-apart stacked configuration and are in fluid communication with a plurality of openings in a first region of the extended outlet manifold,
   wherein the first region of the extended outlet manifold is parallel to the linear tapered section of the extended inlet manifold and is reverse-tapered with reference to the linear tapered section of the extended inlet manifold and wherein the extended outlet manifold comprises a second region comprising:
      a transition section in which lumen of the extended outlet manifold transitions from having a rectangular cross-section to having a circular cross-section; and
      a circular outlet defined by the circular cross-section of the extended outlet manifold, and
   wherein the hemofilter is configured for entry of blood through the circular inlet and for transporting the blood through the transition section of the extended inlet manifold to the tapered linear section, into the plurality of filtration channels to the first region of the extended outlet manifold, into the transition section of the extended outlet manifold, and exit via the circular outlet.

2. The hemofilter of claim 1, wherein channels of the plurality of filtration channels are rectangular and are stacked in a parallel configuration.

3. The hemofilter of claim 1, wherein the transition section in extended inlet manifold includes a turn which changes direction of blood flow with reference to the direction in the circular inlet by 60°-120° and/or wherein the U-shaped turn in the second region of the extended inlet manifold changes the direction of blood flow with reference to the direction in the transition section by 150° and 210°.

4. The hemofilter of claim 1, wherein the tapered section of the extended inlet manifold decreases in height and/or the tapered section of the extended inlet manifold decreases in width.

5. The hemofilter of claim 1, wherein the plurality of filtration channels comprises a first curved region connected to the tapered section of the extended inlet manifold, a linear section, and a second curved region connected to a reverse-tapered section of the extended outlet manifold, wherein a curvature of the first curved region is opposite to a curvature of the second curved region.

6. The hemofilter of claim 1, wherein the plurality of filtration channels each define a rectangular channel lumen enclosed by a top surface, a bottom surface, and side walls connecting the top and bottom surfaces, wherein the top surface comprises a membrane for filtration of blood in the rectangular channel lumen and/or the bottom surface comprises a membrane for filtration of blood in the rectangular channel lumen.

7. The hemofilter of claim 1, wherein the tapered section of the extended inlet manifold and the reverse-tapered section of the extended outlet manifold and a top channel of the plurality of filtration channels and a bottom channel of the plurality of filtration channels are arranged in shape of a parallelogram.

8. The hemofilter of claim 1, wherein the plurality of filtration channels comprises 2-50 channels, wherein each of the plurality of filtration channels has a length of 10 mm-200 mm, a width of 5 mm-100 mm, and a height of 0.5 mm-2.5 mm.

9. A hemofilter for use in filtering blood in vivo, the hemofilter comprising:
an extended inlet conduit;
a single serpentine filtration channel;
and an outlet conduit;
the extended inlet conduit comprising:
 a first region comprising:
  an inlet having a circular cross section shape configured for connection to a blood vessel of an individual; and
  a transition region in which lumen enclosed by the first region transitions from the circular cross section shape into a rectangular cross section shape;
 a second region comprising a rectangular cross section and a curved region connected to the single serpentine filtration channel;
the single serpentine filtration channel comprising:
 a plurality of filtration sections arranged in a spaced-apart stacked configuration wherein the plurality of filtration sections are connected via turnaround sections; and
the outlet conduit comprising:
 first region having a rectangular cross-section; and
 a second region that transitions from rectangular to a circular cross section and terminates in a circular outlet configured for connection to a blood vessel of the individual.

10. The hemofilter of claim 9, wherein the plurality of filtration sections each define a rectangular channel lumen enclosed by a top surface, a bottom surface, and side walls connecting the top and bottom surfaces, wherein the top surface comprises a membrane for filtration of blood in the rectangular channel lumen and/or the bottom surface comprises a membrane for filtration of blood in the rectangular channel lumen.

11. The hemofilter of claim 9, wherein the plurality of filtration sections comprises 2-50 filtration sections, each disposed between two turnaround sections, wherein each of the plurality of filtration sections has a length of 10 mm-200 mm, a width of 5 mm-100 mm, a height of 0.5 mm-2.5 mm.

12. The hemofilter of claim 9, wherein a curvature of the turnaround sections is non-uniform, circular, or elliptical.

13. The hemofilter of claim 9, wherein a height of a filtration section increases from a proximal end, at which blood enter the filtration section, towards a distal end, at which blood exits the filtration section and flows to a turnaround section.

14. The hemofilter of claim 9, wherein the extended inlet conduit is substantially parallel to the plurality of filtration sections and wherein the curved region is a turnaround region that reverses direction of blood flow in a first filtration section with reference to direction of blood flow in the extended inlet conduit and wherein the outlet conduit is substantially parallel to the plurality of filtration sections.

15. The hemofilter of claim 9, wherein the extended inlet conduit is substantially perpendicular to the plurality of filtration sections and wherein the curved region changes direction of blood flow in a first filtration section to which the blood flows from the inlet conduit by about 90 degree relative to the direction of blood flow in the extended inlet conduit and wherein the outlet conduit is substantially perpendicular to the plurality of filtration sections.

16. A hemofilter for use in filtering blood in vivo, the hemofilter comprising:
an extended inlet conduit;
a single serpentine filtration channel;
and an outlet conduit;
the extended inlet conduit comprising:
 an inlet;
 a first transition region;
 a first turnaround section;
 a second transition region;
 a second turnaround section;
 wherein in the first transition region the inlet transitions from a circular cross section, configured for connection to a blood vessel of an individual, into a substantially rectangular cross section,
 wherein the rectangular cross section at the end of the first transition region matches the rectangular cross section of the first turnaround section,
 wherein in the second transition region the first turnaround section expands in width such that a rectangular cross section at the end of the second transition region matches a rectangular cross section of the second turnaround section,
 wherein the rectangular cross section of the second turnaround section matches that of the single serpentine filtration channel;
the single serpentine filtration channel comprising:
 a plurality of filtration sections arranged in a spaced-apart stacked configuration wherein the filtration sections are connected via turnaround sections; and
the outlet conduit comprising:
 first region having a rectangular cross-section; and
 a second region that transitions from rectangular to a circular cross section and terminates in a circular outlet configured for connection to a blood vessel of an individual.

17. The hemofilter of claim 16, wherein the plurality of filtration sections each define a rectangular channel lumen enclosed by a top surface, a bottom surface, and side walls connecting the top and bottom surfaces, wherein the top surface comprises a membrane for filtration of blood in the rectangular channel lumen and/or the bottom surface comprises a membrane for filtration of blood in the rectangular channel lumen.

18. The hemofilter of claim 16, wherein the plurality of filtration sections comprises 2-50 filtration sections, wherein each of the plurality of filtration sections has a length of 10 mm-200 mm, a width of 5 mm-100 mm, and a height of 0.5 mm-2.5 mm.

19. The hemofilter of claim 16, wherein a curvature of the turnaround sections is non-uniform, circular, or elliptical or wherein height of the turnaround section is non-uniform.

20. The hemofilter of claim 16, wherein a height of a filtration section increases from a proximal end, at which blood enter the filtration section, towards a distal end, at which blood exits the filtration section and flows to a turnaround section.

* * * * *

UNITED STATES PATENT AND TRADEMARK OFFICE
CERTIFICATE OF CORRECTION

| | | |
|---|---|---|
| PATENT NO. | : 11,511,027 B2 | Page 1 of 1 |
| APPLICATION NO. | : 16/624226 | |
| DATED | : November 29, 2022 | |
| INVENTOR(S) | : Shuvo Roy et al. | |

It is certified that error appears in the above-identified patent and that said Letters Patent is hereby corrected as shown below:

In the Specification

In Column 30, Line 65, "FUSION'" should read --FUSION™--

In the Claims

In Column 34, Line 1, please insert --extended-- after "from the"

In Column 34, Line 20, "wherein the" should read --wherein a--

In Column 34, Line 21, "matches the" should read --matches a--

Signed and Sealed this
Ninth Day of May, 2023

Katherine Kelly Vidal
*Director of the United States Patent and Trademark Office*